US006005092A

United States Patent [19]
Shoseyov et al.

[11] Patent Number: 6,005,092
[45] Date of Patent: Dec. 21, 1999

[54] *ARABIDOPSIS THALIANA* ENDO-1,4-β-GLUCANASE GENE AND PROMOTER

[75] Inventors: Oded Shoseyov, Karme Yosef; Ziv Shani, Rehovoth, both of Israel

[73] Assignee: Yissum Research Development Company of the Hebrew University of Jerusalem, Israel

[21] Appl. No.: 09/006,636

[22] Filed: Jan. 13, 1998

[30] Foreign Application Priority Data

Jul. 27, 1997 [IL] Israel ........................................ 121404

[51] Int. Cl.⁶ ............................. C12N 5/04; C12N 15/29; C12N 15/56; C12N 15/82
[52] U.S. Cl. .................. 536/23.6; 536/24.1; 800/278; 800/290; 435/209; 435/320.1; 435/419; 435/468
[58] Field of Search ................................ 536/23.6, 24.1; 435/209, 298, 320.1, 419, 440, 468; 800/276, 278, 288, 290, 295, 298, DIG. 9, 52, 200, 205

[56] References Cited

U.S. PATENT DOCUMENTS

| | | | |
|---|---|---|---|
| 5,137,819 | 8/1992 | Kilburn et al. ........................ | 435/179 |
| 5,202,247 | 4/1993 | Kilburn et al. ........................ | 435/195 |
| 5,258,502 | 11/1993 | Kuranda ................................ | 530/350 |
| 5,496,934 | 3/1996 | Shoseyov et al. ..................... | 536/23.7 |
| 5,530,187 | 6/1996 | Lamb et al. .......................... | 800/278 |
| 5,643,791 | 7/1997 | Warren et al. ....................... | 435/252.33 |
| 5,705,375 | 1/1998 | Van Ooyen et al. .................. | 435/468 |

FOREIGN PATENT DOCUMENTS

WO 94/24158   10/1994   WIPO.

OTHER PUBLICATIONS

Clackson et al., 1994, "In vitro selection from protein and peptide libraries", Trends Biotech. 12:173–184.
Goldstein et al., 1993, "Characterization of the cellulose–binding domain of the clostridium cellulovorans cellulose–binding protein", J. Bacteriol. 175(18):5762–5768.
Odell et al., 1985, "Identification of DNA sequences required for activity of the cauliflower mosaic virus 35S promoter", Nature 313:810–812.
Scherban et al., 1995, "Molecular cloning and sequence analysis of expansins—a Highly conserved, multigene family of proteins that mediate cell wall extension in plants", PNAS USA 92:9245–9249.
Yu et al., 1996, "Affinity maturation of phage–displayed peptide ligands", Meth. Enzymol. 267:3–27.
Kim et al, Plant Mol. Biol., vol. 24, pp. 106, 107, 110, 1994.
Shani et al, Plant Mol. Biol., vol. 34, pp. 837–840, 1997.
Ohmiya et al, J. Bacteriol., vol. 171, pp. 6771–6772, 1989.
Nakamura et al, Plant Cell Physiol., vol. 36, p. 1231, 1995.
Cabib, Enric, "Chitinase from *Serratia marcescens*," Methods in Enzymology 161:460–462 (1988).
Greenwood et al., "Fusion to an endoglucanase allows alkaline phosphatase to bind to cellulose," EBS Letters 244(1):127–131 (1989).

Shoseyov et al., "Essential 170–kDa subunit for degradation of crystalline cellulose by *Clostridium cellulovorans* cellulase," Proc. Natl. Acad. Sci. USA 87:2192–2195 (1990).
Shoseyov et al., "Immobilized Endo–β–glucosidase Enriches Flavor of Wine and Passion Fruit Juice," JAFCU 38(6):1387–1390 (1990).
Klyosov, Anatole A., "Trends in Biochemistry and Enzymology of Cellulose Degradation," Biochemistry 29(47):10577–10585 (1990).
Shoseyov et al., "Primary sequence analysis of *Clostridium cellulovorans* cellulose binding protein A," Proc. Natl. Acad. Sci. USA 89:3483–3487 (1992).
Din et al., "Non–Hydrolytic Disruption of Cellulose Fibres by the Binding Domain of a Bacterial Cellulase," Bio/Technology 9:1096–1099 (1991).
Gerngross, et al., 1993, "Sequencing of a *Clostridium thermocellum* gene (cipA) encoding the cellulosomal $S_L$–protein reveals an unusual degree of internal homology," Molecular Biology, vol. 8, No. 2, pp. 325–334.
Hazlewood, et al., 1993, Gene sequence and properties of Cell, a family E endoglucanase from *Clostridium thermocellum*, Journal of General Microbiology, vol. 139: pp. 307–316.

(List continued on next page.)

*Primary Examiner*—David T. Fox
*Assistant Examiner*—Ashwin Mehta
*Attorney, Agent, or Firm*—Pennie & Edmonds LLP

[57] ABSTRACT

The present invention discloses genetically engineered plants which display altered structure or morphology. The transgenic plants express a cell wall modulation transgene or gene construct that results in the altered structure or morphology. The altered structure or morphology can be associated with, for example, altered biomass, growth, yield, greater or less resistance to biodegradation, more or less digestible to ruminants, altered cellulose content, larger leaves/normal hypocotyls or smaller leaves/longer hypocotyls, etc. compared to a non-transgenic plant of the same species. The cell wall modulation transgene can be any cellulose binding domain, a cellulose binding protein, or a cell wall modifying protein or enzyme such as endoxyloglucan transferase, xyloglucan endo-transglycosylase, an expansin, cellulose synthase, or a novel isolated endo-1,4-β-glucanase of *Arabidopsis thaliana*. The invention also discloses transgenic plants containing a gene construct comprising a promoter operably linked to the cell wall modulation protein or polypeptide gene and may further comprise a sequence encoding a secretion signal peptide. In particular, the invention discloses transgenic plants containing a gene construct comprising the cel1 promoter, operably linked to the cel1 signal peptide and any cellulose binding domain. Methods for modulating plant growth by transgenic expression of a cell wall modulating protein or polypeptide are also disclosed. The present invention also discloses a novel, isolated *Arabidopsis thaliana* endo-1,4-β-glucanase gene (cel1), its promoter (cel1 promoter) and polypeptide (Cel1) and recombinant nucleic acid vectors containing the cel1 gene with or without a secretion signal peptide sequence and/or the cel1 promoter.

11 Claims, 29 Drawing Sheets

OTHER PUBLICATIONS

Hansen, et al., 1992, "celA from *Bacillus lautus* PL236 Encodes a Novel Cellulose–Binding Endo–β–1,4–Glucanase," *Journal of Bacteriology*, vol. 174, No. 11, pp. 3522–3531.

Saul, et al., 1989, "Nucleotide sequence of a gene from *Caldocellum saccharolyticum* encoding for exocellulase and endocellulase activity," *Nucleic Acids Research*, vol. 17, No. 1, p. 439.

MacKay, et al., 1986, "Structure of a *Bacillus subtilis* endo–β–1,4–glucanase gene," *Nucleic Acids Research*, vol. 14, No. 22, pp. 9159–9170.

Jauris, et al., 1990, "Sequence analysis of the *clostridium stercorarium* celZ gene encoding a thermoactive cellulase (Avicelase I): Identification of catalytic and cellulose–binding domains," *Mol. Gen. Genet.*, vol. 223: pp. 258–267.

Poole, et al., 1992, Identification of the cellulose–binding domain of the cellulosome subunit S1 from *Clostridium thermocellum* YS, *FEMS Microbiology Letters*, vol. 99: pp. 181–186.

Foong et al., 1991, "Nucleotide sequence and characteristics of endoglucanase gene engB from *Clostridium cellulovorans*," *Journal of General Microbiology* vol. 137:1729–1736.

Shoseyov et al., 1991, "Nucleotide Sequence of *Clostridium cellulovorans* gene homologous to cyclic–AMP dependent kinase," *Nucleic Acids Res.* vol. 19:1710.

Shoseyov et al., 1990, "Cloning of 170 dKa *Clostridium cellulovorans* Cellulase Subunit: An Essential Protein for the Degradation of Crystalline Cellulose," *Abstracts of the Annual Meeting of the American Society for Microbiology* O–24, p. 267.

Shoseyov et al., 1990, "Cloning of *Clostridium Cellulovorans* Endo–1, 4–β–Glucanase Genes," *Biochemical Biophysical Research Communications* vol. 169(2):667–672.

Bowie et al., 1990, "Deciphering the Message in Protein Sequences Tolerance to Amino Acid Substitutions," *Science* vol. 247:1306–1310.

Sambrook et al., "Detection and Analysis of Proteins Expressed from Cloned Genes," *Molecular Cloning, A Laboratory Manual*, 2nd ed., pp. 18.2–18.75.

Greenwood et al., 1992, "Cellulose–binding domains: potential for purification of complex proteins," *Protein Engineering* vol. 5:361–365.

Ong et al., 1993, "The Cellulose–Binding Domain ($CBD_{Cex}$) of an Exoglucanase from *Cellulomonas fimi:* Production in *Escherichia coli* and Characterization of the Polypeptide," *Biotechnology and Bioengineering* vol. 42:401–409.

Durrant et al., 1991, "The non–catalytic C–terminal region of endoglucanase E. from *Clostridium thermocellum* contains a cellulose–binding domain," *Biochem. J.* vol. 273:289–293.

Ong et al., 1989, "The cellulose–binding domains of cellulases: tools for biotechnology," *TibTech* vol. 7:239–243.

Poole et al., 1991, "Characterization of hybrid proteins consisting of the catalytic domains of Clostridium and Ruminococcus endoglucanases, fused to Pseudomonas non–catalytic cellulose–binding domains," *Biochem. J.* vol. 279:787–792.

Cosgrove, 1993, "How Do Plant Cell Walls Extend?", *Plant Physiol.* vol. 102:1–6.

Roberts, 1994, "The plant extracellular matrix: in a new expansive mood", *Curr. Opin. Cell. Biol.* vol. 6:688–694.

McQueen–Mason et al., 1995, "Expansion Mode of Action on Cell Walls: Analysis of Wall Hydrolysis, Stress Relaxation, and Binding", *Plant Physiol.* vol. 107:87–100.

Shoseyov et al., 1992, "The Role of Endo–1,4–Beta–Glucanase in Plant Cell Elongation. In–Vitro Studies of Peach Pollen", *Acta. Hort.* vol. 329:225–227.

Verma et al., 1975, "Regulation and in Vitro Translation of Messenger Ribonucleic Acid for Cellulase from Auxin–treated Pea Epicotyls", *J. Biol. Chem.* vol. 250:1019–1026.

Cass et al., 1990, "Isolation and characterization of a cellulase gene family member expressed during avocado fruit ripening", *Mol. Gen. Genet.* vol. 223:76–86.

Fischer and Bennett, 1991, "Role of Cell Wall Hydrolases in Fruit Ripening", *Ann. Rev. Plant Physiol. Plant Mol. Biol.* vol. 42:675–703.

Lashbrook et al., 1994, "Two divergent Endo–β–1,4–glucanase Genes Exhibit Overlapping Expression in Ripening Fruit and Abscising Flowers", *Plant Cell* vol. 6:1485–1493.

Tucker et al., 1987, "Avocado cellulase: nucleotide sequence of a putative full–length cDNA clone and evidence for a small gene family", *Plant Mol. Biol.* vol. 9:197–203.

Kemmerer et al., 1994, "Comparative Study of Cellulases Associated with Adventitious Root Initiation, Apical Buds, and Leaf, Flower, and Pod Abscission Zones in Soybean", *Plant Physiol.* vol. 104:557–562.

Tucker et al., 1991, "Sequence Analysis and Comparison of Avocado Fruit and Bean Abscission Cellulases", *Plant Physiol.* vol. 95:928–933.

Bevan, 1984, "Binary Agrobacterium vectors for plant transformation", *Nuc. Acid Res.* vol. 12:8711–8721.

Rogers et al., 1986, "Gene Transfer in Plants: Production of Transformed Plants Using Ti Plasmid Vectors", *Methods Enzymol.* vol. 118:627–641.

Ross et al., 1991, "Cellulose Biosynthesis and Function in Bacteria", *Microbiological Reviews* vol. 55:35–58.

Benziman et al., 1980, "Cellulose biogenesis: Polymeriazation and crystallization are coupled processed in *Acetobacter xylinum*", *Proc. Natl. Acad. Sci. USA* vol. 77:6678–6682.

Haigler, 1991, "Relationship between polymerization and crystallization in microfibril biogenesis," in: *Biosynthesis and Biodegradation of Cellulose*, pp. 99–124, eds C.H. Haigler and P.J. Weimer, Marcel Dekker, Inc., New York.

Waaland and Waaland, 1975, "Analysis of Cell Elongation in Red Algae by Fluorescent Labelling", *Planta* vol. 126:127–138.

Brown et al., 1982, "Experimental Induction of Altered Nonmicrofibrillar Cellulose", *Science* vol. 218:1141–1142.

Haigler et al., 1988, "Electron Diffraction Analysis of the Altered Cellulose Synthesized by *Acetobacter xylinum* in the Presence of Fluorescent Brightening Agents and Direct Dyes", *J. Ultrastruct. Mol. Struct. Res.* vol. 98:299–311.

Tucker et al., 1988, "Bean Abscission Cellulase: Characterization of a cDNA Clone and Regulation of Gene Expression by Ethylene and Auxin", *Plant Physiol.* vol. 88:1257–1262.

Haigler et al., 1980, "Calcofluor White ST Alters the in vivo Assembly of Cellulose Microfibrils", *Science* vol. 210:903–906.

Larson et al., 1996, "A cellulose–binding protein from *Ruminococcus albus* possesses an amino–terminal motif characteristic of Type 4 fimbrial proteins", *Microbial & Comparative Genomics* vol. 1:380.

Shoseyov, 1992, "Endo–(1,4)–β–Glucanase Gene Expression During Adventitious Root Formation In Mung Bean Cuttings", Thesis Submitted to the Faculty of Agriculture of the Hebrew University of Jerusalem for the Degree "Master of Science".

Tomme et al., 1995, "Cellulose–Binding Domains: Classification and Properties", ACS Symposium Series 618/Enzymatic Degradation of Insoluble Carbohydrates, Chapter 10, pp. 142–161.

Gilkes N.R. et al., "Domains in Microbiol. β–1,4 Glycanases: Sequence Conservation, Function, and Enzyme Families", *Micro Biological Reviews,* vol. 55, No. 2:303–315 (Jun. 1991).

Hatfield R.D., Nevins, D.J., "Hydrolytic Activity and Substrate Specificity of an Endoglucanase from *Zea mays* Seedling Cell Walls", *Plant Physiol.,* vol. 83:203–207 (Jan. 1987).

Hayashi T. et al., "Pea Xyloglucan and Cellulose. II. Hydrolysis by Pea Endo–1,4–β–Glucanases", *Plant Physiol.* vol. 75:605–610 (Mar. 1984).

Wu, S. et al., "Characterization of an Endo–β–1,4–Glucanase Gene Induced by Auxin in Elongating Pea Epicotyls" *Plant Physiol.,* vol. 110:163–170 (Jan. 1996).

Fry, S.C., "The Growing Plant Cell Wall: Chemical and Metabolic Analysis", monograph published by *Longman Scientific & Technical,* Chapter 11:279–285 (1988).

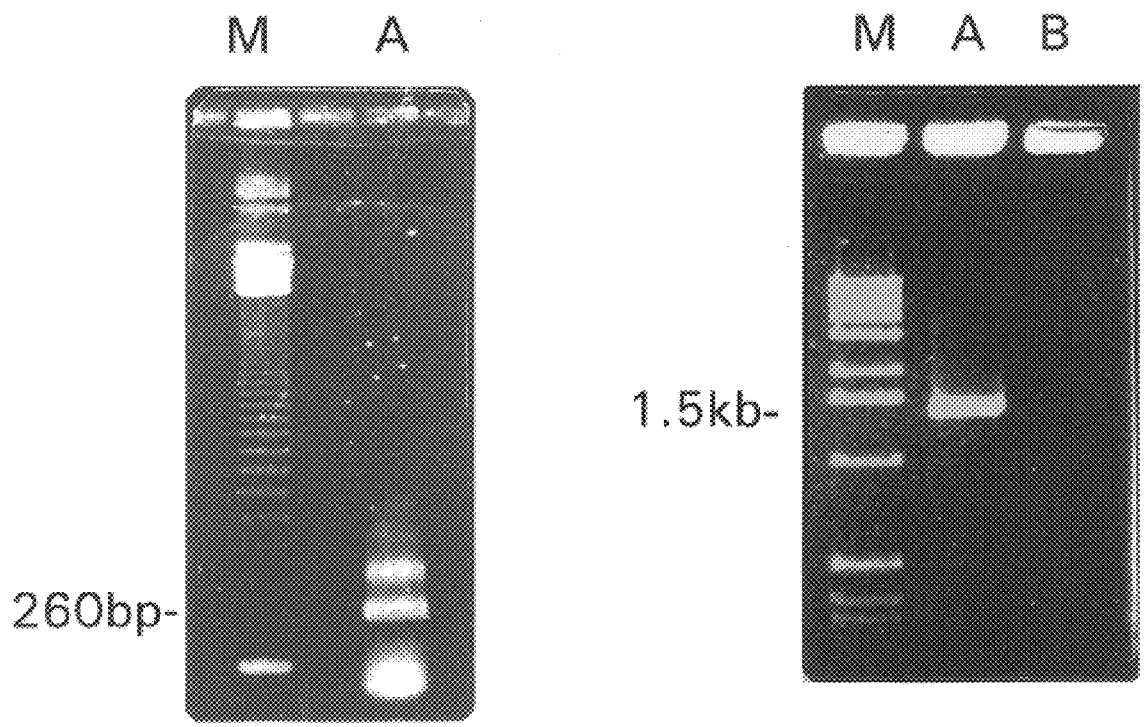
FIG.1
FIG.3
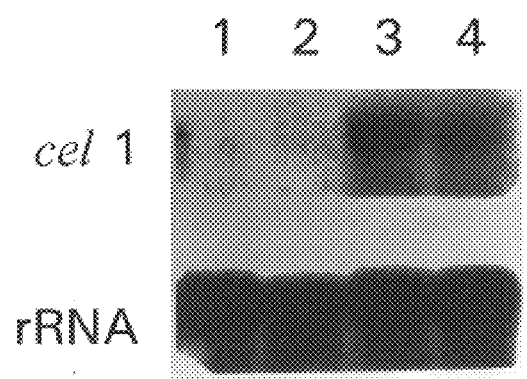
FIG.6

```
  2  ARKSLIFPVILHAVLLFSPPIYSAGH.DYRDALRKSILFFEGQRSGKLPP   50
     ..||:  :::.|::     ..||:. .|.||| |||||||||||||||.
  5  SPLSLFHLLLVCTVMV...KCCSASDLHYSDALEKSILFFEGQRSGKLPT   51

51  DQRLKWRRDSALRDGSSAGVDLSGGYYDAGDNIKFGFPMAFTTTMLSWSI  100
     :|||.|| ||:|.||||   ||| ||||||||:|||:|||||||||.|:|
 52  NQRLTWRGDSGLSDGSSYHVDLVGGYYDAGDNLKFGLPMAFTTTMLAWGI  101

101  IDFGKTMGPELRNAVKAVKWGTDYLLKA.TAIPGVVFVQVGDAYSDHNCW  149
     |:||  |...::  ||   |:::|||||||| ||... ::|||::  .||.||
102  IEFGCLMPEQVENARAALRWSTDYLLKASTATSNSLYVQVGEPNADHRCW  151

150  ERPEDMDTLRTVYKIDRAHPGSDVAGETAAALAAASIVFRKRDPAYSRLL  199
     |||||||  |.|||:.   .:|||||||:|||||||||||  ..|..||   |
152  ERPEDMDTPRNVYKVSTQNPGSDVAAETAAALAAASIVFGDSDSSYSTKL  201

200  LDRATRVFAFANRYRGAYSNSLYHADCPFYCDFNGYQDELLWGAAWLHKA  249
     |.  |.:||.||:.|||.||:||  .|||||.::.||.||||||||.|||:|
202  LHTAVKVFEFADQYRGSYSDSLGSVVCPFYCSYSGYNDELLWGASWLHRA  251

250  SRKRAYREFIVKNEVILKAGDTINEFGWDNKHAGINVLISKEVLMGKAEY  299
     |.. .|..:|  .|:  .|  |:|.  .|:||:|:.|..||:||:.| :: |
252  SQNASYMTYIQSNGHTLGADDDDYSFSWDDKRVGTKVLLSKGFLQDRIEE  301

300  FESFKQNADGFICSILPGISHPQVQYSRGGLLVKTGGSNMQHVYSLSFLL  349
     :: :| :.|.:|||::||.|  |.||..|||| |.::||:|.||| .|||
302  LQLYKVHTDNYICSLIPGTSSFQAQYTPGGLLYKGSASNLQYVTSTAFLL  351

350  LAYSNYLSHAKKVVPCGELTASPSLLRQIAKRQVDYILGDNPMGL[SYMVG]  399
     |.|.||||.  ..||. |...: | :||:|||||||:|| :|||||
352  LYYANYLNSSGGHASCGTTTVTAKNLISLAKKQVDYILGQNPAKMSYMVG  401

400  [YGQKFPRRIHHR]GSSVPSVSAHPSHIGCKEGSRYFLSPNPNPNLLVGAVV  449
     :|:::|.:::||||||:||| .||. |.|..| .|:.|. ||||:||||::
402  FGERTPQHVHHRGSSLPSVQVHPNSIPCNAGFQYLYSSPPNPNILVGAIL  451

450  GGP[NVTD]AFPDSRPYFQQSEPTTYINAPLVGLLGYFSAHST   490
     |||:  |.|.|  :|||||.|||||||||  |:::|.|:..
452  GGPDNRDSFSDDRNNYQQSEPATYINAPLVGALAFFAANPV   492
```

FIG.4

```
GTCGACCTGCAGGTCAACGGATCACATGCATCAGCACTATTTACAACAATCCTTTAGGGT    60
ATATGTTAGTCAACCCCGTAACACCATTCGTACCCATTAATCATGAACATTTCGCAAAGT   120
TTTCCCACCAAAAACGGCGTCGGATAAGGTTTTTGGCATTTTGTGTTTCTTTTTTTGTGT   180
GCATAGCATAATTTCATTTTAACCGTACTATTCGAAGATTTTTAAATTGGATAAAGATGA   240
TTCATTCATTACATAGTCGCTTTGTTGTTACTAGTGATAAATTCATGTTAATGATTCTAT   300
GATTTTCGGCCAGCTATCTCATTAATTATTAAGACGTTTAAGTGGAGCTATTAGCAATCG   360
TGTATGACATAATGATTAGCATTTTCATGTGCCATGCCCATGCATGAGGCTTTTTTTTGT   420
TTAAAATTTTATTCTATTATATCCGAATTTTGTTATATACTAAATGAACATTTGTCTCTG   480
ATTTGGTCTACTAGTTAATTAACCTTTAGCTTCACTAATAAAAAATCTCATGATTTTGAT   540
ACTTAAACCCAAAACATATTAAAAACAATTAGCAGTCTTTTAAATCGATAATGTGCTTAG   600
ATGATTATACGTTCGTAGGAAACTCTTTTGTTTCCAATGCATGTTAAGAACTAAGAACTC   660
GTATCCTTAAGCACCAATGCTTTATGCTTAATGCCTCATTAGAGATATAAACTGAGATTG   720
ACTGTGTTCTGAATCATCATAATATAAGGCACACAAAGAACAGAACAGGAAATACTTAGC   780
AATATAATAGGTTTCCAATAAAAGTGAAGAAGAATACAATAAACTTTTATAAAAAAAAAA   840
GTATATAATAATTTCACACTCGAATCAACCAAATGTAAGATGTCTTGTCCATTTACACAT   900
CACATGAGTAAGTGGATTACAGATTGCAATTGATGAAATCTGGATCTTAGCTAAAAATTT   960
ATTACGTTACTATATACATCGAGTTTTAAGATGTTCATAATCACAACCACAACCACAAGT  1020
TTGAAGAAATAAGAAACAGAGTAATAATATATCAAATAAAATTTCATGGCTGATGGAATC  1080
TTTTTTCTAATTGTAGGTCCAAAAAAGCCTAAATTAATGGGGAAACAAAAACCAAAATTC  1140
AATAGTAATTTTACTAATTATGTCTTGGTTAAATAGAGTAAAAAGAAAATTAATCACAAA  1200
CCTCCAAAAATCAACTAATTGAGATCAAAACACGTGTCGCATGCCAATAGGGCGGTGGAT  1260
CACATGGTAAAAAAATTCACTTTAATTTTTGTCTTTCTTCATAATTCATCTCACAGATTT  1320
CAACTTCTCTTTTGGATTCTCTCACCGTACACCGTCGGCGTACCACTCCCCTTCCACACC  1380
GTCGGTATTAAAAATCTCAAACCCTAAAACCCGTATCCAATAACCCACCCGGTCCAACCG  1440
GTTATTCAAACCCGGTCAATCCAAAATTCGCCTCGGAATCCAAACCTCCATACCCAATCT  1500
AACATGGAAAAACCTCCAATCACAAACCTCCACGTGGTGATCACTCATTGGCTCTTATTC  1560
TGGAATCCAAGAGGACCTTTTTAGTATAAAGAGCCCCTTCGTTGGTCCTATCACCTTCTC  1620
TCTCTCACACACTAACAGAAAGCACAAGAAAGAAGAGACAAAAGAATGGCGCGAAAATCC  1680
CTAATTTTCCCGGTGATTTTGCTCGCCGTTCTTCTCTTCTCTCCGCCGATTTACTCCGCC  1740
GGTCACGATTACCGCGACGCTCTCCGTAAA                                1770
```

FIG.8

*ARABIDOPSIS THALIANA* ENDO-1,4-β-GLUCANASE GENE AND PROMOTER

1. FIELD OF THE INVENTION

The present invention relates generally to plants genetically engineered to display altered structure or morphology. The altered structure or morphology can be associated, for example, with greater biomass, yield, or growth, or larger plants or smaller plants. More particularly, the present invention relates to transgenic plants expressing a cell wall modulation transgene or gene construct that results in a transgenic plant having altered structure or morphology. The cell wall modulation transgene is a gene encoding a cellulose binding protein, a cellulose binding domain or a cell wall modifying protein or enzyme. The invention further relates to transgenic plants having altered structure or morphology expressing a transgene such as a gene encoding an endo-xyloglucan transferase, xyloglucan endotransglycosylase, cellulose synthase or a novel isolated endo-1,4-β-glucanase. The invention also relates to transgenic plants containing a gene construct encoding a secretion signal peptide with a cell wall modulation protein or polypeptide controlled by a constitutive or tissue specific promoter. In one embodiment, the tissue specific promoter is a novel elongating tissue specific promoter of *Arabidopsis thaliana*, i.e., the cel1 promoter. The invention also relates to a novel isolated endoglucanase gene, i.e., the *Arabidopsis thaliana* endo-1,4-β-glucanase gene (cel1), its promoter (cel1 promoter) and its encoded polypeptide (Cel1) and recombinant vectors containing the cel1 gene with or without a secretion signal peptide sequence and/or the cel1 promoter.

2. BACKGROUND OF THE INVENTION
2.1. PLANT ELONGATION AND GROWTH

The plant cell elongation mechanism is a fundamental process with primary importance in plant-tissue development. Cell elongation requires relaxation of the rigid primary cell wall (Carpita and Gibeaut, 1993, Plant J. 3:1–30; Cosgrove, 1993, Plant Physiol. 102:1–6; Fry, 1988, *The Growing Plant Cell Wall Chemical and Metabolic Analysis*, Lonoman Scientific & Technical, New York; Roberts, 1994, Curr. Opin. Cell Biol. 6:688–694). Several mechanisms for this relaxation have been suggested, including the activities of endo-xyloglucan transferase (Nishitani and Tominaga, 1992, J. Biol. Chem. 267:21058–21064), xyloglucan endotransglycosylase (Fry et al., 1992, Biochem. J. 282:821–828) and expansins (McQueen-Mason and Cosgrove, 1995, Plant Physiol. 107:87–100). Endo-1,4-β-glucanase (hereinafter, EGase) has been suggested to play an important role in the elongation process (Shoseyov and Dekel-Reichenbach, 1992, Acta Hort. 329:225–227; Verma et al., 1975, J. Biol. Chem.250:1019–1026).

Substantial evidence for the involvement of a 1,3–1,4-β-glucan-specific enzyme in cell elongation was found in monocotyledons (Hatfield and Nevins, 1987, Plant Physiol. 83:203–207; Hoson and Nevins, 1989, Plant Physiol. 90:1353–1358 1989; Inouhe and Nevins, 1991, Plant Physiol. 96:426–431). EGase has been implicated in xyloglucan degradation during vegetative growth and fruit ripening (Hayashi, 1989, Ann. Rev. Plant Physiol. 40:139–168; Hayashi et al., 1984, Plant Physiol. 25:605–610). The activity of this enzyme could affect the generation of oligosaccharins, signaling molecules that are involved, among other things, in plant development and cell elongation (see for review, Darvill et al., 1992, Glycobiology 2:181–198).

To date, most of the EGase genes isolated have been studied in relation to fruit ripening (Cass et al., 1990, Mol. Gen. Genet. 223:76–86; Fischer and Bennett, 1991, Ann. Rev. Plant Physiol. Plant Mol. Biol. 42:675–703; Lashbrook et al., 1994, Plant Cell 6:1485–1493; Tucker et al., 1987, Plant Mol. Biol. 9:197–203) and abscission zones (Kemmerer and Tucker, 1994, Plant Physiol. 104:557–562; Tucker and Milligan, 1991, Plant Physiol. 95:928–933; Tucker et al., 1988, Plant Physiol. 88:1257–1262).

More recently, Wu et al. (1996, Plant Physiol. 110:163–170) cloned the EGase gene from pea and showed its expression to be induced by auxin in elongating epicotyls.

Endogenous regulation of cell elongation appears to be dominated by cell wall mechanics. This process is a result of the interaction between internal turgor pressure and the mechanical strength of the cell wall (reviewed by Steer and Steer, 1989, New Phytol. 111:323–358). Unlike most plant cells, the growth of pollen tubes and root hairs is restricted to the tip zone (reviewed by Cresti and Tiezzi, 1992, "Pollen tube emission organization and tip growth," in *Sexual Plant Reproduction*, pp. 89–97, eds. Cresti and Tiezzi, Springer-Verlag, Berlin). The growing region of pollen tubes consists of two distinct layers when fully mature. The inner layer consists mostly of callose-related molecules and the outer layer contains pectin, xyloglucan (XG), cellulose (at low levels and poor crystallinity) and other polysaccharides (reviewed by Steer and Steer, 1989, New Phytol. 111:323–358).

Xyloglucans (XGs) are linear chains of β-(1–4)-D-glucan, but unlike cellulose, they possess numerous xylosyl units added at regular sites to the 0–6 position of the glucosyl units of the chain (reviewed by Carpita and Gibeaut, 1993, Plant J. 3:1–30). XG can be extracted by alkaline treatment and then bound again in vitro to cellulose (Hayashi et al., 1994, Plant Cell Physiol. 35:1199–1205).

XG is bound to cellulose microfibrils in the cell walls of all dicotyledons and some monocotyledons (reviewed by Roberts, 1994, Curr. Opin. Cell Biol. 6:688–694). The XG bound to the cellulose microfibrils cross-links the cell-wall framework.

Plant-cell expansion, including elongation, requires the integration of local wall-loosening and the controlled deposition of new wall materials. Fry et al. (1992, Biochem J. 282:821–828) and Nishitani and Tominaga (1992, J. Biol. Chem 267:21058–21064) purified xyloglucan endotransglycosylase (XET) and endo-xyloglucan transferase (EXT), respectively. These two enzymes were shown to be responsible for the transfer of intermicrofibrillar XG from one segment to another XG molecule and thus, suggested to be wall loosening-enzymes.

However, McQueen-Mason et al. (1993, Planta 190:327–331) showed that XET activity did not correlate with in vitro cell all extension in cucumber hypocotyls.

The effect of XG on growing tissues has been extensively investigated. XG oligosaccharides, produced by partial digestion with β-(1–4)-D-glucanase and referred to as "oligosaccharins", alter plant-cell growth (reviewed by ldington and Fry, 1993, Advances in Botanical Research 19:1–101). One such oligosaccharin, XXFG (XG9), antagonizes the growth promotion induced in pea stem segments by the auxin 2,4-D at a concentration of about 1 nM (York et al., 1984, Plant Physiol. 75:295–297; McDougall and Fry, 1988, Planta 175:412–416). On the other hand, at high concentrations (e.g.,., 100 μM) oligosaccharins promote the elongation of etiolated pea stem segments (McDougall and Fry, 1990, Plant Physiol. 93:1042–1048). The mode of action of oligosaccharins is still unknown.

Another type of cell wall-loosening protein, termed "expansin", was isolated by McQueen-Mason et al. (1992, The Plant Cell 4:1425–1433). Expansin does not exhibit hydrolytic activity with any of the cell-wall components. It binds at the interface between cellulose microfibrils and matrix polysaccharides in the cell wall, and is suggested to induce cell wall expansion by reversibly disrupting noncovalent bonds within this polymeric network (McQueen-Mason and Cosgrove, 1995, Plant Physiol. 107:87–100).

Some cellulose-binding organic substances alter cell growth and cellulose-microfibril assembly in vivo. Direct dyes, carboxymethyl cellulose (CMC) and fluorescent brightening agents (FBAs, e.g., calcofluor white ST) prevent *Acetobacter xylinum* microfibril crystallization, thereby enhancing polymerization. These molecules bind to the polysaccharide chains immediately after their extrusion from the cell surface, preventing normal assembly of microfibrils and cell walls (Haigler, 1991, "Relationship between polymerization and crystallization in microfibril biogenesis," in *Biosynthesis and Biodegradation of Cellulose*, pp. 99–124, Haigler and Weimer eds., Marcel Dekker, Inc., New York). Haigler discusses dyes and fluorescent brightening agents that bind to cellulose alter cellulose microfibril assembly in vivo. Modifications in cell shape were observed when red alga (Waaland and Waaland, 1975, Planta 126:127–138) and root tips (Hughes and McCully, 1975, Stain Technology 50:319–329) were grown in the presence of dyes. It is now evident that these molecules can bind to the cellulose chains immediately upon their extrusion from the cell surface of prokaryotes and eukaryotes (Haigler and Brown, 1979 Science 210:903–906; Benziman et al., 1980, Proc. Natl. Acad. Sci. USA 77:6678–6682; Haigler et al., 1980, Science 210:903–906; Brown et al., 1982, Science 218:1141–1142) and prevent crystal-structure formation (Haigler and Chanzy, 1988, J. Ultrastruct. Mol. Struct. Res. 98:299–311). In addition, the rate of cellulose polymerization was shown to increase in the presence of dye (Benziman et al., 1980). Crystallization was proposed to be the bottleneck in this coupled reaction and its prevention to result in accelerated cellulose synthase activity.

2.2. CELLULOSE BINDING PROTEINS AND DOMAINS

Many cellulases and hemicellulases (e.g., xylanases and mannases) have the ability to associate with their substrates. These enzymes typically have a catalytic domain containing the active site for substrate hydrolysis and a carbohydrate-binding domain or cellulose-binding domain (herein generally designated "CBD") for binding the insoluble cellulosic or hemicellulosic matrices.

To date, more than one hundred and twenty cellulose-binding domains (CBDs) have been classified into ten families designated I–X (Tomme et al., 1995, "Cellulose-Binding Domains: Classification and Properties", in *ACS Symposium Series* 618 *Enzymatic Degradation and Insoluble Carbohydrates*, pp. 142–161, Saddler and Penner eds., American Chemical Society, Washington, D.C.) (incorporated herein by reference). Most of the CBDs have been identified from cellulases and xylanases, but some are from other polysaccharides or from non-catalytic proteins. The CBDs identified thus far are from fungi, bacteria and slime molds.

The ten families of CBDs are as follows: family I CBDs are all from fungal β-1,4-glycanases; family II CBDs are found in bacterial hydrolases; family III CBDs are found in β-1,4-glucanases; family IV CBDs primarily have two conserved cysteine residues; family V is represented by a CBD from *Erwinia chysanthemi*; family VI CBDs are primarily from xylanases and nearly all located at the C-terminal end of the protein; family VII is represented by the CBD of *Clostridium thermocellum*; family VIII is represented by the CBD of *Dictyostelium discoidum*; family IX CBDs are all known to be present as tandem repeats at the C-terminal end of thermostable xylanases; and family X is represented by xylanase E from *Pseudomonas florescens* spp. cellulosa. For a detailed description of the CBD families and individual members useful in the present invention, see Table II of Tomme et al. which is incorporated herein by reference.

Shoseyov and Doi (1990, Proc. Natl. Acad. Sci. USA 87:2192–2195) isolated a unique cellulose-binding protein (CbpA) from the cellulase "complex" of the cellulolytic bacterium *Clostridium cellulovorans*. This major subunit of the cellulase complex was found to bind to cellulose, but had no hydrolytic activity, and was essential for the degradation of crystalline cellulose.

The cbpA gene has been cloned and sequenced (Shoseyov et al., 1992, Proc. Natl. Acad. Sci. USA 89:3483–3487). Using PCR primers flanking the cellulose-binding domain (herein, this specific CBD is designated "cbd") of CbpA, the latter was successfully cloned into an overexpression vector that enabled overproduction of the approximately 17 kDa cbd in *Escherichia coli*. The recombinant cbd exhibits very strong affinity to cellulose (U.S. Pat. No. 5,496,934; Goldstein et al., 1993, J. Bacteriol. 175:5762–5768; PCT International Publication WO 94/24158, all are incorporated by reference as if fully set forth herein).

In recent years, several CBDs have been isolated from different sources. Most of these have been isolated from proteins that have separate catalytic, i.e., cellulase and cellulose binding domains, and only two have been isolated from proteins that have no apparent hydrolytic activity but possess cellulose-binding activity (Goldstein et al., 1993, J. Bacteriol. 175:5762–5768; Morag et al., 1995, Appl. Environ. Microbiol. 61–1980–1986).

2.3. CLOSTRIDIUM CELLULOVORANS CBD EFFECTS ON SEEDLING AND POLLEN TUBE ELONGATION

The exogenous application of the cbd of *Clostridium cellulovorans* has been shown to modulate the elongation of pollen tubes and seedlings grown in culture. See PCT International Publication WO 94/24158 at pages 73–77.

The cbd of *C. cellulovorans* promoted pollen tube growth of peach pollen grains grown in liquid culture. Pollen grains exposed to 50 ug/ml of cbd produced pollen tubes almost twice size of pollen grains treated with bovine serum albumin (BSA) at 50 ug/ml.

Seeds of *Arabidopsis thaliana* germinated in distilled water in the presence of *C. cellulovorans* cbd responded differently to high versus low concentrations of cbd. High concentrations of cbd (1–100 ug/ml) dramatically reduced the root length. Low concentrations of cbd ($1\times10^{-6}$ to $1\times10^{-4}$ ug/ml) promoted elongation of the roots whereas treatment with BSA had no effect. The effect on shoot length revealed a similar trend, but the differences between the treatments were not as dramatic as for the roots, and were not statistically different.

Cell walls of pollen tubes have been shown to contain exposed cellulose fibrils in the tip zone (reviewed by Steer and Steer, 1989, New Phytol. 111:323–358). Pollen tube elongation is known to be apical (reviewed by Cresti and Tiezzi, 1992, "Pollen tube emission, organization and tip growth", in *Sexual Plant Reproduction*, pp. 89–97, Cresti and Tiezzi eds., Springer-Verlag, Berlin). Gold-immunolabelling of cbd in pollen tubes revealed that cbd was present primarily at the tip zone. Moreover, the lack of calcofluor staining in the tip zone of cbd-treated pollen tubes indicated the absence of a crystalline structure. See PCT International Publication WO 94/24158.

It has already been established that XG chains cross-link the cellulosic network in the cell wall (reviewed by Roberts, 1994, Curr. Opin. Cell Biol. 6:688–694). It is accepted that a prerequisite for cell elongation is a loosening of the cross-linked cellulose network, by either hydrolysis as demonstrated by Inouhe and Nevins (1991, Plant Physiol. 96:426–431), transglycosylation (Fry et al., 1992, Biochem. J. 282:821–828; Nishitani and Tominaga, 1992, J. Biol. Chem. 267:21058–21064), or expansins that interact with the XG-cellulose bond (McQueen-Mason et al., 1992, The Plant Cell 4:1425–1433). By in vitro competition assays it was shown that cbd competes with XG for binding to cellulose. Maximum cbd binding to cellulose is achieved after 1 hour (Goldstein et al. 1993, J. Bacteriol. 175:5762–5768), compared to XG binding to cellulose that is achieved only after 4 hour (Hayashi et al. 1987, Plant Physiol. 83:384–389). It is suggested that, during the elongation process, cellulose microfibrils become exposed and cbd competes with XG on binding to the exposed cellulose microfibril. It is therefore possible that this competition results in a temporary loosening of the cell wall and consequently enhanced elongation.

The inhibitory effect of cbd on root elongation can be explained by steric hindrance of the cellulose fibrils by excess amounts of cbd, which block access for enzymes or other proteins that modulate cell elongation via loosening, of the rigid cellulose-fibril network. This hypothesis is supported by Nevins, who prevented auxin-induced elongation with anti-β-D-glucan antibodies (Hoson and Nevins, 1989, Plant Physiol. 90:1353–1358) or with antibodies specific to cell wall glucanases (Inouhe and Nevins, 1991, Plant Physiol. 96:426–431).

The cbd of the CbpA protein of *C. cellulovorans* is a bacterial protein. Its mode of action in modulating cell wall elongation may be different from that of the natural process.

3. SUMMARY OF THE INVENTION

The present invention provides the production of transgenic plants which express a transgene or transgenic construct of a plant cell wall modulation protein or polypeptide so that the resulting plants have altered structure or morphology. The present invention particularly provides for altered structure or morphology by expressing a plant cell wall modulation protein or polypeptide such as, but not limited to, a cellulose binding protein, a cellulose binding domain or a cell wall modifying enzyme. In a particularly preferred embodiment, the cell wall modulation protein is a cellulose binding domain (CBD).

According to one embodiment of the present invention, achieving the desired plant of altered structural morphology can entail expression of a plant cell wall modulation protein or peptide under the regulation of a suitable promoter. In one mode of this embodiment, the promoter may be a plant promoter that is tissue- and/or developmental stage-specific. Suitable promoters include such as, an elongating tissue specific promoter (e.g., cel1 promoter), the chalcone synthase promoter (CHS), and the PATATIN promoter from potato. In an alternative mode of this embodiment, the promoter is constitutive and active in all plant tissues, substantially along its entire life cycle (e.g., the cauliflower mosaic virus (CaMV 35S) promoter). However, any combination of promoters and transgenes encoding cell wall modulation proteins and polypeptides is also useful according to the invention.

Also according to the invention, the cell wall modulation transgene may be secreted from the expressing plant cells which is achieved by having the cell wall modulation protein or polypeptide fused to any suitable secretion signal peptide.

The invention further provides seeds of transgenic plants wherein the seed has a plant cell wall modulation transgene or gene construct. The invention also encompasses progeny, clones, cell lines or cells of transgenic plants having a plant cell wall modulation transgene or gene construct.

According to further features of the invention, a novel endo-β-1,4-glucanase (EGase) gene (cel1) and protein (Cel1) from *Arabidopsis thaliana* is provided. Also provided is an elongating tissue specific promoter (cel1 promoter) of the *A. thaliana* EGase gene or functional fragment thereof.

According to still further features of the present invention, isolated nucleic acid molecules encoding proteins or polypeptides having the amino acid sequence of the Arabidopsis cel1 of SEQ ID NO:4 or variants thereof are provided. In particular, an isolated nucleic acid molecule having the sequence of SEQ ID NO:2 is provided.

An isolated nucleic acid molecule comprising the genomic clone of the Arabidopsis endo-1,4-β-glucanase gene having the nucleotide sequence of SEQ ID NO:9 is also provided.

According to still further features exemplified by specific embodiments, a polypeptide which includes an amino acid sequence corresponding to *Arabidopsis thaliana* cel1 gene, as well as allelic and species variants, and functional naturally occurring and man-made variants thereof are provided. The present invention also provides derivatives or analogs of the Arabidopsis Cel1 polypeptide.

Further, the present invention provides for nucleotide vectors containing the above nucleotide sequences and host cells containing the recombinant nucleic acid vectors.

According to still further features, a polypeptide comprising the amino acid sequence of the Arabidopsis endo-1,4-β-glucanase (cel1) gene, allelic and species variants, and naturally occurring and man-made functional variants, derivatives and analogs thereof are provided. In addition, the proteins having endo-1,4-β-glucanase activity or the ability to bind cellulose or hemicellulose may have a non-naturally occurring amino acid sequence. A nucleic acid sequence encoding the latter may be derived from a random display library, using, for example, cellulose as a screening agent.

The present invention further relates to recombinant nucleic acid vectors comprising a first nucleic acid sequence encoding a secretion signal peptide and second nucleic acid sequence encoding a cell wall modulation protein or polypeptide. In more specific embodiments, the cell wall modulation proteins or polypeptides are selected from cellulose binding proteins, cellulose binding domains and cell wall modifying enzymes.

The invention is based in part, on a number of unanticipated surprising discoveries. One is the discovery that expressing a cellulose binding protein or a cellulose binding domain (CBD) in transgenic plants results in transgenic plants having altered structural morphology. The other is the finding that expressing the *Arabidopsis thaliana* endo-1,4-β-glucanase in transgenic plants also results in plants having altered structural morphology. These findings together indicate that expressing a cell wall modulation transgene in plants results in plants having altered structure or morphology.

It is an object of the invention to express any CBD in a transgenic plant to alter plant morphology, e.g. to stimulate or inhibit growth. In one embodiment, it is an object of the invention to express any CBD, under the control of the cel1 promoter, with the cell signal peptide to target the CBD to the cell wall thus resulting in tissue specific growth modulation.

The invention has utility in producing plants with altered structure or morphology. Such altered structure or morphology provides plants that have an improved rate of growth, a greater or less biomass, plants more or less resistant to biodegradation, plants more or less digestible to ruminant animals, plants with modified fibers, or plants with altered cellulose content.

The cel1 gene of the invention has utility as a transgene encoding cell wall modulation protein or polypeptide in a transgenic plant to alter the structure or morphology. The cel1 promoter of the present invention may be utilized as an elongating tissue specific plant promoter to express any protein, polypeptide or peptide of interest in a tissue specific manner in a transgenic plant. The *Arabidopsis thaliana* Cel1 protein of the invention can be used in any biochemical applications. The Cel1 secretion peptide of the invention may be utilized to facilitate the cellular secretion of any protein, polypeptide or peptide of interest.

3.1. DEFINITIONS

The term "altered structure or morphology" as used herein refers to any microscopic or macroscopic change in structure or morphology of the transgenic plant when compared to a progenitor plant cultivated under the same conditions. The altered structure or morphology can be associated, for example, with altered biomass, growth, yield, greater or less resistance to biodegradation, more or less digestible to reuminants, altered cellulose content, larger leaves/normal hypocotyls or smaller leaves/longer hypocotyls, etc. compared to a non-transgenic plant of the species.

The terms "protein", "polypeptide" and "peptide" are used interchangeably throughout the specification and claims. These terms also encompass glycosylated proteins, i.e., glycoproteins.

The term "cell wall modulation" as used herein refers to any alteration from a normal growth pattern of a plant. Therefore, according to the present invention, transgenic expression of a cell wall modulation protein or polypeptide results in altered plant structure or morphology.

The term "cellulose binding protein" refers to any protein, polypeptide or peptide including a glycoprotein, which specifically binds to cellulose or hemicellulose. The cellulose binding protein may or may not have cellulose or cellulolytic activity. The term "cellulose binding domain" (CBD) refers to any protein, polypeptide or peptide, including a glycoprotein, which is a region or portion of a larger protein, said region or portion which binds specifically to cellulose or hemicellulose. The cellulose binding domain (CBD) may be a part or portion of a cellulose, xylanse or other polysaccharidase, e.g. a chitinase, etc., a sugar binding protein such as maltose binding protein, etc., or a non-catalytic polysaccharide binding protein.

To date, more than one hundred and twenty cellulose-binding domains (CBDs) have been classified into ten families designated I-X (Tomme et al., 1995, "Cellulose-Binding Domains: Classification and Properties", in *ACS Symposium Series* 618 *Enzymatic Degradation and Insoluble Carbohydrates*, pp. 142–161, Saddler and Penner eds., American Chemical Society, Washington, D.C.) (incorporated herein by reference). Any of the CBDs described in Tomme or any variants thereof, any other presently known CBDs or any new CBDs which may be identified can be used in the present invention. In addition, the CBD may be selected from a phage display peptide or peptidomimetic library, random or otherwise, using cellulose as a screening agent. (See Smith, 1985, Science 228:1315–1317 and Lam, 1991, Nature 354:82–84). Further, the CBD may be derived by mutation of a portion of a protein, polypeptide or peptide, including a glycoprotein, which binds to a polysaccharide other than cellulose (or hemicellulose), such as a chitinase, which specifically binds chitin, or a sugar binding protein such as maltose binding protein, rendering said portion capable of binding to cellulose. In any event, the CBD binds cellulose or hemicellulose.

4. BRIEF DESCRIPTION OF THE DRAWINGS

FIG. 1 shows PCR products resolved on an agarose gel. Lane A: PCR products. The 260 bp fragment was used for further characterization. M: ladder DNA size marker of x 123 base pairs (bp) (Gibco BRL).

FIG. 2 is a schematic depiction of the *Arabidopsis thaliana* cel1 genomic gene (SEQ ID NO:9) showing its DNA structure and restriction map. EcoRI-RI, EcoRV-R, NcoI-N, SalI-S, SphI-Sp, XhoI-X. The transcribed region is boxed. Exons—striped boxes. Introns—open boxes. 5' and 3' untranslated regions—shaded boxes. The three lines below the map indicate subclones used for ExoIII deletions. Numbers refer to nucleotides in SEQ ID NO:9. The extent of the 5' and 3' untranslated regions was not determined and is therefore indicated with question mark.

FIG. 3 shows PCR amplification of a full-length reverse transcribed *A. thaliana* cel1 cDNA (nucleotides 1–1479, SEQ ID NO:2). Lane A: the cDNA fragment. Lane B: control, PCR reaction performed on total mRNA which has not been pretreated with reverse transcriptase. M: 1 kb ladder DNA size marker (Gibco BRL).

FIG. 4 presents an optimal alignment of the deduced amino-acid sequences encoded by *A. thaliana* cel1 (top, amino acids 2–490, SEQ ID NOs:3 and 4) and avocado cel1 (bottom, amino acids 5–492, SEQ ID NO:8). Aligned cysteine residues are underlined. The potential glycosylation site (Asn-X-Ser/Thr) in Cel1 is boxed. The glycosyl hydrolase motif is both under- and abovelined.

FIG. 5 presents a Kyte-Doolittle hydropathy analysis of the *A. thaliana* Cel1 protein (top), as compared to the avocado EGase (Cel1, bottom).

FIG. 6 presents a northern blot analysis of cel1. Lane 1: fully expanded leaf; Lane 2: the basal internode of the flowering stem; Lane 3: elongating zone in the flowering stem of a normal plant; Lane 4: elongating zone in the flowering stem of a dwarf plant (treated with uniconazole). The bottom lanes represent rRNA as internal standards.

FIGS. 7A–C present histological glucuronidase (GUS) staining of transgenic tobacco transformed with the cel1 promoter region (nucleotides 5–1618, SEQ ID NO:1) fused to the gus reporter gene. FIG. 7A. The arrows are pointed to the blue stained elongating zones at the shoot and the root. FIG. 7B. enlarged shoot apex. FIG. 7C. enlarged root tip.

FIG. 8 shows the nucleic acid sequence of the *A. thaliana* promoter region of cel1 (nucleotides 1–1770, SEQ ID NO: 1). The conserved promoter motifs TATA, CAT (x 2) and GC, and the translation initiator AUG codon are underlined.

FIG. 9 shows PCR amplification of genomic DNA of transgenic plants. The 500 bp band is indicative of the presence of a cbd transgene. Lanes 1 and 2: p35SC1.1 and p35SC1.2 transgenic plant clones. Lanes 3 and 4: pCC1.1 and pCC1.2 transgenic plant clones. Lanes 5 and 6: pBI101.1 and pBI101.2 transgenic plant clones. Lane 7: non transgenic plant. Lane 8: positive control—p35SC1 DNA. M: 1 kb ladder DNA size marker (Gibco BRL).

FIG. 10 shows (in negative) PCR amplification of reverse transcribed cDNA (RT-PCR) obtained from transgenic plants. The 500 bp band is indicative of the expression of a cbd transgene. Lane 1: positive control—p35SC1 DNA. Lane 2: negative control no reverse transcription. Lane 3: pBI101.1 transgenic plant clone. Lanes 4 and 5: p35SC1.1 (small phenotype) and p35SC1.2 (large phenotype) transgenic plant clones. M: 1 kb ladder (Gibco BRL).

FIGS. 11A-B are photographs of germination plates containing fourteen day old (A) tobacco plants derived from $F_1$ seeds obtained by selfing a pBI101 transgenic plant clone; and (B) tobacco plants derived from $F_1$ seeds obtained by selfing a p35SC1 transgenic plant clone.

FIGS. 12A-B are top and side photographs of eight week old $F_1$ p35SC1 tobacco plants demonstrating a large (left) and a small (right) phenotype. The plants were transferred from the germination plate after four weeks.

FIGS. 13A-B are photographs of germination plates containing four weeks vegetatively propagated $F_1$ p35SC1 transgenic plant clones of the large (A) and small (B) phenotypes.

FIGS. 14A-B are top and side photographs of ten week old vegetatively propagated $F_1$ p35SC1 tobacco plants demonstrating the large (right) and small (left) phenotypes.

FIG. 15A–F graphically shows a comparison of the biomass production of transgenic tobacco plants transformed with plasmid (p35SC1) compared to the control plants transformed with plasmid (pBI121) having either large phenotype (large leaves/normal hypocotyl) (FIG. 15A–C) or small phenotype (small leaves/long hypocotyl) (FIG. 15D–F). Measurements were taken of wet weight (FIG. 15A and D), dry weight (FIG. 15B and E) and leaf area (FIG. 15C and F).

FIG. 16A-B graphically show a comparison of the biomass production of transgenic tobacco plants expressing cbd under the cel1 promoter in plasmid pCC1 (pCC15.5) and wild type tobacco plants (wild). Measurements of weight (16A) and leaf area (16B) were taken.

Figure 31:
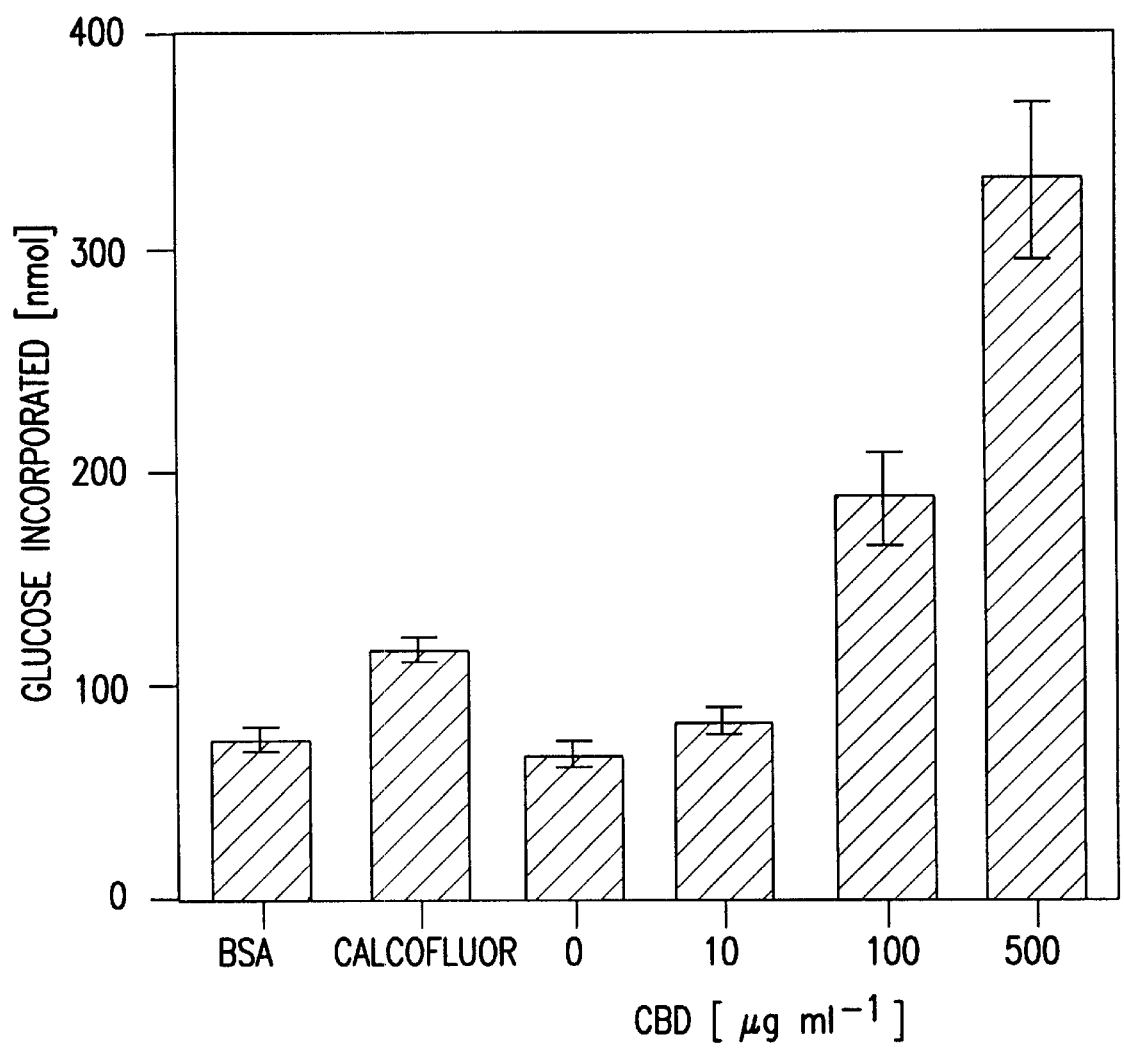

FIG. 31 is a graph depicting the effect of different concentrations of cbd on cellulose synthase activity as measured by the amount of glucose incorporation (nmol) in *Acetobacter xylinum*. The cbd concentrations listed were 0, 10, 100 and 50 mg/ml as compared to calcofluor and the control (BSA). Bars represent standard error.

Figure 32A:
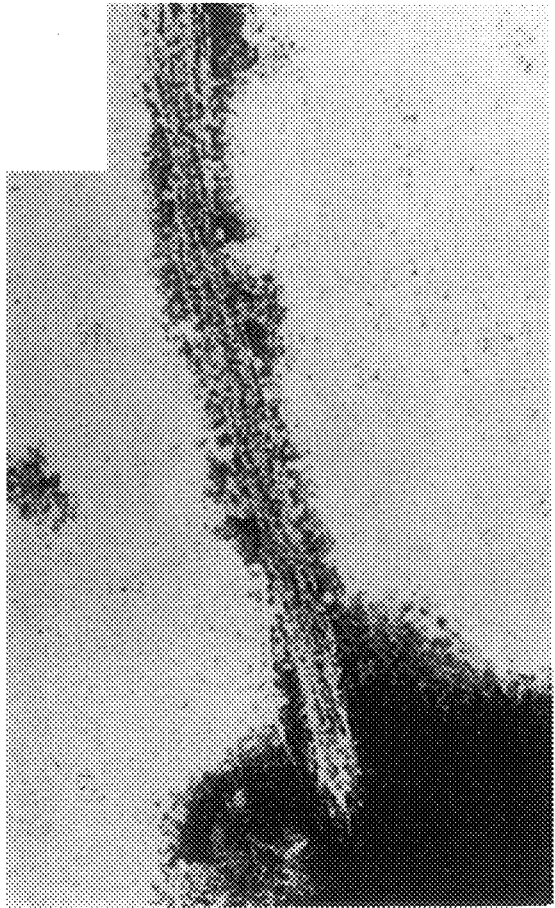
Figure 32B:
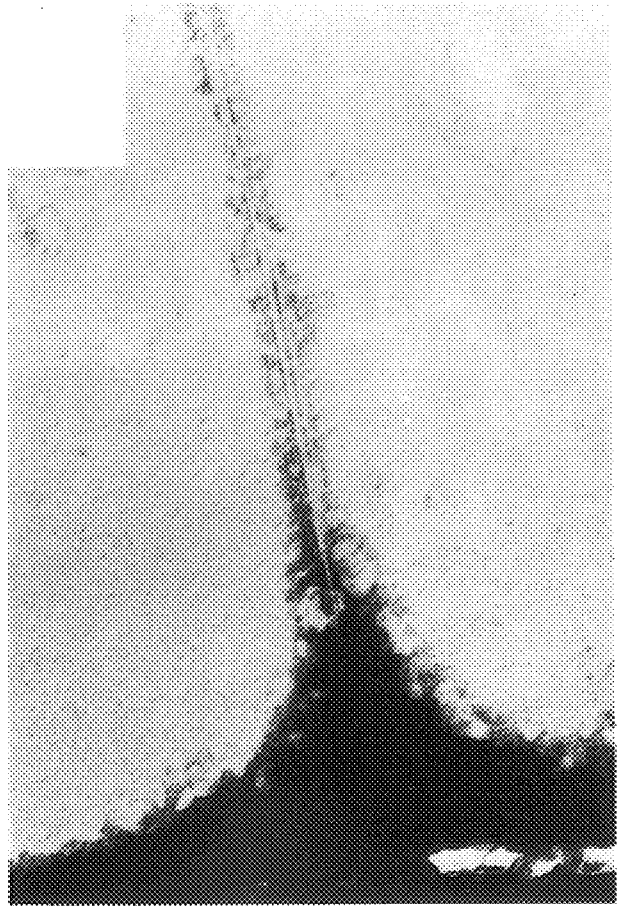

FIGS. 32A-B are photographs of an electron microscopy examination of the effect of cbd on the type of cellulose ribbon produced by *Acetobacter xylinum* with cbd(A) or a control without cbd(B).

5. DETAILED DESCRIPTION OF THE INVENTION

The present invention provides the production of transgenic plants which express a transgene or transgenic construct of a plant cell wall modulation protein or polypeptide so that the resulting plants have altered structure or morphology. The present invention particularly provides for altered structure or morphology by expressing a plant cell wall modulation protein or polypeptide such as, but not limited to, a cellulose binding protein, a cellulose binding domain or a cell wall modifying enzyme. In a particularly preferred embodiment, the transgenic plants express a cellulose binding domain. Any cellulose binding domain is advantageously used in this preferred embodiment.

Without intending to be limited to a particular mechanism, the inventors note that the targets for engineering are genes encoding proteins or enzymes involved in the synthesis and/or rearrangement and/or degradation of cellulose in the plant cell wall.

The proteins, polypeptides or enzymes can be expressed to engineer a plant with desirable properties. The engineering is accomplished by transforming plants with nucleic acid constructs described herein which may also comprise promoters and secretion signal peptides. The transformed plants or their progenies are screened for plants that express the desired protein, polypeptide or enzyme.

Engineered plants exhibiting the desired altered structure or morphology can be used in plant breeding or directly in agricultural production or industrial applications. Plants having one altered enzyme, protein or polypeptide can be crossed with other altered plants engineered with alterations in other growth modulation enzymes, proteins or polypeptides to produce lines with even further enhanced altered structural morphology characteristics compared to the parents or progenitor plants.

In another aspect, the present invention provides isolated nucleic acids encoding the *Arabidopsis thaliana* endo-1,4-β-glucanase (cel1), the cel1 promoter and the Cel1 protein. The invention also provides isolated nucleic acid molecules comprising the genomic sequence of the *Arabidopsis* thaliana cel1 gene encoded by the nucleotide sequence of SEQ ID NO:9. The present invention further provides nucleic acid molecules encoding proteins or polypeptides having the amino acid sequence of the *A. thaliana* Cel1 of SEQ ID No:4, as well as variants, derivatives or analogs thereof. The invention further provides nucleic acid vectors containing the described nucleic acid molecules and host cells containing the recombinant nucleic acid vectors. Uses of the *A. thaliana* cel1 nucleic acid and Cel1 amino acid sequences are also provided.

Solely for ease of explanation, the description of the invention is divided into the following sections: (A) transgenic plants expressing a cell wall modulation protein; (B) methods for generating transgenic plants, including (i) preparation of nucleic acid constructs, including optimal expression nucleic acid constructs; (ii) transformation of plants and plant cells; (iii) selection and identification of transformed plants and plant cells; (C) identification and isolation of a novel endo-1,4-β-glucanase gene of *A. thaliana* (cel1)useful to express a cell wall modification protein in the transgenic plants and (D) applications of or uses for the transgenic plants and the novel *A. thaliana* endo-1,4-β-glucanase cel1 gene, the cel1 signal sequence, the cel1 promoter and Cel1 protein and polypeptide equivalents. The description of the novel *A. thaliana* endo-1,4-β-glucanase gene also includes a description of the protein encoded, the cel1 signal sequence and the cel1 promoter, which itself is also useful as an elongating tissue specific promoter for the transgenic plants of the invention.

5.1. TRANSGENIC PLANTS

The present invention encompasses transgenic plants comprising a transgene that directs the expression of a cell modulation protein or polypeptide, and the transgenic plant exhibits altered structure or morphology compared with a progenitor plant which does not contain the transgene, when the transgenic plant and the progenitor plant are cultivated under similar or equivalent growth conditions. The cell wall modulation transgene is a gene encoding a cellulose binding protein, a cellulose binding domain or cell wall modifying enzyme. According to a preferred embodiment, the cell wall modulation transgene is a gene encoding a cellulose binding domain. Any cellulose binding domain, as defined herein, can be used. For an illustrative, but in no way limiting example, a cellulose binding domain is obtainable from a bacterial, fungal or slime mold protein or polypeptide. For a more particular illustrative example, a cellulose binding domain is obtainable from *Clostridium cellulovorans, Clostridium thermocellum* or *Cellulomonas fimi* (e.g., CenA, CenB, CenD, Cex). Illustrative working examples of transgenic plants expressing a cellulose binding domain are presented infra herein in Sections 13, 15 and 18.

The cell wall modulation protein employed may be of any type. For example, the protein may be a higher plant protein known to be associated with plant growth elongation, such as, but not limited to, an endo-1,4-β-glucanase (EGase), endo-xyloglucan transferase, xyloglucan endotransglycosylase, cellulose synthase, and expansin. In a specific embodiment, the EGase is a novel EGase, i.e. Cel1. In other specific embodiments, the EGase is obtainable from tomato or avocado.

However, the protein may alternatively be a bacterial, a fungal or a slime mold protein which modulates plant growth.

It is shown in the illustrative working examples herein that transgenic plants expressing *Clostridium cellulovorans* CBD are growth modulated in strong correlation with their genotype (i.e., homozygote or heterozygote).

The transgene may be selectively expressed in some tissues of the plant or at some developmental stages, or the transgene may be expressed in substantially all plant tissues, substantially along its entire life cycle. However, any combinatorial expression mode is also applicable.

In another specific embodiment, the transgenic plant comprises a cell wall modulation protein or polypeptide which is an endo-1,4-β-glucanase. In a more specific embodiment, the EGase is obtainable from *Arabidopsis thaliana*. (See infra Section 5.3).

The present invention also encompasses transgenic plants having a gene construct comprising a transgene encoding a cell wall modulation polypeptide operably linked to a promoter so that the cell wall modulation polypeptide is expressed in the transgenic plant, and the transgenic plant exhibits altered structure or morphology compared with a progenitor plant which does not contain the gene construct when the transgenic plant and progenitor plant are cultivated under similar conditions.

In a specific embodiment, the promotor is a constitutive plant promoter. In a more specific embodiment, the plant promoter is the CaMV 35S promoter.

In another specific embodiment, the promoter is a tissue specific plant promoter. In a more specific embodiment, the plant promoter is the elongating tissue specific cel1 promoter (see infra Section 5.3).

In another specific embodiment, the plant promoter is a development-specific promoter such as a seed specific, fruit specific, ripening specific, flowering specific promoter, etc.

In a preferred embodiment, the transgenic plant comprises the gene construct of the cel1 promoter and Cel1 encoding nucleic acid.

In another preferred embodiment, the transgenic plant comprises the gene construct of the cel1 promoter and a CBD encoding nucleic acid.

In yet another preferred embodiment, the transgenic plant contains a gene construct which further includes a secretion signal peptide, more particularly, the cel1 secretion signal peptide.

The present invention also encompasses seeds of the transgenic plants described above wherein the seed has the transgene or gene construct.

The present invention further encompasses the progeny, clones, cell lines or cells of the transgenic plants described above wherein said progeny, clone, cell line or cell has the transgene or gene construct.

5.2. GENERATING TRANSGENIC PLANTS 5.2.1. NUCLEIC ACID CONSTRUCTS

The properties of the nucleic acid sequences are varied as are the genetic structures of various potential host plant cells. This description of exemplary embodiments of the present invention includes a number of features which an artisan may recognize as not being absolutely essential, but clearly advantageous. These include methods of isolation, synthesis or construction of gene constructs, the manipulations of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present invention, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The nucleic acid constructs described herein can be produced using methods well known to those skilled in the art. Artisans can refer to sources like Sambrook et al., 1989, *Molecular Cloning: A Laboratory Manual*, Cold Spring Harbor Laboratory Press, New York for teachings of recombinant DNA methods that can be used to isolate, characterize, and manipulate the components of the constructs as well as to build the constructs themselves. In some instances, where the nucleic acid sequence of a desired component is known, it may be advantageous to synthesize it rather than isolating it from a biological source. In such instances, an artisan can refer to teachings of references such as Caruthers et al., 1980, Nuc. Acids Res. Symp. Ser. 7:215–233, and Chow and Kempe, 1981, Nuc. Acids Res. 9:2807–2817. In other instances, the desired components may be advantageously produced by polymerase chain reaction (PCR) amplification. For PCR teachings, an artisan can refer to the references such as Gelfand, 1989, *PCR Technology, Principles and Applications for DNA Amplification*, H. A. Erlich ed., Stockton Press, New York, 1988, *Current Protocols In Molecular Biology*, Vol. 2, Ch. 15, Ausubel et al. eds., John Wiley & Sons.

5.2.1.1. EXPRESSION CONSTRUCTS

In accord with the present invention, a transgenic plant with the ability to express a plant cell wall modulation polypeptide may be engineered by transforming a plant cell with a gene construct comprising a sequence encoding a plant cell wall modulation protein or polypeptide. In one embodiment, a plant promoter is operably associated with a sequence encoding the desired plant cell wall modulation protein or polypeptide. ("Operably associated" or "operably linked" is used herein to mean that transcription controlled by the "associated" or "operably linked" promoter produces a functional messenger RNA, whose translation produces the polypeptide.) In a preferred embodiment of the present invention, the associated promoter is a strong and non tissue- or developmental-specific plant promoter (e.g., a promoter that strongly expresses in many or all plant tissue types). Examples of such strong, "constitutive" promoters include, but are not limited to, the CaMV 35S promoter, the T-DNA mannopine synthetase promoter, and their various derivatives.

In another embodiment of the present invention, it may be advantageous to engineer a plant with a gene construct comprising a sequence encoding a plant cell wall modulation protein or polypeptide operably associated with a tissue- or developmental-specific promoter, such as, but not limited to the cel1 promoter, the CHS promoter, the PATATIN promoter, etc. For example, where expression in elongating tissues and organs is desired, promoters such as the cel1 promoter may be used.

In yet another embodiment of the present invention, it may be advantageous to transform a plant with a gene construct comprising a sequence encoding a plant cell wall modulation protein or polypeptide operably linked to a modified or artificial promoter. Typically, such promoters, constructed by recombining structural elements of different promoters, have unique expression patterns and/or levels not found in natural promoters. See e.g., Salina et al., 1992, Plant Cell 4:1485–1493, for examples of artificial promoters constructed from combining cis-regulatory elements with a promoter core.

In yet an additional embodiment of the present invention, the expression of a cell wall modulation gene may be engineered by increasing the copy number of the gene encoding the desired protein or polypeptide. One approach to producing a plant cell with increased copies of the desired gene is to transform with nucleic acid constructs that contain multiple copies of the gene. Alternatively, a gene encoding the desired polypeptide can be placed in a nucleic acid construct containing an amplification-selectable marker (ASM) gene such as the glutamine synthetase (GS) or dihydrofolate reductase gene. Cells transformed with such constructs are subjected to culturing regimes that select cell lines with increased copies of ASM gene. See Donn et al., 1984, J. Mol. Appl. Genet. 2:549–562, for a selection protocol used to isolate of a plant cell line containing amplified copies of the GS gene. Because the desired gene is closely linked to the ASM gene, cell lines that amplified the ASM gene would also likely to have amplified the gene encoding the desired growth modulation polypeptide.

In still another embodiment of the present invention, the expression of a cell wall modulation protein or polypeptide may be engineered by transforming a plant cell with a nucleic acid construct encoding a regulatory gene that controls the expression of the endogenous gene or a transgene encoding the desired polypeptide, wherein the introduced regulatory gene is modified to allow for strong expression of the polypeptide in the desired tissues and/or developmental stages.

5.2.1.2. OTHER FEATURES OF RECOMBINANT NUCLEIC ACID CONSTRUCTS

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding β-glucuronidase (Jefferson, 1987, Plant Molec Biol. Rep 5:387–405), luciferase (Ow et al., 1986, Science 234:856–859), and the B and C1 gene products that regulate anthocyanin pigment production (Goff et al., 1990, EMBO J 9:2517–2522).

In embodiments of the present invention which utilize the Agrobacterium system for transforming plants (see infra), the recombinant DNA constructs additionally comprise at least the right T-DNA border sequence flanking the DNA sequences to be transformed into plant cell. In preferred embodiments, the sequences to be transferred in flanked by the right and left T-DNA border sequences. The proper design and construction of such T-DNA based transformation vectors are well known to those skilled in the art.

5.2.2. TRANSFORMATION OF PLANTS AND PLANT CELLS

According to the present invention, a desirable plant may be obtained by transforming a plant cell with a nucleic acid construct described herein. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, genetic engineering is accomplished by transforming with one gene construct, obtaining the desired transformant after selection and screening, transforming the transformant with a second gene construct, and so on. In certain embodiments, each gene construct is be linked to a different selectable or screenable marker gene so as to facilitate the identification of plant transformants containing multiple gene inserts. In other embodiment, several different genes may be incorporated into one plant by crossing parental lines engineered for each gene.

In an embodiment of the present invention, Agrobacterium is employed to introduce the gene construct into plants. Such transformation preferably uses binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet 16:357–384; Rogers et al., 1986, Methods Enzymol. 118:627–641). The Agrobacterium transformation system may also be used to transform, as well as transfer, DNA to monocotyledonous plants and plant cells. (see Hernalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; and Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; and Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; and Gordon-Kamm et al., 1990, Plant Cell 2:603–618).

According to the present invention, a wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., Arabidopsis).

5.2.3. SELECTION AND IDENTIFICATION OF TRANSFORMED PLANTS AND PLANT CELLS

According to the present invention, desired plants may be obtained by engineering one or more of the disclosed gene constructs into a variety of plant cell types, including but not limited to, protoplasts, tissue culture cells, tissue and organ explants, pollens, embryos as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

5.3. ARABIDOPSIS THALIANA ENDO-1,4-β-GLUCANASE 5.3.1. cel1 GENE, PROMOTER AND RECOMBINANT VECTORS In another aspect, the present invention provides novel isolated nucleic acid molecules containing the nucleotide sequence encoding an endo-1,4-β-glucanase (Cel1) polypeptide of *Arabidopsis thaliana*. In one embodiment, the polypeptide has the amino acid sequence of SEQ ID NO:4.

In a specific embodiment, the isolated nucleic acid molecule has the nucleotide sequence of SEQ ID NO:2.

In another specific embodiment, the isolated nucleic acid molecule encoding a polypeptide having the amino acid sequence of SEQ ID NO: 4 is a variant such as an allelic variant, a species variant, a naturally occurring variant, a man-made or induced variant. The nucleic acid molecule may also encode derivatives or analogs of the polypeptide of SEQ ID NO:4.

As illustrated in the examples, infra, the isolation of the cell gene was effected by PCR amplification of a 260 bp fragment using degenerate primers designed according to conserved amino-acid sequences in avocado and tomato EGases, which was thereafter used to screen an *A. thaliana* genomic library.

A 7.5 kb SAlI fragment (SEQ ID NO:9) hybridizing with the 260 bp PCR fragment was isolated and analyzed. It was found that the *A. thaliana* cel1 gene includes seven exons intercepted by six introns.

The present invention also provides an isolated nucleic acid molecule having the nucleotide sequence of SEQ ID NO:9 which is the *Arabidopsis thaliana* genomic clone of endo-1,4-β-glucanase.

Utilizing the nucleic acid sequence of the exons, RT-PCR was used to test for the presence of cel1 mRNA in elongating tissue and to isolate cel1 cDNA which includes the open reading frame of cel1. A cel1.5 kb cDNA fragment was successfully cloned and sequenced (SEQ ID NO:2). The cDNA sequence perfectly matched the DNA sequence of the combined exons, as deduced from SEQ ID NO:9.

The 1476 by open reading frame of cel1 was found to encode a 492 amino acid polypeptide (SEQ ID NO: 4) with a predicted molecular weight of 54 kDa.

As illustrated in the working examples, infra, northern blot analysis of cel1 was carried out using a 768 by cel1cDNA fragment as a probe. RNA transcripts were undetectable in fully expanded leaves, as well as at the basal internode of flowering stems. However a strong transcript signal was detected in the elongating zone of flowering stems of normal plants.

Transgenic tobacco plants transformed with the putative cel1 promoter region fused to the β-glucuronidase (GUS) reporter gene (gus), were tested for tissue-specific expression.

Significant GUS activity was observed in 16 seedlings that were generated from 8 independent transgenic plants. The staining was observed both in shoot and root elongating zones.

The cel1 nucleic acid molecules of the invention include (a) the DNA sequence shown in SEQ ID NO: 2; (b) any nucleotide sequence that encodes the amino acid sequence shown in SEQ ID NO:4; (c) any nucleotide sequence that hybridizes to the complement of the cDNA sequence shown in SEQ ID NO:2 and encodes a functionally equivalent product; (d) any nucleotide sequence that hybridizes to the complement of the DNA sequences that encode the amino acid sequence shown in SEQ ID NO:3 and encodes a functionally equivalent product; and (e) any nucleotide sequence encoding a plant protein containing the amino acid sequence of the endo-1,4-β-glucanase shown in SEQ ID NO:4. Functional equivalents of the cel1 include naturally occurring plant cel1 in other plant species, and mutant cel1 whether naturally occurring or engineered. The invention also includes degenerate variants of sequences (a) through (e).

The invention also includes nucleic acid molecules, preferably DNA molecules, that hybridize to, and are therefore the complements of, the nucleotide sequences (a) through (e), in the preceding paragraph. Such hybridization conditions may be highly stringent or less highly stringent, as described below. In instances wherein the nucleic acid molecules are deoxyoligonucleotides ("oligos"), highly stringent conditions refers, e.g., to washing in 6× SSC/0.05% sodium pyrophosphate at 37° C. (for 14-base oligos), 48° C. (for 17-base oligos), 55° C. (for 20-base oligos), and 60° C. (for 23-base oligos).

In another specific embodiment, the invention provides nucleic acid molecules having homologous sequences e.g., nucleotide sequences sharing 60% or 70% or 80% or 90% or 95% homology or identity with the nucleotide sequence of SEQ ID NO:2 of identical size or when compared to an aligned sequence in which the alignment is done by a computer homology program known in the art or whose nucleic acid is capable of hybridizing to a Cel1 coding sequence, under high, moderately high or low stringency conditions.

By way of example and not limitation, procedures using conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5X SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10⁶ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art.

By way of example and not limitation, procedures using conditions of high stringency are as follows: prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10⁶ cpm of $^{32}$P-labeled probe. Washing of filters is done at 37° C. for 1 h in a solution containing 2× SSC, 0.01% PVP, 0.01% Ficoll, and 0.01% BSA. This is followed by a wash in 0.1× SSC at 50° C. for 45 min before autoradiography. Other conditions of high stringency which may be used are well known in the art.

By way of example and not limitation, procedures using conditions of moderately high stringency are as follows: filters containing DNA are pretreated for 6 hours to overnight at 55° C. in buffer composed of 6× SSC, 5× Denhart's 0.5% SDS, 100 mg/mL salmon sperm DNA. Hybridizations are carried out in the same solution upon adding 5–20×10⁶ cpm of $^{32}$P-labeled probe and incubated 8–48 hours at 55° C. Washing of filters is done at 60° C. in 1× SSC, 0.1% SDS, with two exchanges after 30 minutes. Other conditions for moderately high stringency screening are known in the art. For further guidance regarding hybridization conditions see, for example, Sambrook et al., 1989, *Molecular Cloning, A Laboratory Manual*, Cold Spring Harbor Press, New York; and Ausubel et al., 1989, *Current Protocols in Molecular Biology*, Green Publishing Associates and Wiley Interscience, New York.

In addition to the plant cel1 nucleotide sequences described above, full length plant cel1 cDNA or gene sequences present in the same species and/or homologs of the cel1 gene present in other plant species can be identified and readily isolated, without undue experimentation, by molecular biological techniques well known in the art. The identification of homologs of the cel1 in related species can be useful for developing plant model systems for purposes of discovering plant cel1 agonists or antagonists to modify cel1 in plants to alter the following processes in either a positive or negative way: larger or smaller altered plant morphology. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the cel1 gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the cel1 nucleotide sequence, as shown in SEQ ID NO: 2. The hybridization washing conditions used should be of a lower stringency, as described above, when the cDNA library is derived from an organism different from the type of organism from which the labeled sequence was derived.

Alternatively, the labeled cel1 nucleotide probe may be used to screen a genomic library derived from the organism of interest, again, using appropriately stringent conditions. The identification and characterization of plant genomic clones is helpful for use in transgenic plants for regulating plant structural morphology. For example, sequences derived from regions adjacent to the intron/exon boundaries of the plant gene can be used to design primers for use in amplification assays to detect mutations within the exons, introns, splice sites (e.g., splice acceptor and/or donor sites), etc.

Further, a cel1 gene homolog may be isolated from nucleic acid of the organism of interest by performing PCR using two degenerate oligonucleotide primer pools designed on the basis of amino acid sequences within the plant cel1 gene product disclosed herein. The template for the reaction may be cDNA obtained by reverse transcription of mRNA prepared from, for example, plant cell lines or tissue, known or suspected to express a cel1 gene allele.

The PCR product may be subcloned and sequenced to ensure that the amplified sequences represent the sequences of a plant cel1 gene. The PCR fragment may then be used to isolate a full length cDNA clone by a variety of methods. For example, the amplified fragment may be labeled and used to screen a cDNA library, such as a plant cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the plant cel1 gene). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The cel1 gene sequences may additionally be used to isolate mutant cel1 gene alleles. Such mutant alleles may be isolated from plant species either known or proposed to have a genotype which contributes to altered plant morphology. Additionally, such plant cel1 gene sequences can be used to detect plant cel1 gene regulatory (e.g., promoter or promotor/enhancer) defects which can affect plant growth.

A cDNA of a mutant plant cel1 gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in a plant species putatively carrying the mutant plant cel1 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant plant cel1 allele to that of the normal plant cel1 allele, the mutation(s) responsible for the loss or alteration of function of the mutant plant cel1 gene product can be ascertained.

Alternatively, a genomic library can be constructed using DNA obtained from a plant species suspected of or known to carry the mutant plant cel1 allele, or a cDNA library can be constructed using RNA from a tissue known, or suspected, to express the mutant plant cel1 allele. The normal plant cel1 gene or any suitable fragment thereof may then be labeled and used as a probe to identify the corresponding mutant plant cel1 allele in such libraries. Clones containing the mutant plant cel1 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant plant cel1 allele in a plant species suspected of or known to carry such a mutant allele. In this manner, gene products made by the putatively mutant tissue may be expressed and screened using standard antibody screening techniques in conjunction with antibodies raised against the normal plant cel1 gene product, as described, below, in Section 5.3. (For screening techniques, see, for example, Harlow, E. and Lane eds., 1988, *Antibodies: A Laboratory Manual*, Cold Spring Harbor Press, Cold Spring Harbor.) Additionally, screening can be accomplished by screening with labeled Cel1 fusion proteins. In cases where a plant cel1 mutation results in an expressed gene product with altered function (e.g., as a result of a missense or a frameshift mutation), a polyclonal set of antibodies to plant cel1 are likely to cross-react with the mutant plant cel1 gene product. Library clones detected via their reaction with such labeled antibodies can be purified and subjected to sequence analysis according to methods well known to those of skill in the art.

The invention also encompasses nucleotide sequences that encode mutant plant cel1, peptide fragments of the plant Cel1, truncated plant Cel1, and plant Cel1 fusion proteins. These include, but are not limited to nucleotide sequences encoding mutant plant Cel1 described herein. Nucleotides encoding fusion proteins may include by are not limited to full length plant Cel1, truncated plant Cel1 or peptide fragments of plant Cel1 fused to an unrelated protein or peptide, such as for example, a secretion signal peptide.

The invention also relates to Cel1 derivatives or analogues made by altering the cel1 sequence by substitutions, additions or deletions that provide molecules with endo-1, 4-β-glucanase activity. Thus, the Cel1 derivatives include polypeptides containing, as a primary amino acid sequence, all or part of the Cel1 amino acid sequence including altered sequences in which functionally equivalent amino acid residues are substituted for residues within the sequence resulting in a polypeptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The posItively charged (basic) amino acids include arginine, lysine and histidine. The negatively charged (acidic) amino acids include aspartic acid and glutamic acid. Such Cel1 derivatives can be made either by chemical peptide synthesis or by recombinant production from nucleic acid encoding the Cel1 which nucleic acid has been mutated. Any technique for mutagenesis known in the art can be used, including, but not limited to, chemical mutagenesis, in vitro site-directed mutagenesis (Hutchinson et al., 1978, J. Biol. Chem. 253:6551), use of TAB® linkers (Pharmacia), PCR with mutation-containing primers, etc.

Furthermore, if desired, nonclassical amino acids or chemical amino acid analogues can be introduced as a substitution or addition into the Cel1 protein, derivative or analogue. Non-classical amino acids include, but are not limited to, the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

The invention also relates to isolated nucleic acid molecules which comprise the nucleotide sequence of the cel1 promoter.

In a specific embodiment, the isolate nucleic acid molecule comprises or consists of the nucleotide sequence of SEQ ID NO: 1 or functional fragments thereof.

The invention also encompasses (a) recombinant nucleic acid vectors that contain any of the foregoing plant cel1 coding sequences and/or their complements (i.e., antisense); (b) recombinant nucleic acid expression vectors that contain any of the foregoing cel1 coding sequences operatively associated with a regulatory element that directs the expression of the coding sequences; and (c) genetically engineered host cells that contain any of the foregoing plant cel1 coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the promoters derived from the genome of plant cells (e.g., heat shock promoters; the promoter for the small subunit of RUBISCO; the promoter for the chlorophyll a/b binding protein) or from plant viruses (e.g., the 355 RNA promoter of CaMV; the coat protein promoter of tobacco mosaic virus (TMV), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The present invention encompasses a recombinant nucleic acid vector comprising the nucleic acid molecule comprising (a) the nucleotide sequence encoding a protein or polypeptide having the amino acid sequence of SEQ ID NO:4; (b) variant nucleotide sequences of SEQ ID NO:4 which is an allelic variant, species variant, and naturally occurring or man-made functional variants thereof; (c) a nucleic acid molecule encoding derivatives or analogs of the Cel1 polypeptide of SEQ ID NO:4; or (d) the nucleotide sequence of SEQ ID NO:2.

The invention also relates to host cells containing the recombinant nucleic acid vectors described above.

The present invention further relates to recombinant nucleic acid vectors comprising a first nucleic acid sequence encoding a secretion signal peptide and a second nucleic acid sequence encoding a cell wall modulation polypeptide.

In another specific embodiment, the secretion signal peptide is from cel1, obtainable from *Arabidopsis thaliana*.

In a specific embodiment, the recombinant nucleic acid vector has a cell wall modulation protein polypeptide which is a cellulose binding domain as defined above herein.

5.3.2. Cel1 PROTEINS AND POLYPEPTIDES

The present invention encompasses polypeptides comprising an amino acid sequence corresponding to *Arabidopsis thaliana* endo-1,4-β-glucanase (Cel1) gene, allelic and species variants, and naturally occurring and man-made functional variants, and derivatives and analogs thereof.

In a specific embodiment, the present invention provides a polypeptide having the amino acid sequence of SEQ ID NO:4.

Cel1 proteins, polypeptides and peptide fragments, mutated, truncated or deleted forms of the Cel1 and/or Cel1 fusion proteins can be prepared for use as cell wall modulating polypeptides.

The invention also encompasses proteins that are functionally equivalent to the Cel1 encoded by the nucleotide sequences described in Section 5.3.1, supra, as judged by any of a number of criteria, including but not limited endo-1,4-β-glucanase activity. Such functionally equivalent Cel1 proteins include but are not limited to additions or substitutions of amino acid residues within the amino acid sequence encoded by the plant cel1 nucleotide sequences described, above, in Section 5.3.1, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to cell DNA (using random mutagenesis techniques well known to those skilled in the art) and the resulting mutant cell tested for activity, site-directed mutations of the cell coding sequence can be engineered (using site-directed mutagenesis techniques well known to those skilled in the art) to generate mutant plant cells with increased function.

Other mutations to the cell coding sequence can be made to generate Cel1 proteins that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites.

While the Cel1 polypeptides and peptides can be chemically synthesized (e.g., see Creighton, 1983, *Proteins: Structures and Molecular Principles*, W. H. Freeman & Co., New York), large polypeptides derived from the Cel1 and the full length Cel1 itself may advantageously be produced by recombinant DNA technology using techniques well known in the art for expressing nucleic acid containing plant Cel1 gene sequences and/or coding sequences. Such methods can be used to construct expression vectors containing the cell nucleotide sequences described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding cell nucleotide sequences may be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

Also included within the scope of the invention are Cel1 proteins, derivatives, and analogues which are differentially modified during or after synthesis, e.g., by biotinylation, benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the MDC proteins, derivatives, or analogues are acetylated at the N-terminus and/or amidated at the C-terminus. Any of numerous chemical modifications may be carried out by known techniques, including, but not limited to, acetylation, formylation, oxidation, reduction, metabolic synthesis in the presence of tunicamycin, etc. These modifications may serve to increase the stability, bioavailability and/or inhibitory action of the peptides of the invention.

Any of the Cel1 proteins, derivatives or analogues described above may, additionally, have a non-peptide macromolecular carrier group covalently attached to its amino and/or carboxy termini. Such macromolecular carrier groups may include, for example, lipid-fatty acid conjugates or carbohydrates.

Endo-1,4-β-glucanase activity and/or the ability to bind cellulose of the Cel1 variants or derivatives (including fragments and chimeric proteins) or analogues thereof, for use in transgenic plants can be demonstrated by any of the methods disclosed in Sections 5.4 and 6 infra or known to one skilled in the art.

A variety of host-expression vector systems may be utilized to express the plant cel1 nucleotide sequences of the invention.

Methods which are well known to those skilled in the art can be used to construct expression vectors containing the plant cel1 coding sequence and appropriate transcriptional/translational control signals. These methods include in vitro recombinant DNA techniques, synthetic techniques and in vivo recombination/genetic recombination. See, for example, the techniques described in Maniatis et al., 1989, *Molecular Cloning A Laboratory Manual*, Cold Spring Harbor Laboratory, New York and Ausubel et al., 1989, *Current Protocols in Molecular Biology*, Greene Publishing Associates and Wiley Interscience, New York.

A variety of host-expression vector systems may be utilized to express the cel1 coding sequence. These include but are not limited to microorganisms such as bacteria transformed with recombinant bacteriophage DNA, plasmid DNA or cosmid DNA expression vectors containing the plant GluR coding sequence; yeast transformed with recombinant yeast expression vectors containing the plant GluR coding sequence; insect cell systems infected with recombinant virus expression vectors (e.g., baculovirus) containing the cel1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the cel1 coding sequence; or animal cell systems infected with recombinant virus expression vectors (e.g., adenovirus, vaccinia virus) including cell lines engineered to contain multiple copies of the cel1 either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., the cel1 promoter, heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of the cel1 DNA SV40-, BPV- and EBV-based vectors may be used with an appropriate selectable marker.

In bacterial systems a number of expression vectors may be advantageously selected depending upon the use intended for the Cel1 expressed. For example, when large quantities of Cel1 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the cel1 coding sequence may be ligated into the vector in frame with the lac Z coding region so that a hybrid Cel1 lac Z protein is produced; *E. coli* expression vector pET3d obtained from Novagen (Madison, Wis.) as we have already successfully prepared and used to purify antibodies from rabbits; pIN vectors (Inouye & Inouye, 1985, Nucleic acids Res. 13:3101–3109; Van Heeke & Schuster, 1989, J. Biol. Chem. 264:5503–5509); and the like.

In yeast, a number of vectors containing constitutive or inducible promoters may be used. For a review see, *Current Protocols in Molecular Biology*, Vol. 2, 1988, Ausubel et al. eds., Greene Publish. Assoc. & Wiley Interscience, Ch. 13; Grant et al., 1987, Expression and Secretion Vectors for Yeast, in *Methods in Enzymology*, Wu & Grossman eds., 1987, Acad. Press, N.Y., Vol. 153, pp. 516–544; Glover, 1986, *DNA Cloning*, Vol. II, IRL Press, Wash., D.C., Ch. 3; and Bitter, 1987, "Heterologous Gene Expression in Yeast", *Methods in Enzymology*, Berger & Kimmel eds., Acad. Press, N.Y., Vol. 152, pp. 673–684; and *The Molecular Biology of the Yeast Saccharomyces*, 1982, Strathern et al. eds., Cold Spring Harbor Press, Vols. I and II.

In cases where plant expression vectors are used, the expression of the cel1 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the cel1 promoter or functional fragments thereof, the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology*, Academic Press, N.Y., Section VIII, pp. 421–463; and Grierson & Corey, 1988, *Plant Molecular Biology*, 2d Ed., Blackie, London, Ch. 7–9.

For long-term, high-yield production of recombinant proteins, stable expression is preferred. For example, cell lines which stably express the plant Cel1 protein may be engineered. Rather than using expression vectors which contain viral origins of replication, host cells can be transformed with the cel1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin genes (Santerre, et al., 1984, Gene 30:147). Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, in *Current Communications in Molecular Biology*, Cold Spring Harbor Laboratory ed.). The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells and/or plants that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

5.3.3. PREPARATION OF Cel1 PROTEINS, DERIVATIVES AND ANALOGUES

The endo-1,4-β-glucanase (Cel1), and derivatives or analogues thereof can be purified from biological tissue or cell culture, or produced by recombinant or synthetic techniques known in the art.

Native Cel1 preparations can be obtained from a variety of sources. Standard methods of protein purification may be used to isolate and purify, or partially purify, endo-1,4-β-glucanases from any source known to contain or produce the desired endo-1,4-β-glucanase (Cel1), e.g., Cel1 may be isolated from sources such as plant tissues. Such standard protein purification techniques include, but are not limited to, chromatography (e.g., ion exchange, affinity, gel filtration/molecular exclusion chromatography and reversed phase high performance liquid chromatography (RP-HPLC)), centrifugation, differential solubility, and electrophoresis (for a review of protein purification techniques, see, Scopes, 1987, *Protein Purification; Principles and Procedure*, 2nd Ed., C. R. Cantor ed., Springer Verlag, New York, N.Y., and Parvez et al., 1985, *Progress in HPLC*, Vol. 1, Science Press, Utrecht, The Netherlands).

Recombinant expression techniques can be applied to obtain the Cel1 proteins, derivatives, and analogues of the invention (see, e.g., Sambrook et al., 1989, *Molecular Cloning, A Laboratory Manual*, Cold Spring Harbor Laboratory, 2d Ed., Cold Spring Harbor, N.Y.; Glover, D. M. ed., 1985, *DNA Cloning: A Practical Approach*, MRL Press, Ltd., Oxford, U.K., Vol. I, II). The nucleotide sequence of cel1 is set forth in SEQ ID NO:2. An cel1 clone can be isolated using well-known techniques in the art, such as by screening a library, chemical synthesis, or polymerase chain reaction (PCR). Cloned cel1 gene sequences can be modified by any of numerous strategies known in the art.

To produce a recombinant Cel1 protein, derivative or analogue, a nucleic acid sequence encoding the Cel1 protein, derivative or analogue is operatively linked to a promoter such that the Cel1 protein, derivative, or analogue is produced from said sequence. For example, a vector can be introduced into a cell, within which cell the vector or a portion thereof is expressed, producing Cel1 or a portion thereof. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art.

A method for the production of Cel1 comprises: (a) culturing a host cell containing a recombinant expression vector, said vector comprising a nucleotide sequence encoding Cel1 under conditions such that Cel1 is expressed by the cell; and (b) recovering Cel1 expressed by the cell.

A variety of host-vector systems may be utilized to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities and depending on the host-vector system utilized, any one of a number of suitable transcription and translation elements may be used.

Expression of a Cel1 protein, derivative, or analogue may be controlled by any promoter/enhancer element known in the art. Such promoters include, but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the HSV-1 (herpes simplex virus-1) thymidine kinase promoter (Wagner et al., 1981, Proc. Natl. Acad. Sci. USA 78:1441–1445), the regulatory sequences of the metallothionein gene (Brinster et al., 1982, Nature 296:39–42); prokaryotic expression vectors such as the β-lactamase promoter (Villa-Kamaroff et al., 1978, Proc. Natl. Acad. Sci. USA 75:3727–3731), or the tac promoter (DeBoer et al., 1983, Proc. Natl. Acad. Sci. USA 80:21–25); see also "Useful proteins from recombinant bacteria" in Scientific American, 1980, 242:74–94; plant expression vectors comprising the cel1 promoter or functional fragments thereof, the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). The promoter element which is operatively linked to the nucleic acid encoding a Cel1 protein, derivative or analogue can also be a bacteriophage promoter with the source of the bacteriophage RNA polymerase expressed from a gene for the RNA polymerase on a separate plasmid, e.g., under the control of an inducible promoter, for example, the nucleic acid encoding chemokine, derivative, or analogue, operatively linked to the T7 RNA polymerase promoter with a separate plasmid encoding the T7 RNA polymerase.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered chemokine, derivative or analogue may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast or insect cells will produce a glycosylated product. Expression in mammalian or plant cells can be used to ensure "native" glycosylation of a heterologous protein. Furthermore, different vector/host expression systems may effect processing reactions to different extents.

The Cel1-encoding nucleic acid sequence can be mutated in vitro or in vivo, to create and/or destroy translation, initiation, and/or termination sequences, or to create variations in coding regions. Any technique for mutagenesis known in the art can be used, including, but not limited to, in vitro site-directed mutagenesis (Hutchinson et al., 1978, J. Biol. Chem. 253:6551), use of TAB® linkers (Pharmacia), mutation-containing PCR primers, etc.

The experimentation involved in mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

In other specific embodiments, the Cel1 derivative or analogue may be expressed as a fusion, or chimeric protein product (comprising the protein, fragment, analogue, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

In addition, Cel1 proteins, derivatives (including fragments and chimeric proteins), and analogues can be chemically synthesized. See, e.g., Clark-Lewis et al., 1991, Biochem. 30:3128–3135 and Merrifield, 1963, J. Amer. Chem. Soc. 85:2149–2156. For example, Cel1, derivatives and analogues can be synthesized by solid phase techniques, cleaved from the resin, and purified by preparative high performance liquid chromatography (e.g., see Creighton, 1983, *Proteins, Structures and Molecular Principles*, W. H. Freeman and Co., N.Y., pp. 50–60). Cel1, derivatives and analogues that are proteins can also be synthesized by use of a peptide synthesizer. The composition of the synthetic peptides may be confirmed by amino acid analysis or sequencing (e.g., the Edman degradation procedure; see Creighton, 1983, *Proteins, Structures and Molecular Principles*, W. H. Freeman and Co., N.Y., pp. 34–49).

The Cel1 proteins, derivatives, or analogues of the invention may be synthesized in their entirety by the sequential addition of amino acid residues or alternatively as fragment subcomponents which may be combined using techniques well known in the art, such as, for example, fragment condensation (Shin et al., 1992, Biosci. Biotech. Biochem. 56:404–408; Nyfeler et al., 1992, *Peptides, Proc. 12th Amer. Pep. Soc.*, Smith and Rivier eds., Leiden, pp 661–663); and Nokihara et al., 1990, *Protein Research Foundation*, Yanaihara ed., Osaka, pp 315–320).

In a less preferred embodiment, Cel1 derivatives can be obtained by proteolysis of the protein followed by purification using standard methods such as those described above (e.g., immunoaffinity purification).

5.4. APPLICATIONS

The present invention finds use in various applications, including but not limited to, those listed hereinbelow.

First, the present invention can be used to provide fast growing transgenic forest trees for the evergrowing pulp and paper industry, thereby reducing the devastating ecological effects associated with rain forest exhaustion.

Second, the present invention can be used to provide transgenic plants with modified cell walls possessing different properties, such as, but not limited to, plants having longer or shorter fibers; plants which are either more or less resistant to biodegradation; plants which are either more or less digestible in the rumen of animals; and plants which are either more or less resistant to pests, such as insects, fungi, viruses and bacteria.

Third, the present invention can be used to provide transgenic plants with useful fibers such as, cotton, flax, etc. that produce higher yields of modified fibers which have longer or shorter fibers; or have modified properties such as "look", absorbency, strength and reology of the chemically modified cellulose.

The present invention can be further used to provide transgenic fruiting plants, such as tomato plants, etc., the fruits thereof having higher cellulose content which can be used in the ketchup and tomato puree industry. The present invention can also be used to provide transgenic potato plants with faster growing canopies and shorter life cycles which result in shorter time between planting and harvesting, and/or higher tuber yield. The present invention can further be used to provide transgenic flowering plants having longer or shorter stems, larger or smaller petals, etc. In addition, the invention can be used to provide fast growing rice that will emerge more quickly from the water and thus, have an increased survival rate and yield. Furthermore, the present invention can be used to provide lettuce plants featuring larger or smaller leaves. And finally, the invention can be used to provide forage crops, such as alfalfa, clover, etc., with higher biomass and/or modified digestibility in rumen animals.

A further utility of the present invention is to improve the rate of growth of naturally occurring metal or toxin hyper-accumulating plants to increase their biomass thereby improving the rate or extent of phytoremediation. (See Glass, Oct. 1, 1997, Genetic Engineering News, p. 8, 41–43).

The cel1 gene of the invention has utility as a transgene encoding cell wall modulation protein or polypeptide in a transgenic plant to alter plant structure or morphology. The cel1 gene also has utility for encoding the Cel1 protein in recombinant vectors which may be inserted into host cells to express the Cel1 protein. Further, the cel1 gene of the invention may be utilized (1) as a nucleic acid probe to screen nucleic acid libraries to identify other endo-1,4-β-glucanase genes or mutants; (2) as a nucleic acid sequence to be mutated or modified to produce Cel1 protein variants or derivatives; (3) isolation of the nucleic acid sequence encoding the Cel1 secretion signal peptide; and (4) as a nucleic acid encoding endo-1,4-β-glucanase in molecular biology techniques or industrial applications commonly known to those skilled in the art.

The cel1 nucleic acid molecules may be used as plant cel1 antisense molecules, useful, for example, in plant cel1 gene regulation or as antisense primers in amplification reactions of plant cel1 gene nucleic acid sequences. With respect to plant cel1 gene regulation, such techniques can be used to regulate, for example, plant growth, development or gene expression. Further, such sequences may be used as part of ribozyme and/or triple helix sequences, also useful for cel1 gene regulation.

The cel1 promoter of the present invention may be utilized as an elongating tissue specific plant promoter to express any protein, polypeptide or peptide of interest in a tissue specific manner in a transgenic plant. In particular, the cel1 promoter may be used to express a cell wall modulation protein or polypeptide in an elongating tissue specific manner to produce transgenic plants having altered structure. Further, the cel1 promoter can be used to express any CBD in elongating tissues of transgenic plants to produce plants having altered structure.

The *Arabidopsis thaliana* Cel1 protein of the invention can be used in any biochemical applications (experimental or industrial) where endo-1,4-β-glucanase activity is desired, for example, but not limited to, digestion of polysaccharides, modification of cellulose, modification of elongating plant structures, and experimental or industrial biochemical applications known to those skilled in the art.

The Cel1 secretion signal peptide of the invention may be utilized to facilitate the cellular secretion of any protein, polypeptide or peptide of interest by constructing recombinant nucleic acids encoding the Cel1 secretion signal peptide fused to a sequence encoding a protein of interest, and expressing the recombinant proteins.

The following examples are presented for purposes of illustration only and are not intended to limit the scope of the invention in any way.

6. EXPERIMENTAL PROTOCOLS OF THE EXAMPLES

The following protocols and experimental materials were employed in the Examples that follow.

6.1. PLANT MATERIAL AND GROWTH CONDITIONS

*Arabidopsis thaliana* cv. Columbia and *Nicotiana tabaccum*-SR1 (tobacco) plants were grown at 24–25° C. under a 16 h photoperiod, using cool-white fluorescent light (50–60 µE m$^{-2}$ S$^{-1}$). Dwarf *A. thaliana* plants were produced by treating the potting mixture prior to seeding with 250 ppb uniconazole [(E)-1-(4-chlorophenyl)-4,4-dimethyl-2-(1,2,4-triazol-1-yl)lpenten-3-ol] (Agan chemicals Inc., Israel), a giberellin biosynthesis inhibitor (Henry, 1985, Bull. Plant Growth Regul. Soc. Am. 13:9–11).

6.2. ISOLATION OF PLANT NUCLEIC ACIDS FROM PLANT TISSUE

DNA was extracted from stems and leaves of *Arabidopsis thaliana* cv. Columbia as described by Doyle and Doyle (1987, Phytochem. Bull. 19:11–15). RNA was extracted from elongating stems with "TRI-REAGENT™" (Molecular Research Center Inc., Cincinnati, Ohio), according to the manufacturer's instructions.

6.3. PCR AMPLIFICATION OF THE EGASE DNA PROBE FROM CHROMOSOMAL DNA

Degenerate primers (Compton, 1990, "Degenerate primers for DNA amplification," in *PCR Protocols: A Guide to Methods and Applications*, Innis, Gelfand, Sninsky, and White eds., Academic Press, San Diego, Calif.) were synthesized based on two conserved amino acid regions, GGYYDA (SEQ ID NO:10) and CWERPEDM (SEQ ID NO:11), from avocado and tomato cellulase amino acid sequences (Tucker and Milligan, 1991; Lashbrook et al., 1994).

Primer #1 GGYYDA (SEQ ID NO:10): 5'-GAATTCGGA (T/C/G) GGA(T/C/G)TAT(C)TAT(C)GAC(T)GC-3' (SEQ ID NO:12). Primer #2 CWERPEDM (SEQ ID NO:12): 5'-GAATTCCATA(G)TCT(C)TCA(G/C/T)GGA (T/C/G) CGT(C)TCCAA(G)CA-3'(SEQ ID NO:13).

The PCR mix contained 2 µl chromosomal DNA (0.5 µg/µl), 2.5 ml 10× Taq Polymerase buffer (Promega, Madison, Wis.), 1 µl dNTP mix (10 mM), 1.5 µl 25 mM MgCl$_2$, 0.5 µl (25 µM) of each primer, 1 unit Taq polymerase (Promega, Madison, Wis.) and double distilled H$_2$O (ddH$_2$O) to a final volume of 25 µl. Mineral oil (25 µl) was added to prevent evaporation. The PCR program was as described in Comptom (1990, "Degenerate primers for DNA amplification" in *PCR Protocols: A Guide to Methods and Applications*, pp 39–45, eds Innis, Gelfand, Sninsky, and White, Academic Press, San Diego, Calif.).

A fragment of 260 by amplified by the PCR reaction was purified on a 2% (w/v) agarose/TBE gel as described in Sambrook et al., (1989, *Molecular Cloning: A Laboratory Manual*, Cold Spring Harbor Laboratory Press, New York) and is shown in FIG. 1. The isolated 260 by fragment was digested with EcoRI and cloned into the EcoRI cloning site of the M13 RF DNA mp18 vector (New England Biolabs, Beverly, Mass.).

6.4. CLONING OF *A. THALIANA* GENOMIC EGASE GENE

The genomic clone of EGase was isolated using an *A. thaliana* genomic library packaged in the vector EMBL3 (Promega, Madison, Wis.). The library was constructed from *A. thaliana* genomic DNA partially digested with SauA3 and cloned into the BamHI cloning site of the EMBL3 vector. A total of 2.5×10$^5$ plaques were screened using the PCR-derived DNA EGase probe (260 by PCR fragment, FIG. 1) according, to Sambrook et al. (1989). A single hybridizing recombinant phage was detected and purified to homogeneity. Fragments containing the EGase gene within the λ genomic clones or subsequent plasmid subclones of pUC18 (New England Biolabs, Beverly, Mass.) were localized by Southern blot analysis (Southern, 1975, J. Mol. Biol. 98:503–517). Overlapping serial deletions of genomic subclones were generated by ExoIII digestion of the subclones as shown in the gene construction scheme set forth in FIG. 2. The Arabidopsis EGase sequence (cel1)was deposited under the non-disclosure terms in the EMBL Nucleotide Sequence Submissions, European Bioinformation Institute, Hinxton Hall, Hinxton, Cambridge, and was given the accession #X98543 (SEQ ID NO:9).

6.5. CLONING cel1 cDNA

RNA extracted from elongating stems of *A. thaliana* was used as a template for the reverse transcriptase polymerase chain reaction (RT-PCR kit, Stratagene, La Jolla, Calif.). Total cDNA was used for the PCR reaction. Two specific primers were designed according to the terminal exon sequences. Primer #3: 5'-ATGGCGCGAAAATCCCTAAT-3' (SEQ ID NO:14) also (nucleotides 1666–1685 in SEQ ID NO:9); and Primer #4: 5'-TCATCGCCAAGTAGAA-3' (SEQ ID NO:15) also (nucleotides 5258–5273 in SEQ ID NO:9). The resulting 1.5 kb PCR fragment (FIG. 3) was cloned into the pGEM-T Vector system (Promega, Madison, Wis.) and sequenced. This sequence was deposited under the non-disclosure terms in the EMBL Nucleotide Sequence Submissions, European Bioinformation Institute, Hinxton Hall, Hinxton, Cambridge, and was given the accession #X98544 (SEQ ID NO:2).

6.6. NUCLEOTIDE SEQUENCE DETERMINATIONS

Nucleotide sequences were determined using an automated sequencer Model 373 (Perkin-Elmer, California, USA), according to the manufacturer's instructions.

6.7. NORTHERN BLOT ANALYSIS

A 768 by DNA probe, (starting at nucleotide 399 of SEQ ID NO:2) generated from the cel1 cDNA clone (SEQ ID NO:2) was used for northern blot analysis. In each experiment, 40–50 *A. thaliana* plants were used to extract total RNA from the following tissues: fully expanded leaves, basal internode of flowering stems, the elongation zone in the flowering stem of normal plants and the elongation zone in the flowering stem of dwarf plants (treated with uniconazole as described above).

Total RNA (10 µg) was separated on a 1.6% agarose gel and transferred to a "HYBOND-N$^+$" membrane (Amersham, United Kingdom). The DNA probe was $^{32}$P-labeled by the "REDI PRIME™" kit (Random Prime Labeling, Kit, Amersham, United Kingdom). The membranes were hybridized at 55° C. for 16 hr. The final wash was carried out in 0.5× SSC, 0.1% (W/V) SDS for 10 min at 60° C. The 18S rRNA probe was used as an internal standard. RNA levels were determined using densitometry.

6.8. CONSTRUCTION OF cel1 PROMOTER-gus BINARY VECTOR (pPCGUS)

A DNA fragment which includes the cel1 promoter region of *A. thaliana* endo-1,4-β-glucanase (cel1, nucleotides 5–1618 of SEQ ID NOs:1 or 9) was cloned into pUC18 (New England Biolabs, Beverly, Mass.). Briefly, a PCR fragment was generated using the following primers: #5 (HindIII): 5'-AAAAAAGCTTACCTGCAGGTCAACGG- 3') (SEQ ID NO:16), and #10 (SalI): 5'-AAAAGTCGACGAAGGTGATAGGACCAAC-3' (SEQ ID NO:6), digested with restriction endonucleases HindIII and SalI, and cloned into the HindIII and SalI cloning sites of pUC18 (New England Biolabs Beverly, Mass.). A 1.6 kb HindIII-SalI fragment excised from the above construct was subcloned into the HindIII and SalI cloning sites of the binary vector pBI101 (Clontech, Palo Alto, Calif.), at the 5' end of the gus gene (Jefferson, 1987, Plant Mol. Biol. Rep. 5:387–405) and designated pPCGUS.

6.9. CONSTRUCTION/TRANSGENIC PLANTS EXPRESSING cel1 PROMOTER-gus FUSION

The above construct, i.e. pPCGUS was mobilized into disarmed LB 4404 *Agrobacterium tumefaciens* by triparental mating (An, 1987, Meth. Enzymol. 153: 292–305). Leaf-disc transformation was performed with *Nicotiana tabaccum*-SR1 plants as described previously (DeBlock et al., 1984, EMBO J. 3:1681). Regenerated transgenic plants were selected on kanamycin. $F_1$ seeds from eight independent plants transformed with the construct were used for the functional assays.

The plants were analyzed for the presence of the putative cel1 promoter region by southern blot. As a control for basal levels of GUS activity in tobacco, plants were transformed with the promoterless pBI101. Transgenic plants were grown in the greenhouse at 25° C. under a 16 hr photoperiod.

6.10. HISTOLOGICAL GUS STAINING ANALYSIS OF TRANSGENIC PLANTS

GUS staining was performed with X-Gluc as described previously (Jefferson et al., 1987, Plant Mol. Biol. Rep. 5:387–405). Ten day old seedlings were incubated overnight with X-Gluc at 37° C. and then kept in a 70% ethanol solution. Prior to being photographed, the plants were incubated for few minutes in 90% lactic acid at 90° C. and then cooled to room temperature for 2 hr.

6.11. CONSTRUCTION OF cel1 PROMOTER-cel1 SIGNAL-cbd BINARY VECTOR (pCC1)

A DNA fragment which includes the cel1 promoter region and encodes the cel1 signal peptide, i.e., part of *A. thaliana* endo-1,4-β-glucanase (cel1, nucleotides 5–1770 of SEQ ID NOs: 1 or 9) was cloned into pUC18 (New England Biolabs, Beverly, Mass.). Briefly, a PCR fragment was generated, using the following primers: #5 (HindIII): 5'-AAAAAAGCTTACCTGCAGGTCAACGG-3' (SEQ ID NO:16), and #6 (SalI): 5'-AAAAGTCGACTTTACGGAGAGCGTCGC-3' (SEQ ID NO:17) digested with restriction endonucleases HindIII and SalI, and was cloned into the HindIII and SalI cloning sites of pUC18 (New England Biolabs, Beverly, Mass.).

A cellulose binding domain DNA fragment containing the nucleotide sequence encoding a fragment of the cbpA protein of *Clostridium cellulovorans* (said cellulose binding domain herein referred to as "cbd") (see U.S. Pat. No. 5,496,934) (nucleotides 3–494 of SEQ ID NO:5) was generated by PCR amplification using the following primers: #7 (SalI) 5'-AAAAGTCGACATGGCAGCGACATCATCAA-3' (SEQ ID NO:18) and #8 (BamHI) 5'-AAAAGGATCCCTATGGTGCTGTACCAAG)-3' (SEQ ID NO:19), which included SalI and BamHI restriction sites.

Following digestion with SalI and BamHI restriction endonucleases, the cbd coding DNA fragment was cloned into the SalI and BamHI sites of the above modified pUC18 vector, fused to, and in frame with, the signal peptide of cel1.

The primer for the C-terminal end of the cbd gene contained a stop codon. The SalI site between the two fragments adds two in frame amino acids: Valine and sparagine, which are present between the cel1 signal peptide and the cbd coding regions.

A HindIII-SacI DNA fragment containing the cel1 promoter region, the cel1 signal peptide and the fused cbd, in that order, was subcloned into the binary vector pBI101 (Clontech, Palo Alto, Calif.) which was predigested with HindIII and SacI. This vector was designated pCC1.

6.12. CONSTRUCTION OF CaMV35S Ω PROMOTER-cel1 SIGNAL-cbd BINARY VECTOR (p35SC1)

A vector containing the CaMV35S Ω promoter fused to the cel1 signal sequence and to the cbd sequence was constructed as follows. A DNA fragment encoding the cel1 signal peptide (nucleotides 1–105 of SEQ ID NO:2) was cloned into pUC18 (New England Biolabs, Beverly, Mass.). Briefly, a PCR fragment of cel1 was generated using the following primers: #9 (SphI) 5'-AAAAGCATGCCGCGAAAATCCCTAATTT-3' (SEQ ID NO:20) and #6 (SalI): 5'-AAAAGTCGACTTTACGGAGAGCGTCGC-3' (SEQ ID NO:17), digested with restriction endonucleases SphI and SalI, and cloned into the SphI and SalI cloning sites of pUC18. Inclusion of the SphI restriction site replaced the first amino acid after the initiation site from Alanine to Proline. In addition, the primer for the C-terminal end of the cbd gene contained a stop codon. The SalI site between the two fragments adds two in frame amino acids: Valine and Asparagine, which are present between the cel1 signal peptide and the cbd coding regions.

A cbd encoding DNA fragment (nucleotides 3–494 SEQ ID NO:5) was generated by PCR amplification using the following primers: #7 (SalI) 5'-AAAAGTCGACATGGCAGCGACATCATCAA-3' (SEQ ID NO:18) and #10 (EcoRI) 5'-AAAAGAATTCCTATGGTGCTGTACCAAG-3' (SEQ ID NO:21), which included SalI and EcoRI restriction sites.

Following SalI and EcoRI restriction, the cbd encoding DNA fragment was cloned into the SalI and EcoRI sites of the above modified pUC18 vector, fused to, and in frame with, the signal peptide of cel1.

The DNA containing the cel1 signal-cbd fusion was cloned into pCd cloning cassette (Broido et al., 1993, Physiologia Plantarum 88:259–266) using the SphI and EcoRI cloning sites. The pCd cassette contains a polylinker down stream of a CaMV35S promoter (Guilley et al., 1982, Cell 30:763–773) and the Ω DNA sequence from the coat protein gene of tobacco mosaic virus (Gallie et al., 1987, Nucl. Acid Res. 15:3257–3273). A DNA fragment containing a CaMV35SΩ cel1-signal peptide-cbd and the octopine polyadenylation site was excised using BamHI and SacI and was subcloned into the BamHI and SacI cloning sites of the binary vector pBI101 (Clontech, Palo Alto, Calif.). The resulting vector was designated p35SC1.

6.13. CONSTRUCTION OF cbd TRANSGENIC PLANTS

The binary vectors (p35SC1, pCC1 and pBI101, as a control) were mobilized into disarmed LB 4404 *Agrobacterium tumefaciens* by triparental mating (An, 1987, Meth. Enzymol. 153: 292–305). Leaf-disc transformation was performed with *Nicotiana tabaccum*-SR1 plants as described previously (DeBlock et al., 1984, EMBO J. 3:1681). Regenerated transgenic plants were selected on kanamycin. $F_1$ Seeds were collected from independent plants transformed with each one of the vectors. The plants were analyzed by Southern blot (Sambrook et al., 1989, *Molecular Cloning: A Laboratory Manual*, Cold Spring Harbor Laboratory Press, New York; Southern, 1975, J. Mol. Biol. 98:503–517) and PCR using primers #7 and #8 (SEQ ID NOs:18 and 19, respectively). Transgenic plants were grown in the greenhouse at 25° C. under a 16 hr photoperiod.

6.14. TRANSCRIPTION ANALYSIS OF cbd

To determine transcription of the cbd transgene, RNA extracted from elongating stems and young leaves was used as a template for reverse transcriptase reaction (RT-PCR kit) (Stratagene, La Jolla, Calif.). The total cDNA was used for the PCR amplification using primers #7 and #8 (SEQ ID NOs:18 and 19, respectively).

7. EXAMPLE: CLONING OF *ARABIDOPSIS THALIANA* EGASE DNA PROBE

The EGASE gene, i.e., cel1 of *A. thaliana* was isolated. Considerable homology exists between the different EGase genes from different plants (Lashbrook et al., 1994, Plant Cell 6:1485–1493; Tucker and Milligan, 1991 Plant Physiol. 95:928–933; Wu et al., 1996, Plant Physiol. 110:163–170). Degenerate primers (SEQ ID NOs: 12 and 13) were synthesized based on two conserved regions from avocado and tomato cellulase amino-acid sequences (Lashbrook et al., 1994, Plant Cell 6:1485–1493; Tucker and Milligan, 1991, Plant Physiol. 95:928–933) and enabled the amplification of a 260 by PCR fragment which served as a probe to clone a genomic cel1 from *A. thaliana*. These primers have been used successfully in the past in the isolation of several DNA fragments from mung bean that encode EGase genes (Shoseyov, L., 1992, "Endo-1,4-β-glucanase gene expression during adventitious root formation in Mung bean cuttings," Master thesis, the Hebrew University of Jerusalem).

PCR amplification was performed using chromosomal DNA as the template and two degenerate primers designed according to conserved amino-acid sequences in avocado and tomato EGases (Lashbrook et al., 1994, The Plant Cell 6:1485–1493; Tucker and Milligan, 1991, Plant Physiol. 95:928–933). PCR amplification resulted in two DNA fragments of about 260 and 370 by (FIG. 1). The isolated 260 by fragment was cloned into M13 mp18. Single stranded DNA was then used for sequence analysis. The deduced amino-acid sequence of the 260 by fragment revealed 62% homology to the avocado EGase.

8. EXAMPLE: ISOLATION AND CHARACTERIZATION OF THE EGASE GENOMIC CLONE

Figure 5A:
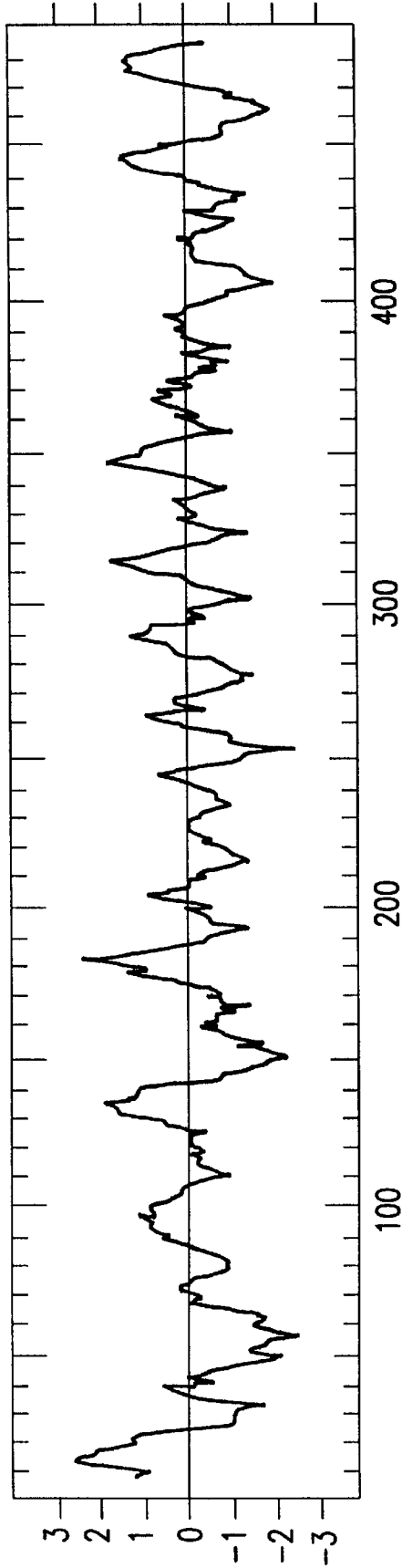
Figure 5B:
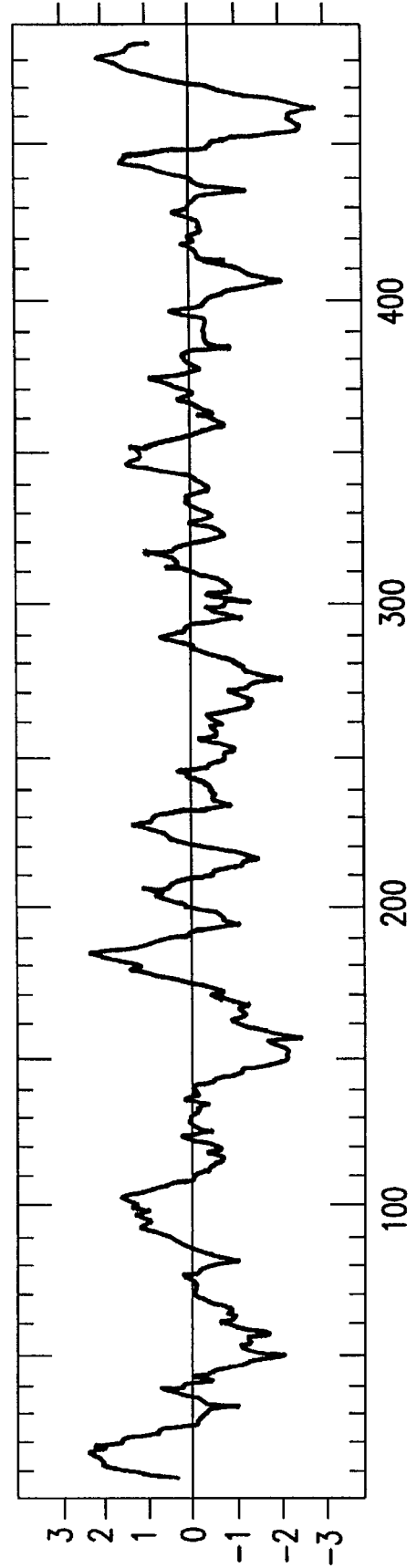

A comparison of the *A. thaliana* cel1 genomic gene with avocado cel1 reveals that exons 2 and 3 of the avocado gene are intercepted by a large intron. This intron does not exist in *A. thaliana* cel1. The *A. thaliana* cel1 cDNA gene encoded a 54-kDa protein. A sequence comparison with avocado EGase revealed 56% sequence identity (FIG. 4). Furthermore, a high degree of conservation was found in the number and positions of the cysteine residues between the proteins, suggesting a conserved tertiary structure. This was also supported by comparing Kyte-Doolittle hydropathy analyses of *A. thaliana* Cel1 and avocado EGase (Cel1) (FIG. 5). The cel1 deduced amino-acid sequence contained one potential glycosylation site. A 17 amino acid motif which classifies Cel1 in the E family of glycosidases was also detected (see generally, Gilkes et al., 1991, Microbiol. Rev. 55:303–315 regarding glycosidases). The first 25 amino acids at the N-terminus were hydrophobic, including a positively charged arginine residue near the very end of the N-terminus, as expected in a typical signal-peptide sequence (Von Heijne et al., 1983, Eur. J. Biochem. 133:17–21).

Figure 2:
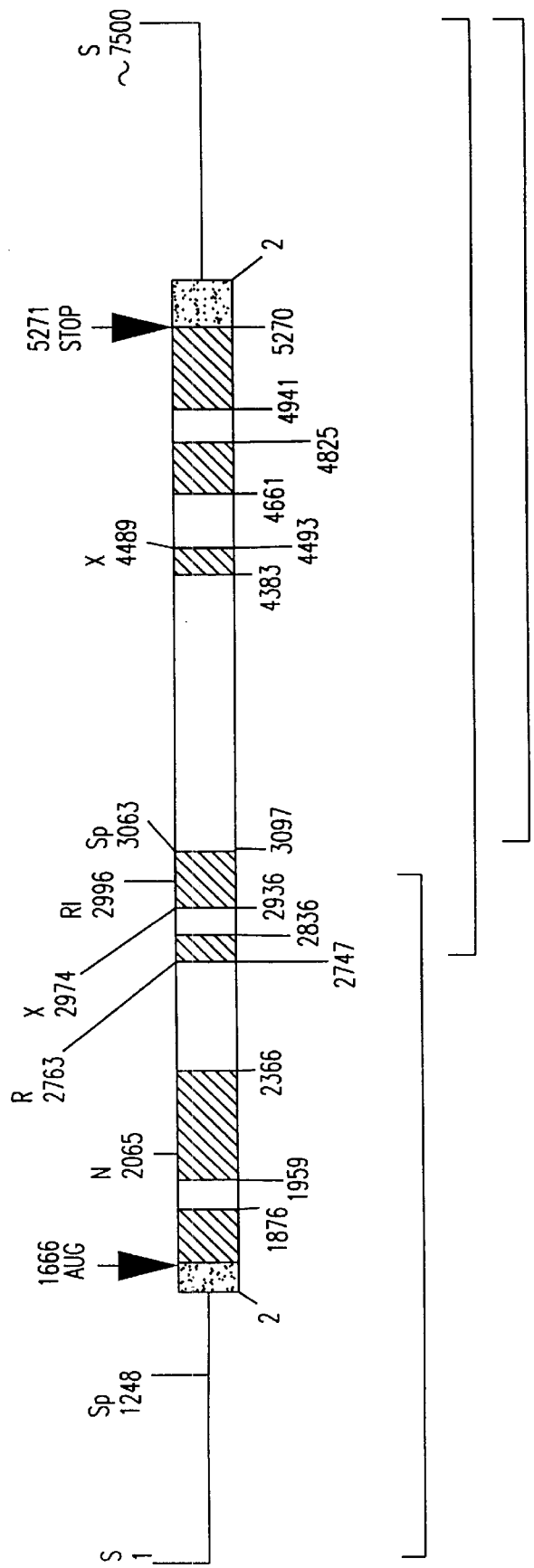

An *A. thaliana* genomic library was screened to isolate the genomic cel1 gene. One positive clone was isolated from a total of $2.5 \times 10^5$ recombinant plaque-forming units screened using the 260 by PCR fragment (FIG. 1) as a probe. SalI digestion of the positive clone, followed by Southern blot analysis, revealed a 7.5-kb fragment. A restriction map of the SalI DNA fragment is presented in FIG. 2. Three different subclones were constructed in pUC18 as further depicted in FIG. 2. ExoIII deletions followed by sequence analysis revealed the primary DNA sequence of the full-length cel1 gene. As represented in FIG. 2, the gene consists of seven exons intercepted by six introns.

9. EXAMPLE: ISOLATION AND CHARACTERIZATION OF cel1 cDNA

RT-PCR was used to test for the presence of cel1 mRNA in elongating tissue and to isolate the full-length cDNA. The cel1 1.5-kb cDNA fragment (FIG. 3) was successfully cloned and sequenced (SEQ ID NO:2). The cDNA sequence perfectly matched the DNA sequence of the combined exons (nucleotides 1666–1875, 1959–2366, 2747–2386, 2936–3097, 4383–4493, 4661–4825 and 4941–5270 of SEQ ID NO:9). Several sequence discrepancies were found between the 260-by DNA probe and cel1 cDNA. At this point it was not determined if these changes represent different genes or simply PCR derived mutations. The 1476 by open reading frame (nucleotides 1–1476, SEQ ID NOs:2 and 3) was found to encode a 492 amino acid polypeptide (SEQ ID NO. 4) with a predicted molecular weight of 54 kDa. Sequence comparison with avocado EGase revealed 56% identity (FIG. 4). A comparison of Kyte-Doolittle hydropathy analyses (Kyte and Doolittle, 1982, J. Mol. Biol. 157:105–132) of *A. thaliana* Cel1 and avocado EGase (Cel1) is presented in FIG. 5.

10. EXAMPLE: RNA TRANSCRIPT LEVELS OF cel1 IN DIFFERENT TISSUES OF ARABIDOPSIS Northern blot analysis of cel1 was carried out using the 768-by cel1 cDNA fragment as a probe (FIG. 6). RNA transcripts were undetectable in fully expanded leaves, as well as at the basal internode of flowering stems of normal *A. thaliana* plants. However a strong transcript signal was detected in the elongating zone of flowering stems of normal plants. *A. thaliana* plants that were treated with uniconazole produced dwarf plants. The level of cel1 RNA transcript in the elongating zone of dwarf flowering stems was significantly lower than that in the normal plants (FIG. 6). Densitometry analysis of northern blots from three independent experiments revealed a 2–5 fold difference between the transcript levels of nominal versus dwarf plants.

11. EXAMPLE: HISTOLOGICAL GUS STAINING ANALYSIS OF TRANSGENIC PLANTS

Figure 7A:
Figure 7B:
Figure 7C:
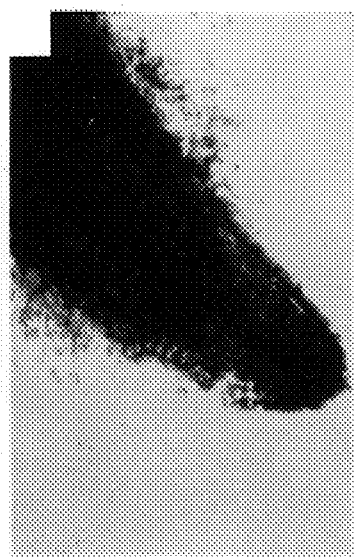

Transgenic tobacco plants transformed with the putative cel1 promoter region (nucleotides 5–1618, SEQ ID NO:1) fused to the gus reporter gene in the pBI101 binary expression vector (Clontech, Palo Alto, Calif.), were tested for tissue-specific expression. Significant GUS activity was observed in sixteen seedlings that were generated from eight independent transgenic plants. Staining was observed both in shoot and root elongating zones (FIGS. 7A–C). Young leaves, although to a less extent, were also stained (not shown). Control transgenic plants containing the same construct without the putative cel1 promoter region, did not show any GUS staining.

12. EXAMPLE: CONSTRUCTION OF cbd TRANSGENIC TOBACCO PLANTS

Figure 9:
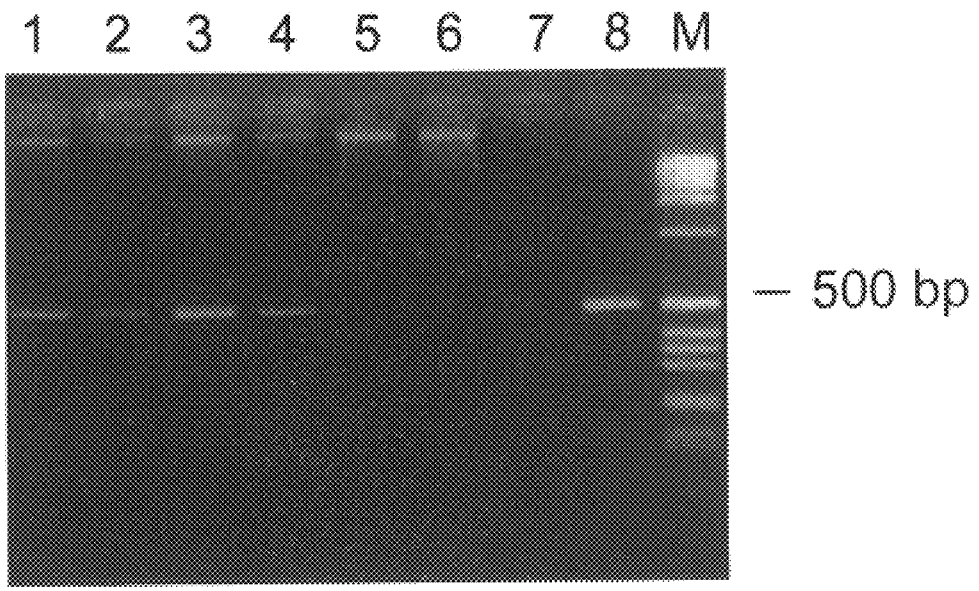
Figure 10:
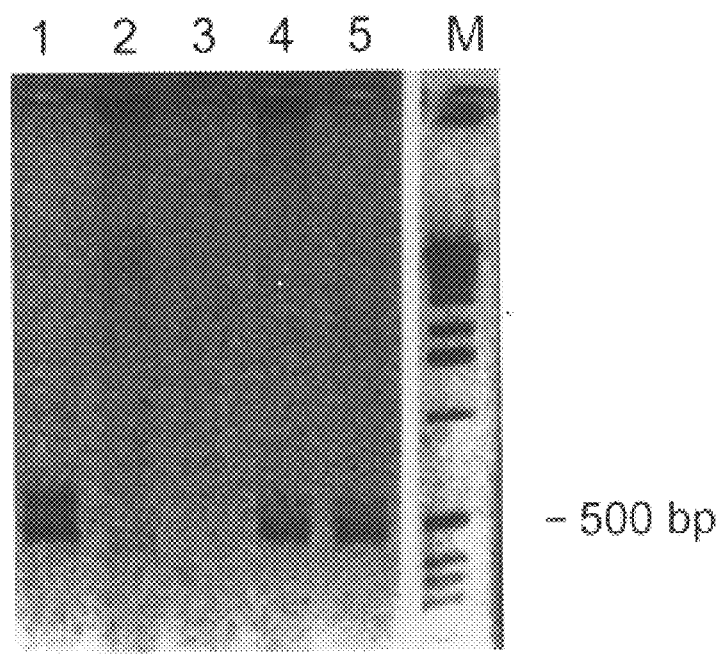

Fifteen to twenty independent transgenic tobacco plants ($F_0$, parental generation) were prepared from each one of the vectors pCCI, p35SCI and pBI101. pBI101 served as a negative control as it does not encode for cbd. Conformation of the presence of a transgene was conducted by PCR analysis (see, for example, FIG. 9), Southern blot analysis (not shown), and kanamycin resistance. The results indicated the presence of a single copy of the cbd construct in the $F_0$ generation for both the pCCI and p35SC1 constructs, and of at least two copies for the pBI101 in the control plants. Transcription of cbd in both PCCI and p35SC1 transgenic plants was confirmed by RT-PCR analysis (see, for example, FIG. 10).

Figure 11A:
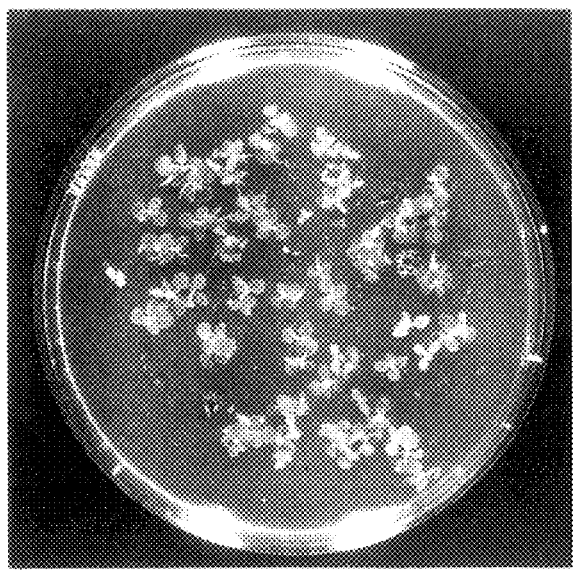
Figure 11B:
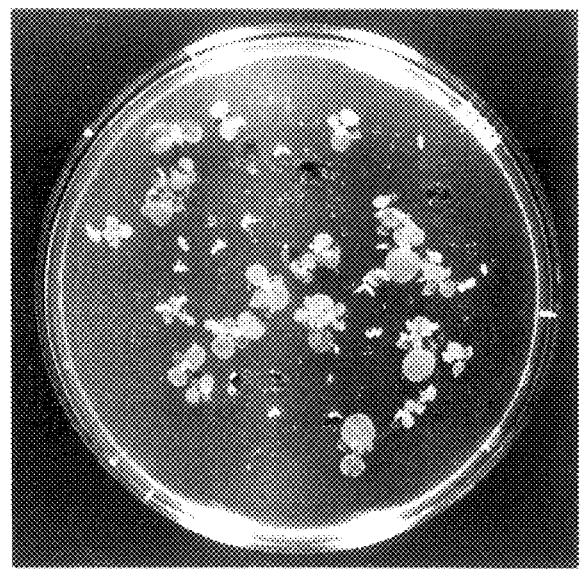

$F_1$ transgenic tobacco plants transformed with either pCCI or p35SC1 (the latter are shown in FIG. 11B) displayed great size variation. As shown in FIG. 11A, the $F_1$ control plants transfected with pBI101 showed very moderate variation. In the latter case no kanamycin sensitive plants were observed, indicating the presence of more than a single active copy of the transgene, each of the copies independently segregates.

$F_1$ transgenic tobacco plants of a parent transformed with a single copy of either pCCI or p35SC1 segregated into three distinct phenotypes. About a quarter of the $F_1$ plants were kanamycin sensitive, indicating absence of the transgene. An additional quarter of the plants had a small phenotype, whereas about half of the plants had a large phenotype. The two later segregates further exhibited phenotypic variation. Among the small plants, some exhibited distorted hypocotyls at the early stages of germination. Among the large plants, variation was from normal size (as compared to kanamycin grown pBI101 control transgenic plants) to giant size. Collectively, these results indicate that the kanamycin sensitive plants were homozygous for the absence of the transgene, the large plants were hetererozygotes, whereas the small plants contained two active copies of the transgene. These results are in very good correlation with the report (PCT Publication WO 94/24158) demonstrating that high concentrations of cbd protein inhibit plant growth in vitro, whereas, moderate concentrations accelerate plant growth. When grown without kanamycin, $F_1$ transgenic tobacco plants transformed with either pCC1 or p35SC1 segregated into the large and small phenotypes. Under these growth conditions, the kanamycin sensitive plants could not be distinguished from the subpopulation of heterozygous normal size plants of the large phenotype. These results confirm that cbd genotype is responsible for the observed phenotypes, i.e., expression of cbd in transgenic plants modulates their growth.

Figure 12A:
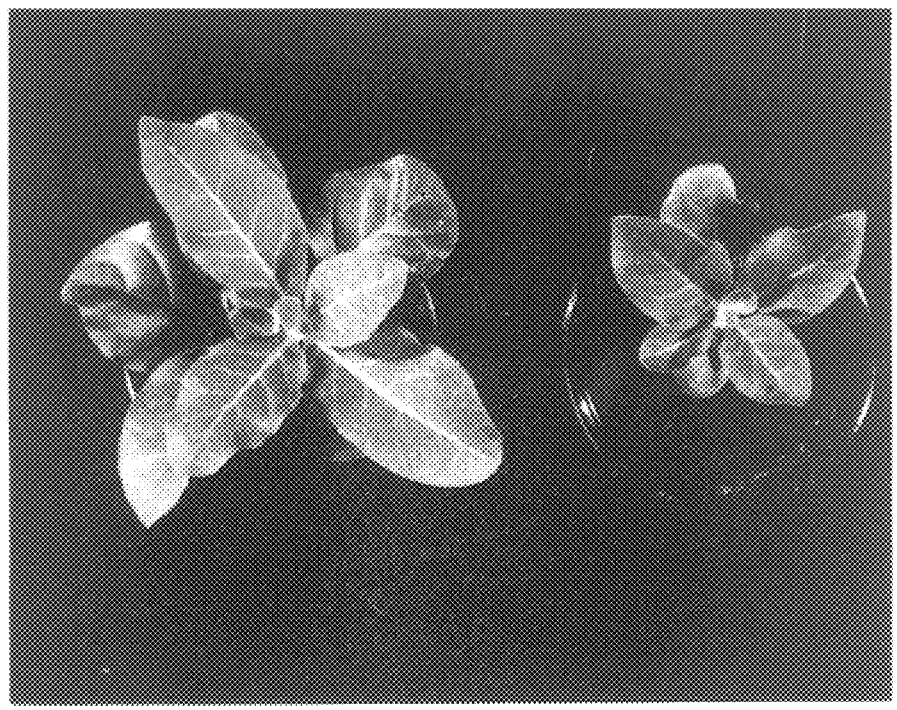
Figure 12B:

The difference in size among the phenotypically distinct groups (large and small) was also maintained after maturation (FIG. 12).

Figure 13A:
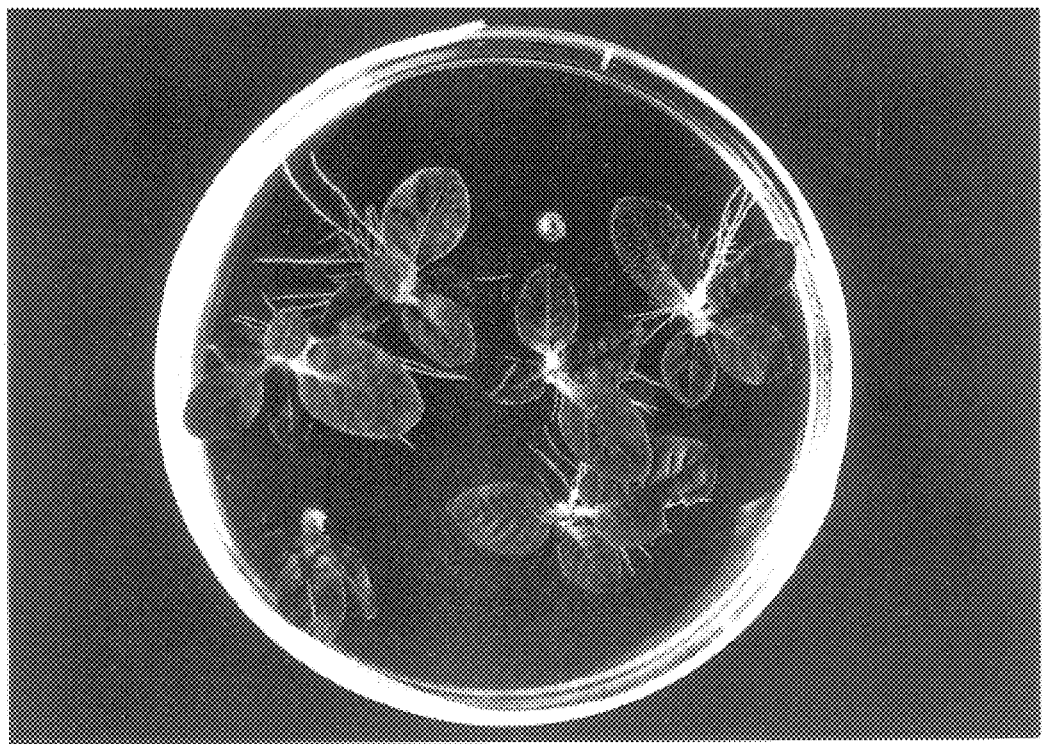
Figure 13B:
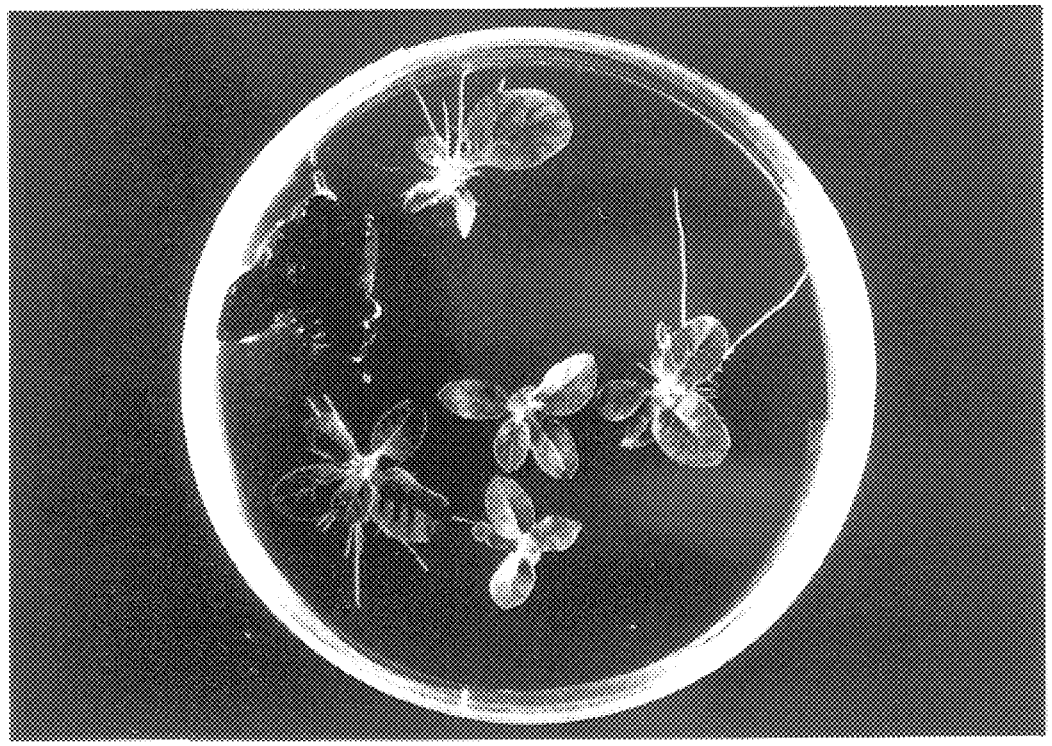
Figure 14A:
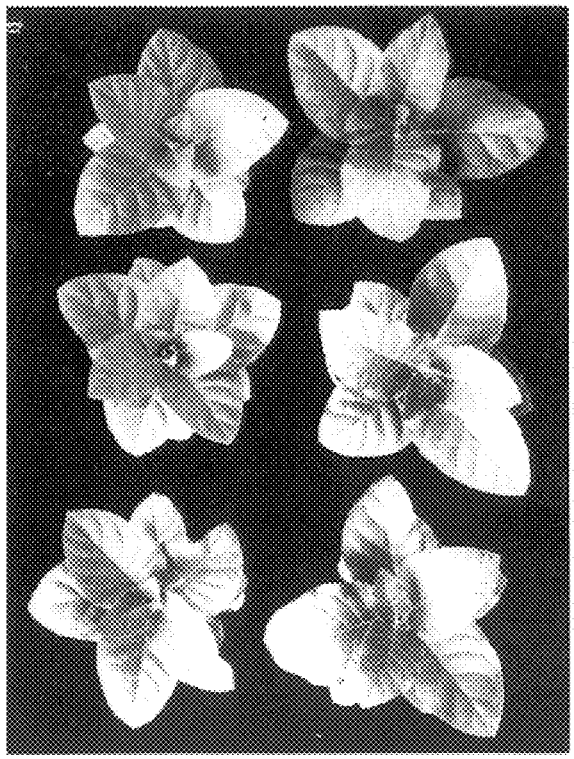
Figure 14B:
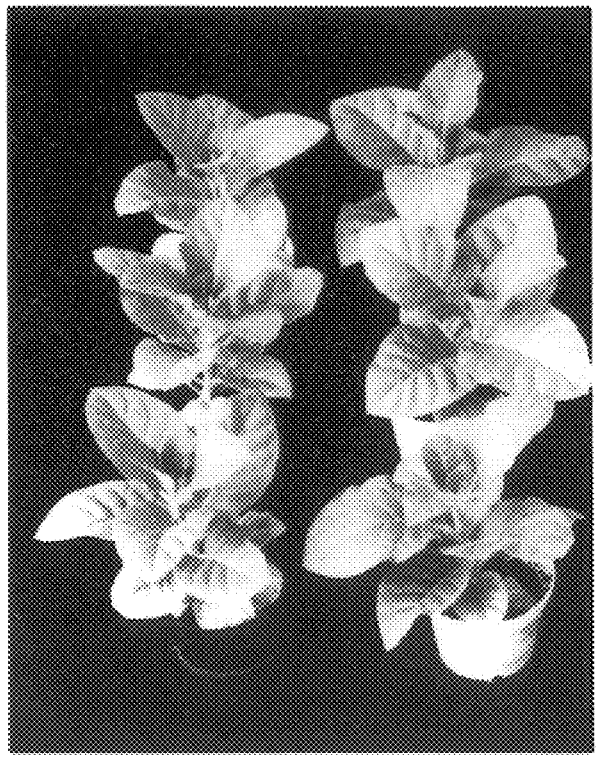
Figure 15A:
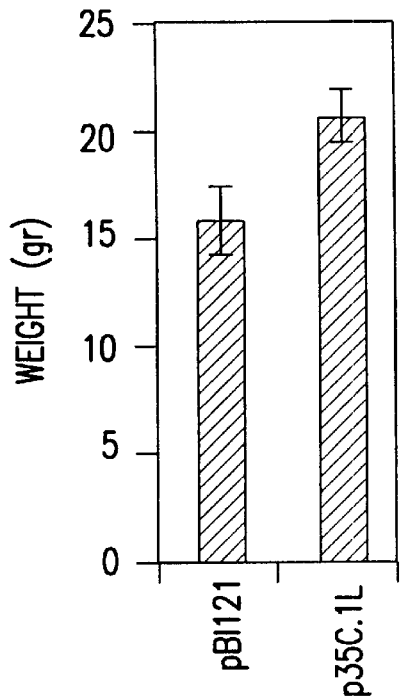
Figure 15B:
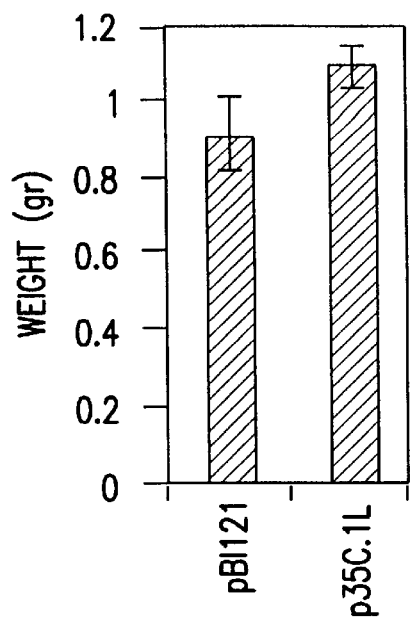
Figure 15C:
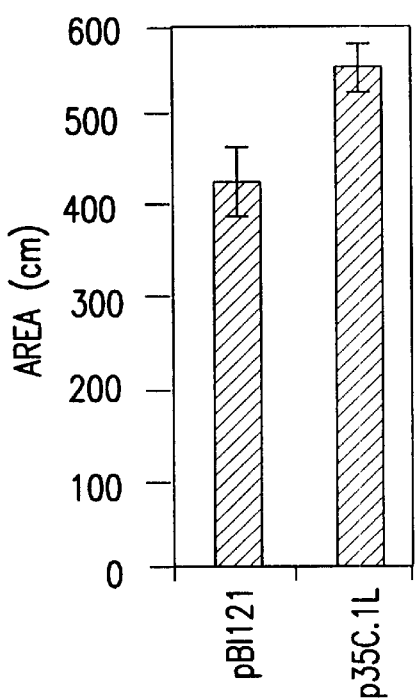
Figure 15D:
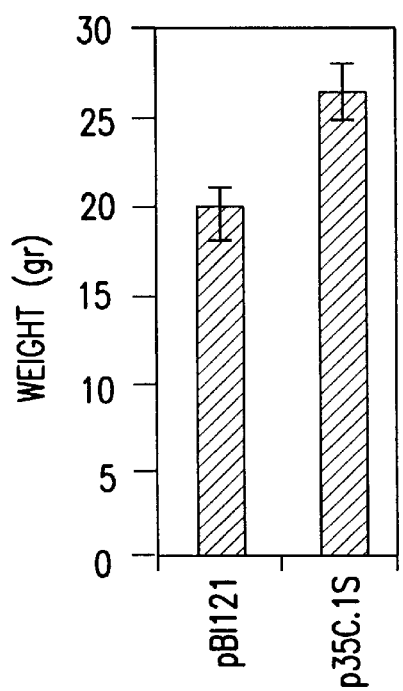
Figure 15E:
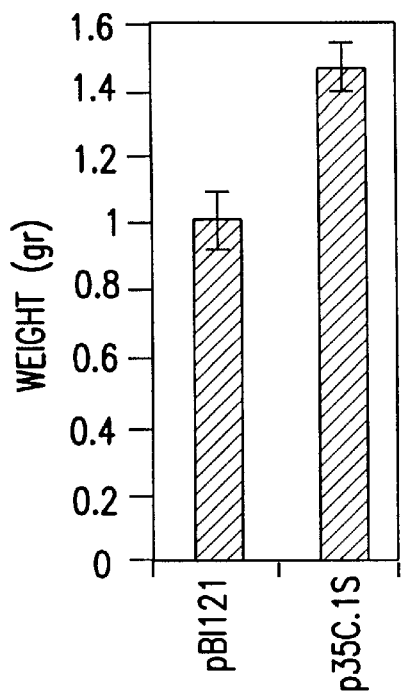
Figure 15F:
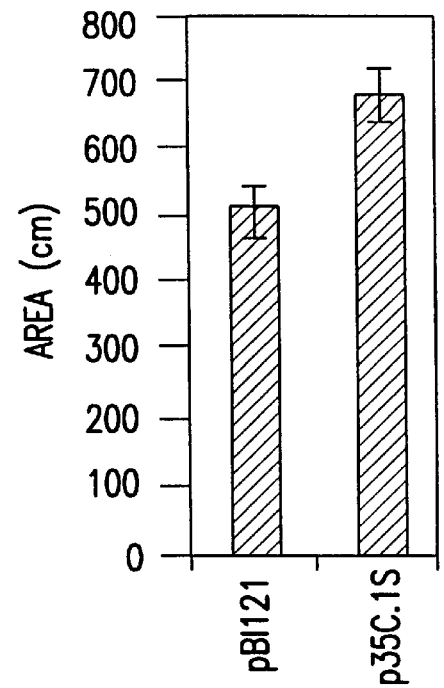

Furthermore, transgenic plants that were vegetatively propagated maintained their phenotype while young (FIG. 13) as well as in a later stage of their vegetative development (FIG. 14). These results demonstrate that cbd transgenic plants exhibiting an altered growth phenotype, maintain the altered phenotype even when vegetatively propagated.

13. EXAMPLE: BIOMASS PRODUCTION OF TRANSGENIC PLANTS EXPRESSING cbd

Figure 16A:
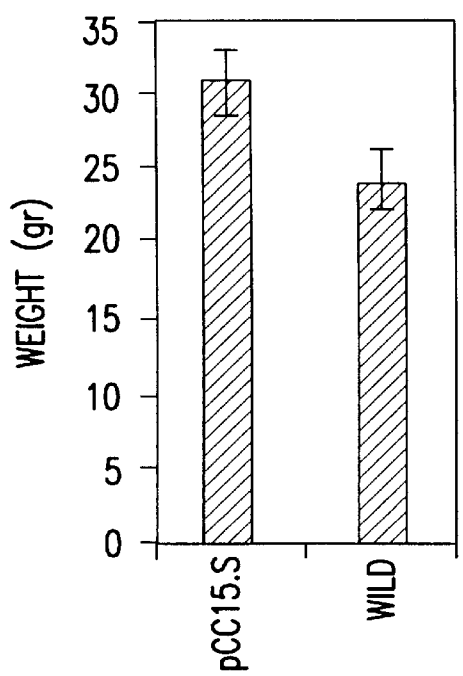
Figure 16B:
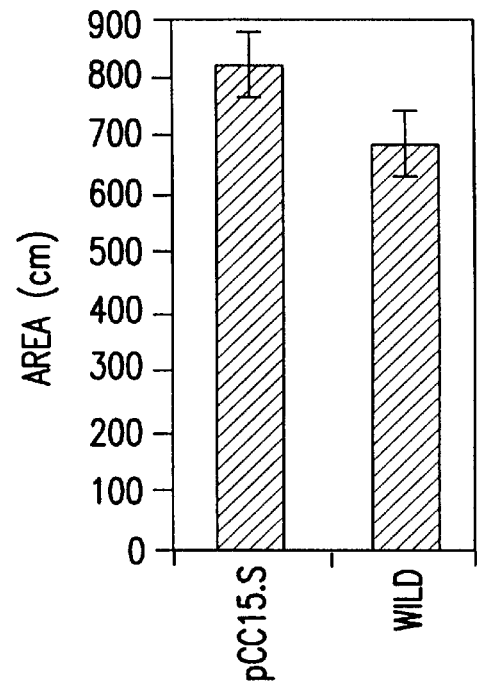

Tobacco $F_1$ plants of p35SC1 (cbd expressed under 35S promoter) and control plants transformed with pBI121 (Clontech Inc., Palo Alto, Calif.) were germinated on plates and grown for 4 weeks. The two specific phenotypes generated by cbd expressing transgenes (large leaves/normal hypocotyl and small leaves/long hypocotyl) and large and small seedlings of control plants were selected and transferred to fresh medium and grown for additional 3–4 weeks in the growth room and then transferred to the green house for 3–4 weeks. Leaf area, wet and dry weight of the plants was measured. The results indicate that cbd-transgenic plants produce significantly more biomass as compare to the control plants (FIG. 15). Similar results were obtained with $F_1$ tobacco plants transformed with pCC1 (CBD expression controlled by the cel1 promoter) (FIG. 16).

14. EXAMPLE: cel1 PROMOTER EXPRESSION IN ASPEN (POPULUS TREMULA)

14.1. MATERIALS AND METHODS

14.1.1. CONSTRUCTION OF TRANSGENIC PLANTS EXPRESSING cel1 PROMOTER-gus FUSION The 1.6 kb cel1 promoter region (nucleotides 5–1618 of accession #X98543 (SEQ ID NO:9)) was cloned into the binary vector pBI101.1 at the 5' end of the β-glucoronidase gus gene. The construct was mobilized into disarmed EHA101 *Agrobacterium tumefaciens* by triparental mating (An, 1987, Meth. Enzymol. 153:292–305). The transformation was performed with stem explants of *Populus tremula* (Tzfira et al., 1997, Physiologia Plantarum 99:554–561). Regenerated transgenic plants were selected on kanamycin. Eleven plants that were independently transformed with the construct were tested. The plants were analyzed for the presence of the cel1 promoter region by Southern blot analysis. Transgenic poplar plants were grown in the growth chamber at 25° C. under a 16 hr photoperiod.

14.1.2. HISTOLOGICAL GUS STAINING ANALYSIS OF TRANSGENIC PLANTS

GUS staining was performed with X-Gluc as previously described (Jefferson et al., 1987, EMBO J. 6:3901–3907). Thirty day old seedlings were incubated overnight with X-Gluc at 37° C. and then kept in a 70% ethanol solution prior to taking a photograph.

14.2. Results

Figure 17:
FIG. 17 shows the expression of cel1-gus in Poplar.
Figure 18:
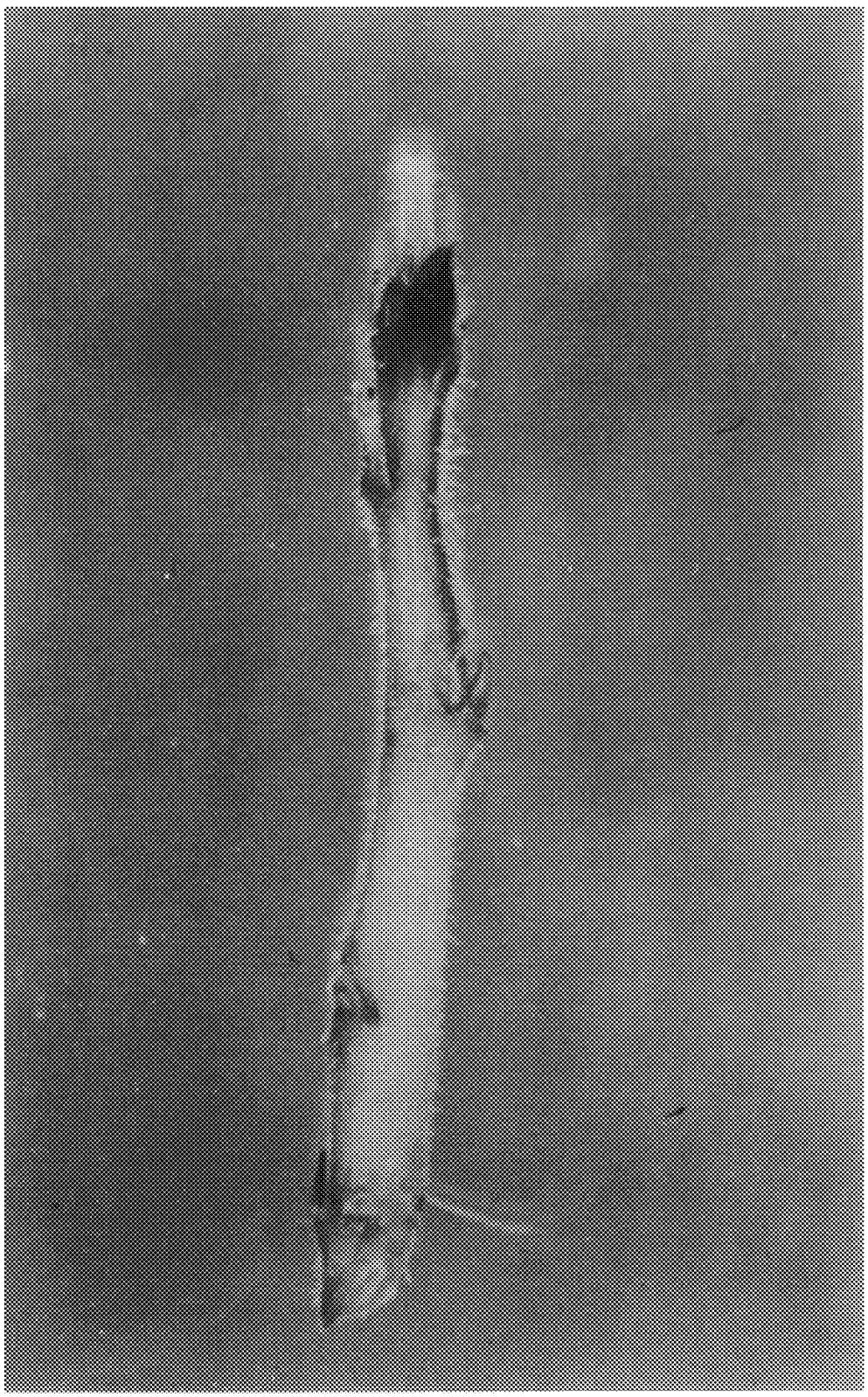
FIG. 18 shows the expression of cel1-gus in a Poplar shoot.
Figure 19:
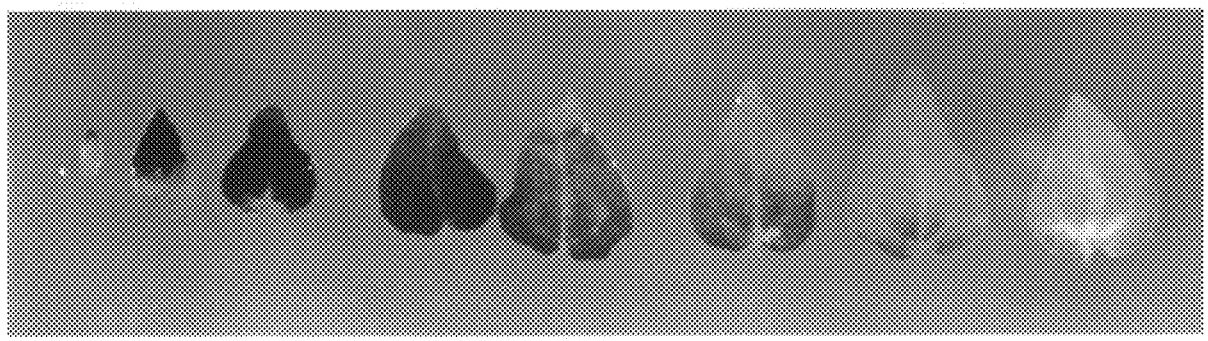
FIG. 19 shows the expression of cel1 promoter-gus in leaves transformed Poplar plants.

The GUS staining indicated specific expression of the cel1 promoter in fast growing tissues such as young leaves and the elongation zone of the stem as shown in FIGS. 17 and 18. The blue staining pattern correlated with the natural growth pattern of the cells in the developing leaves as shown in FIG. 19.

These results together with the results presented in Examples 11 and 17 show the cel1 promoter directs tissue specific expression of GUS in growing organs of different transgenic plants such as Poplar, tobacco (see Example 11, supra) and Arabidopsis (see Example 17, infra).

15. EXAMPLE: EXPRESSION OF cbd IN POPLAR

Figure 20:
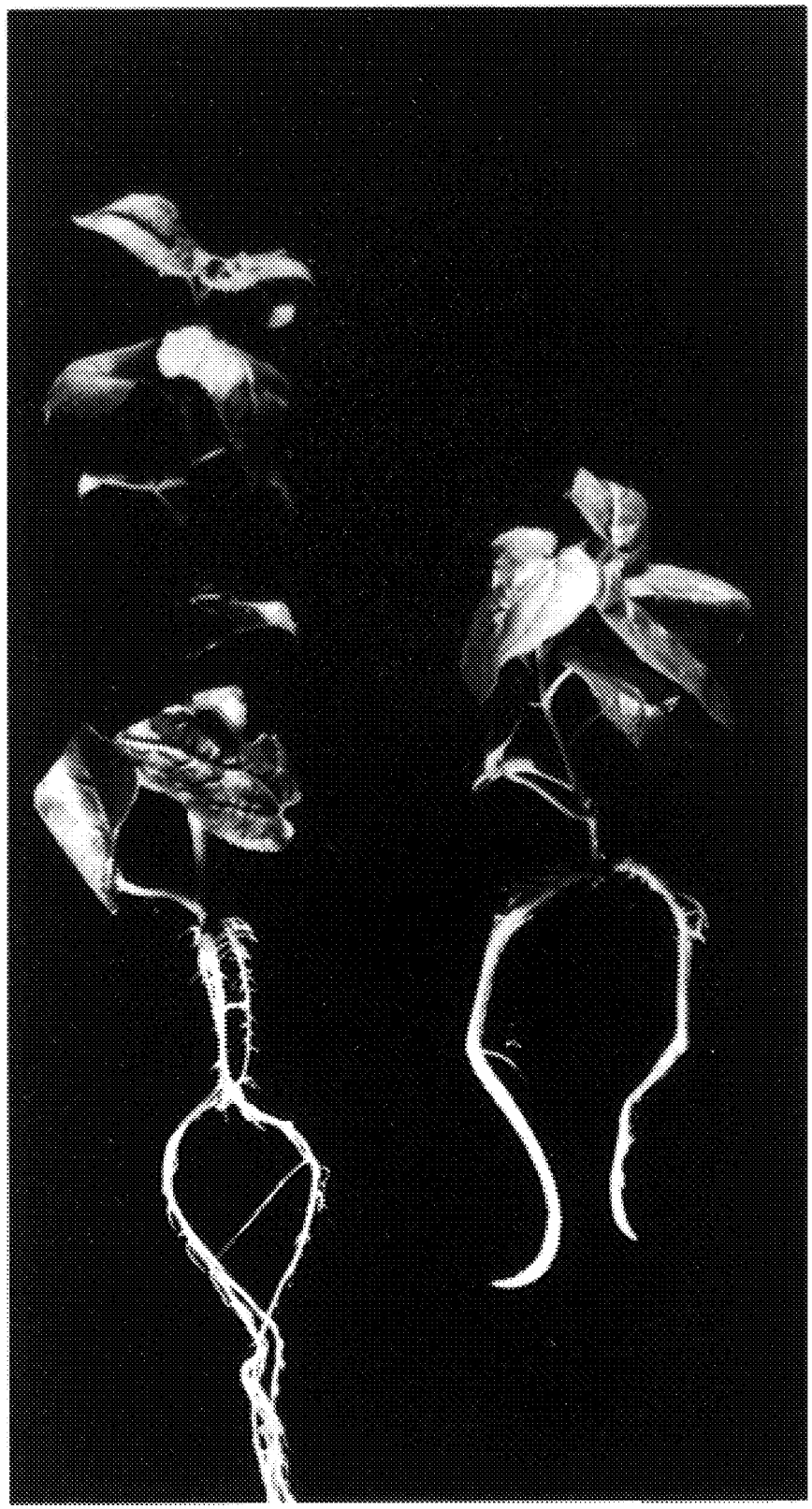
FIG. 20 shows the altered structural morphology of a transgenic Poplar plant expressing the cbd gene under control of the CaMV 35 promoter (right) as compared to the control untransformed Poplar plant (left).
Figure 21:
FIG. 21 shows leaves from transgenic Poplar plants expressing the cbd gene under control of the CaMV 35S promoter (bottom) as compared to leaves of a control plant (top).
Figure 22:
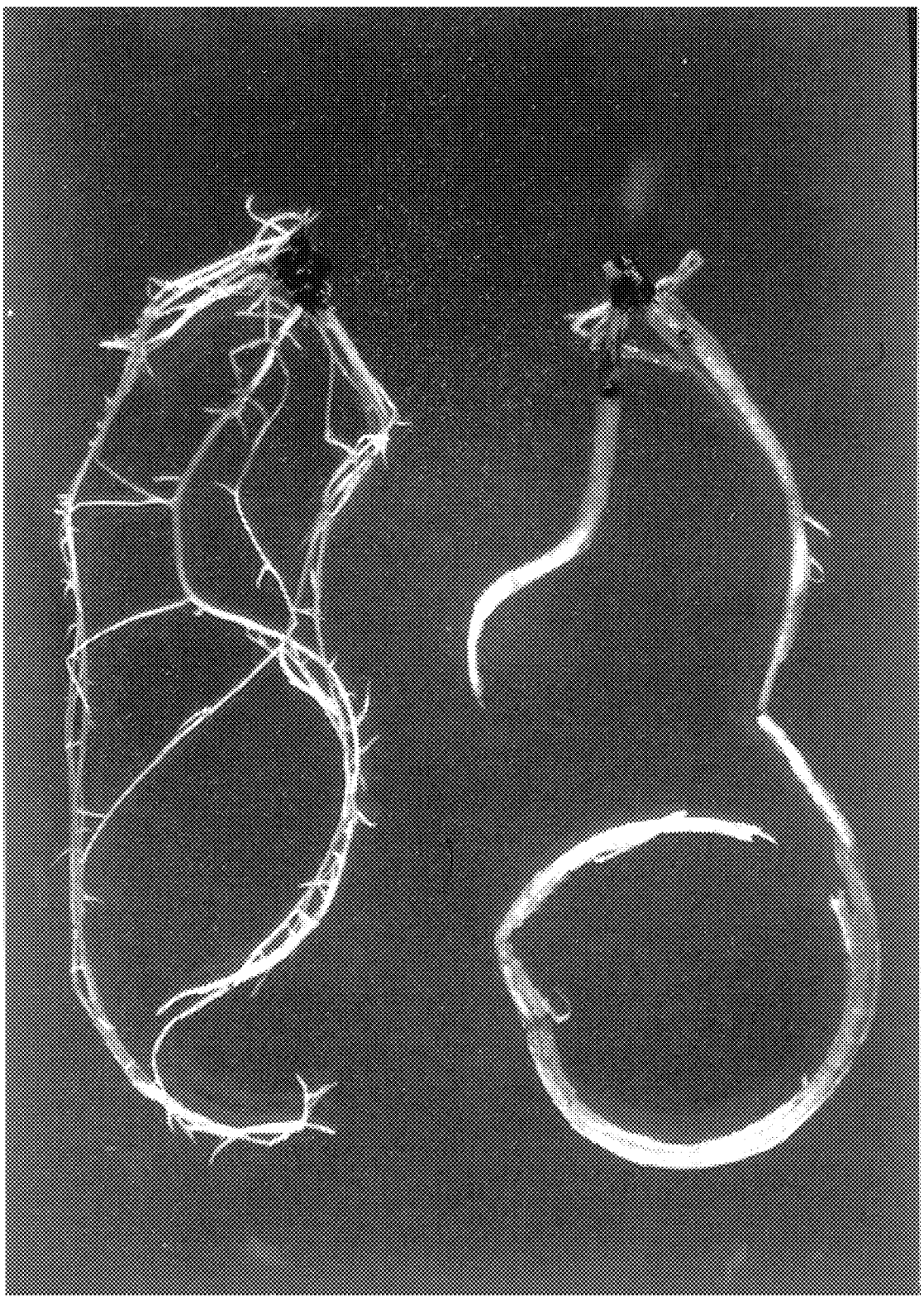
FIG. 22 shows roots from transgenic Poplar plant expressing the cbd gene under control of the CaMV 35S promoter (right) compared to roots of a control plant (left).
Figure 23:
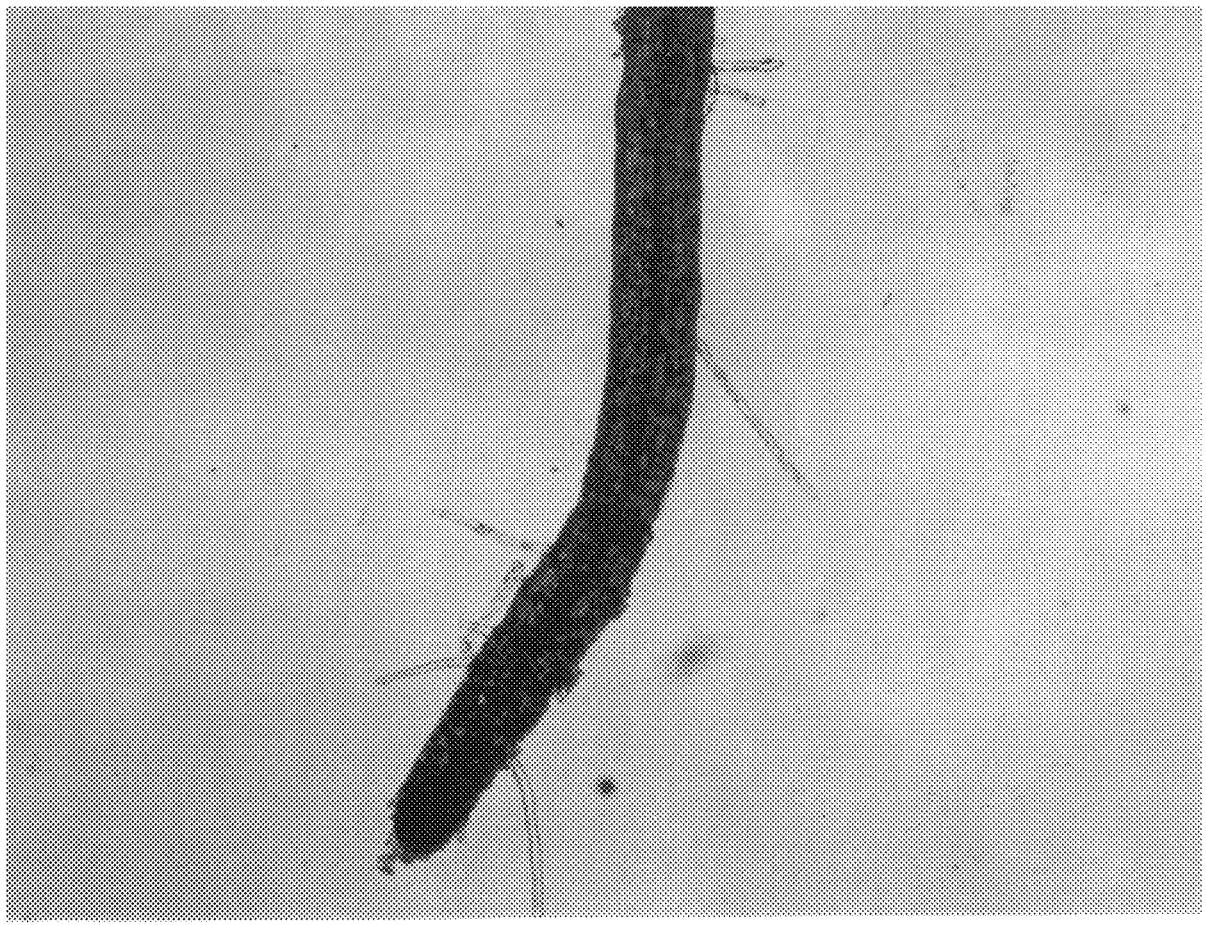
FIG. 23 is a photograph of the root tip of a control poplar plant (40× magnification).
Figure 24:
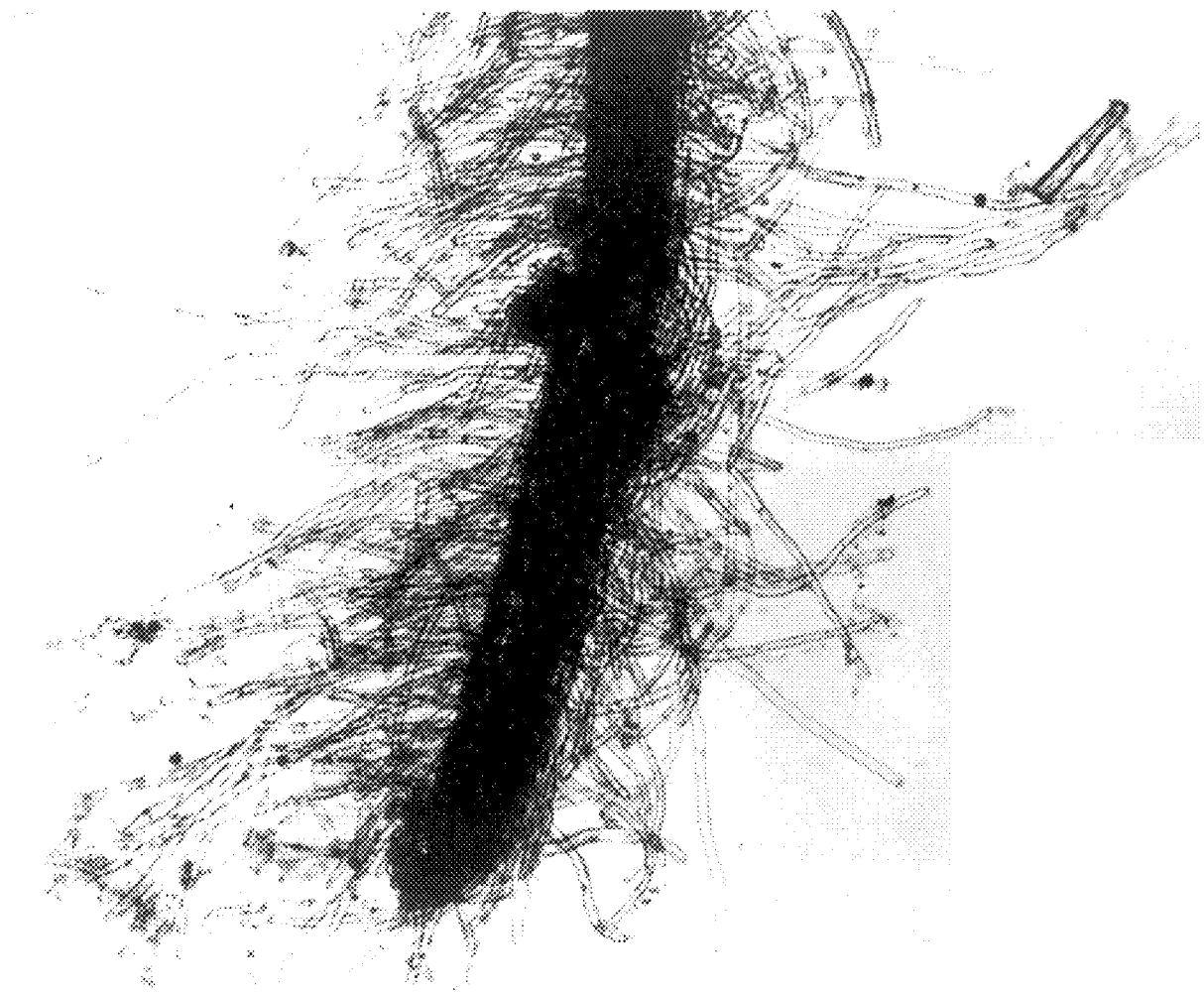
FIG. 24 is a photograph of the root tip of a transgenic poplar plant expressing the cbd gene under the CaMV 35S promoter (40× magnification).
Figure 25:
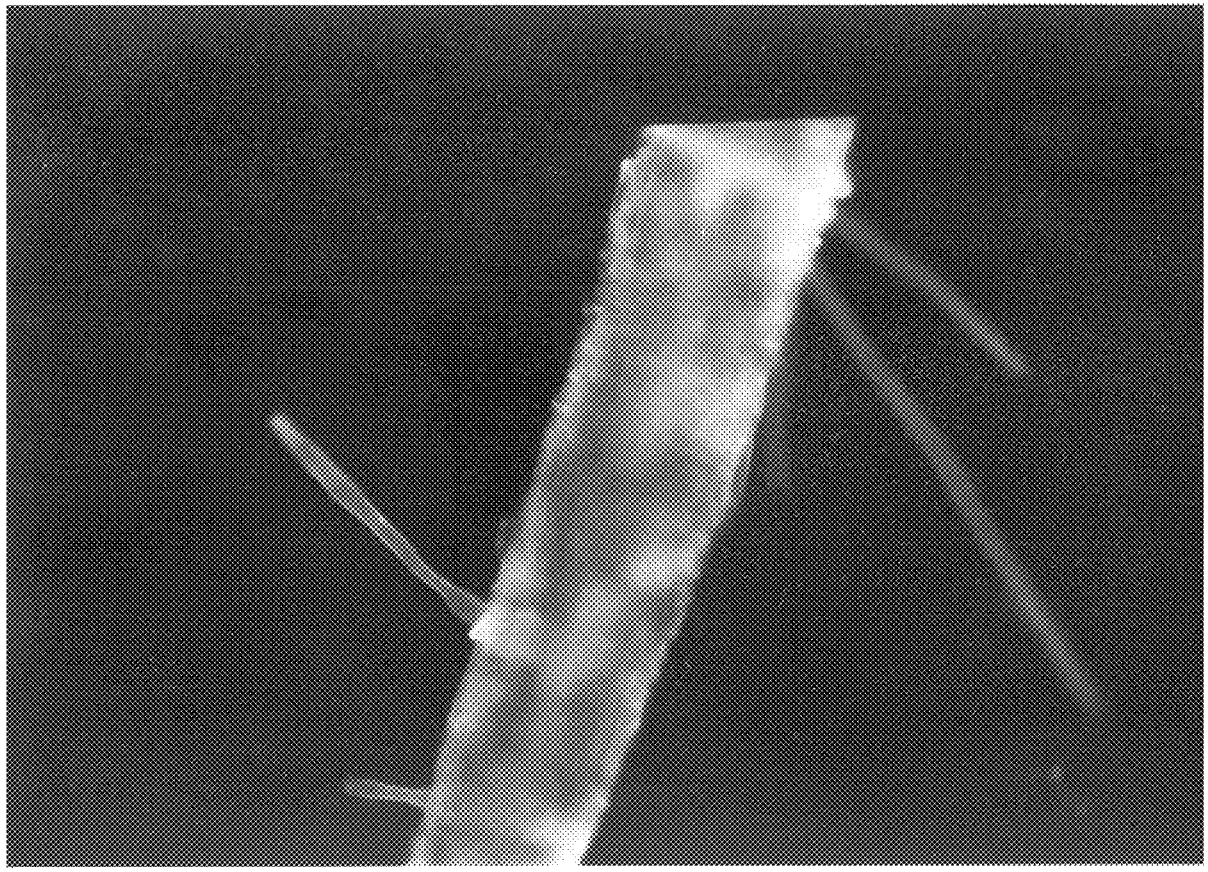
FIG. 25 is a photograph of a calcofluor staining of a root from an untransformed control poplar plant (400× magnification).
Figure 26:
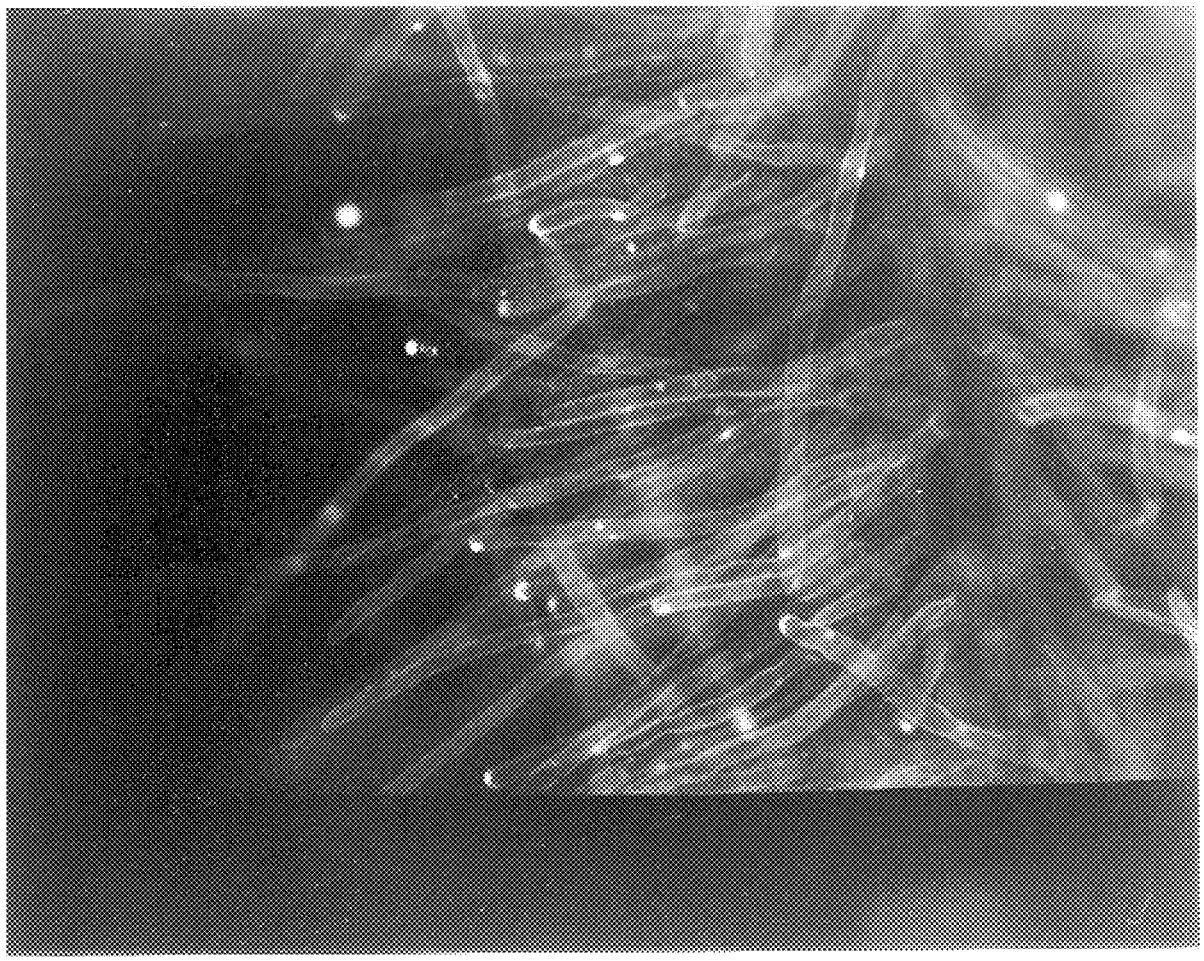
FIG. 26 is a photograph of a calcofluor staining of a root from a transgenic poplar plant expressing the cbd gene under control of the CaMV 35S promoter (100× magnification).
Figure 27:
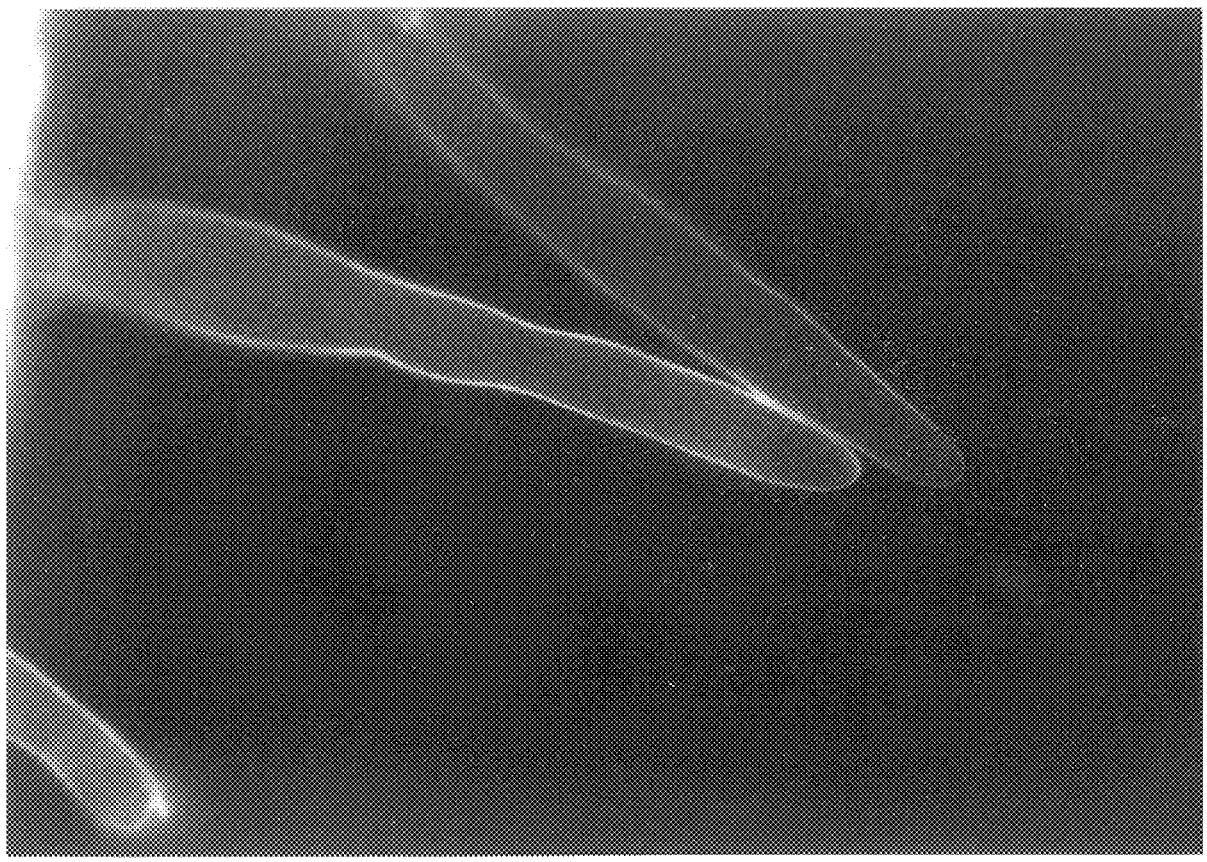
FIG. 27 is a photograph of the calcofluor staining of a root hair from an untransformed control poplar plant (400× magnification).
Figure 28:
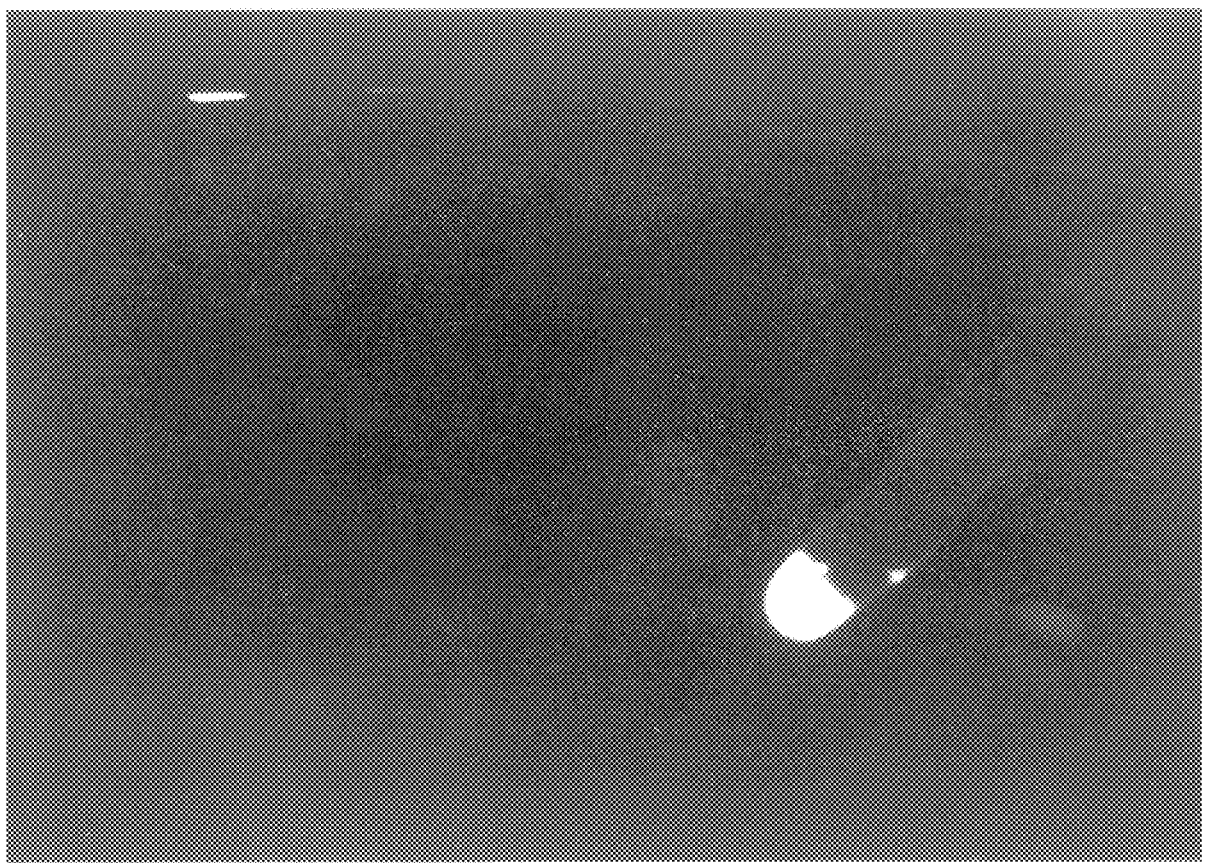
FIG. 28 is a photograph of calcofluor staining of a root hair from a transgenic poplar plant expressing the cbd gene under the control of CaMV 35S promoter (400× magnification).
Figure 30:
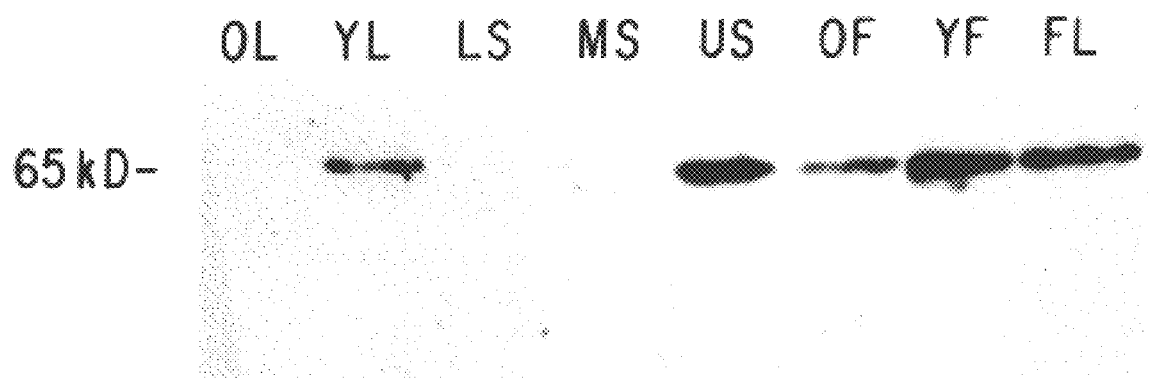
FIG. 30 is a photograph of a Western blot analysis of CELL protein in Arabidopsis tissues. Old leaf (OL), young leaf (YL), lower stem (LS), middle stem (MS), upper stem (US), old fruit/pod (OF), young fruit/pod (YF), flower (FL).

Poplar plants expressing cbd under the CaMV 35S promoter showed a distinct phenotype (FIG. 20). The plants had shorter stature but with larger leaves compared to the control plants (FIG. 21). The roots appeared significantly thicker and were covered with many more root hairs that were more dense and longer than the control plants (FIGS. 22–24). Calcofluor staining showed that these plants accumulated cellulose at the tip zone of many of the root hairs indicating that cbd increased the rate of synthesis of the cellulose (FIGS. 25–28). This observation is in agreement with the in vitro experiments that showed that cbd accelerates the rate of synthesis of cellulose as shown in FIG. 30.

16. EXAMPLE: TRANSGENIC POPLAR PLANTS EXPRESSING cel1

Figure 29:
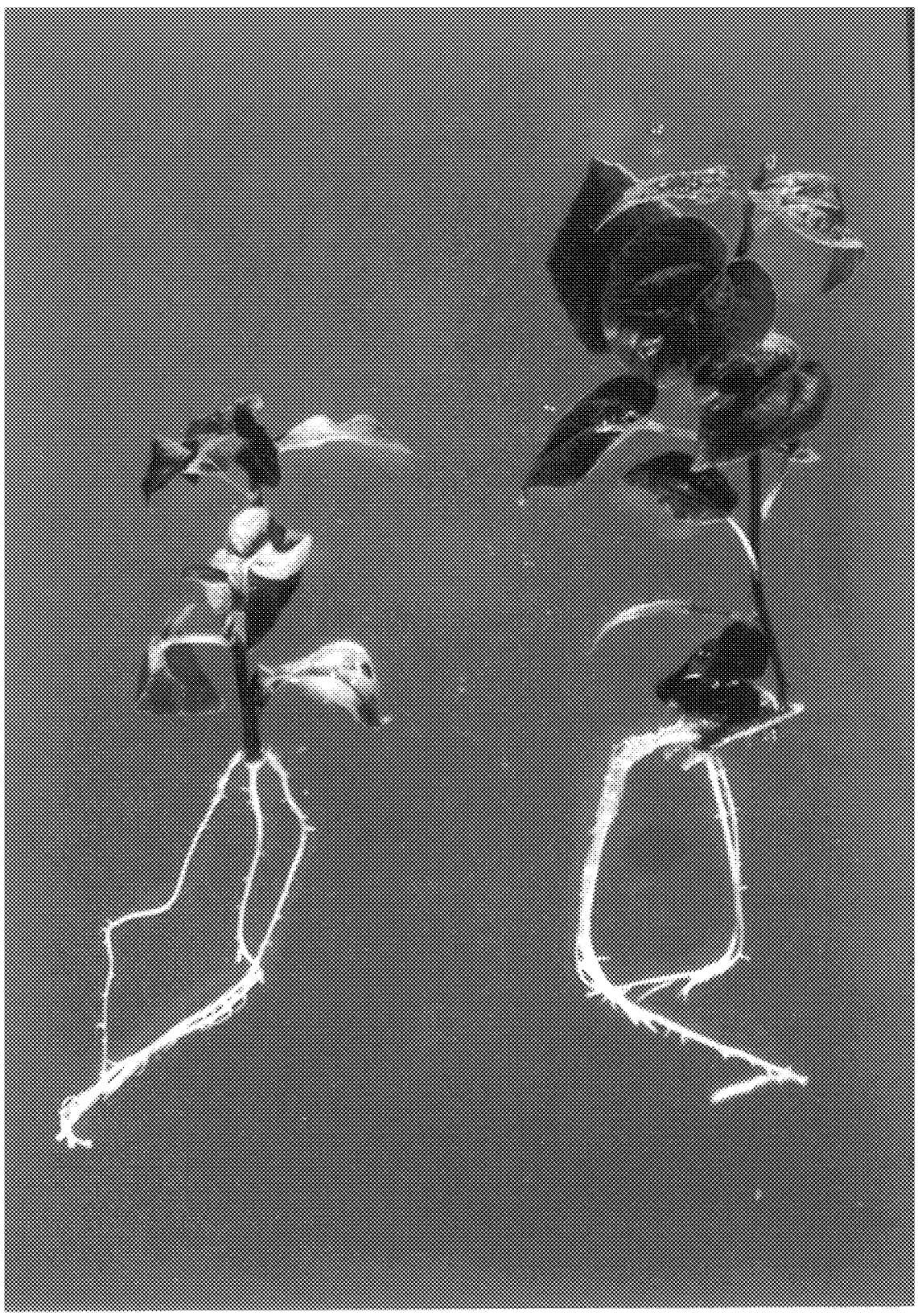
FIG. 29 is a photograph of a transgenic poplar plant expressing the cel1 gene under control of the CaMV 35S promoter (right) and a control plant (left).

Six independent transgenic poplar plants (out of 10) expressing cel1 under the CaMV 35S promoter showed a distinct phenotype (FIG. 29). These plants appear to be larger compared to the control plants (transformed with the vector containing gus under the CAMV 35S promoter).

17. EXAMPLE: cel1 EXPRESSION IN ARABIDOPSIS

The cDNA of cel1 was cloned into the E. coli expression vector pET3d (Novagen, Madison, Wis.). The recombinant protein was used to produce polyclonal antibodies in rabbits. The specific antibodies reacted with a 65 kD protein. This protein was detected only in fast growing organs and was not found in old or fully developed tissues (FIG. 30).

18. EXAMPLE: THE EFFECT OF CBD ON CELLULOSE SYNTHESIS IN ACETOBACTER XYLINUM

18.1. INTRODUCTION

The gram-negative bacterium Acetobacter xylinum has long been regarded as a model of cellulose synthesis because cellulose microfibril synthesis is separated from cell wall formation (Ross et al. 1991, Microbiological Reviews 55:35–58). Since polymerization and crystallization are coupled processes in A. xylinum cellulose synthesis, interference with the crystallization results in an acceleration of polymerization (Benziman et al. 1980, Proc. Natl. Acad. Sci. USA 77:6678–6682). Some cellulose-binding organic substances can also alter cell growth and cellulose-microfibril assembly in vivo. For example, direct dyes, carboxymethyl cellulose (CMC) and fluorescent brightening agents (FBAs, e.g., calcofluor white ST) bind to the polysaccharide chains immediately after their extrusion from the cell surface, preventing normal assembly of microfibrils and cell walls. These molecules prevent microfibril crystallization, and therefore enhance polymerization. (Haigler, 1991, "Relationship between polymerization and crystallization in microfibril biogenesis," in: Biosynthesis and Biodegradation of Cellulose, pp. 99–124, eds C. H. Haigler and P. J. Weimer, arcel Dekker, Inc., New York).

This experiment was conducted to determine the effects of cbd expression on cellulose synthesis.

18.2. MATERIAL AND METHODS

Aectobacter xylinum strain ATCC 23769 was used. Cells ere grown for 24 hr in constant shaking at 30° C. in a medium consisting of 0.5% Bactopeptone, 0.5% Yeast extract, 2% glucose and 0.3% $K_2HPO_4$ pH 6, and 1.5 Unit/ml Trichoderma viride cellulase (Fluka, Buchs, Switzerland). The cells were harvested by centrifugation and washed twice with pre-cooled phosphate buffer (50 mM $NaH_2PO_4$ pH 6). The bacterial pellet was resuspended in phosphate buffer to a concentration of 2 mg/ml dry weight (2.5 $O.D_{600}$=1 mg/ml). One ml of each of the reaction mixtures was placed in 20 ml scintillation vials containing 0.8 mg cells/ml phosphate buffer. Cellulose synthesis was initiated by the addition of 40 mM glucose (D-$[U^{14}C]$ glucose (Amersham, England) at a specific activity of 40,000 cpm/μmol and allowed to occur for 1–2 hr at 30° C. with constant shaking. The $^{14}CO_2$ formed was trapped in coverless Ependorf tubes containing 0.2 ml 1 M NaOH placed in the reactions vial. The reaction was stopped by the addition of 0.1 ml of 0.5 M HCl to the bacterial suspension and incubated for 15 min. One hundred and fifty μl of the NaOH solution containing the trapped $^{14}CO_2$ were transferred to scintillation tubes. The cells and the cellulose were transferred to 1.5 ml Ependorf tubes, centrifuged and washed three times with water. The cells were lysed by mixing with 0.2 N NaOH, 1% SDS. Cellulose was recovered on GF/A filter (Whatman, Shrewsbury, Mass.) washed with 15 ml of water and dried in an oven at 60° C. Filters and NaOH containing trapped $^{14}CO_2$ were counted in a scintillation counter using "OPTI-FLUOR" (Packard) scintillation liquid to measure glucose incorporation (cellulose synthase activity) and respiration.

Electron microscopy was conducted by placing a drop of the appropriate solution on top of a copper grid at room temperature. The cellulose synthesis reaction contained 0.5 mg/ml dry weight cells in phosphate buffer, 40 mM glucose with or without CBD at a concentration of 300 μg/ml. The reaction was incubated for 30 min and then stopped with 2.5% glutardialdehyde (Merck, Rahway, N.J.) for 30 min, washed three times with water and dried. The grids were negatively stained with 1.5% phosphotungstic acid and examined with a Jeol 100 CX electron microscope operating at 80 kV.

18.3. RESULTS

Resting cells of Acetobacter xylinum were allowed to synthesize cellulose in phosphate buffer containing radioactive glucose and different concentrations of cbd or calcofluor (as a positive control) and BSA (as a negative control) for 1 hr or for the indicated length of time. Cellulose synthase activity was determined by the amount of glucose incorporated. FIG. 30 shows the effect of cbd at different concentrations (10–500 μg/ml, 0.6–30 μM) compared with 1 mM calcofluor and 100 μg/ml BSA (1.5 μM). The cbd increased glucose incorporation in a dose responsive manner by up to five-fold at 500 μg/ml. Calcofluor increased the rate by two-fold while BSA had no effect. The rate of glucose oxidation to $CO_2$ was only marginally affected. Thus, glucose incorporation could be attributed to cellulose synthesis.

Electron microscopy examination of the cellulose ribbons produced by A. xylinum showed that CBD treatment resulted in a splayed ribbon composed of separate fibrillar subunits as compared with a thin and uniform ribbon in the control as shwon in FIG. 31.

This example demonstrates, using the model system (Acetobacter xylenum), that cbd enhances cellulose synthase activity, comparable with the effect of the fluorescent brightening agent calcofluorwhite. The effect of cbd on cellulose synthase activity was dose-responsive with an optimum response around 10 mg/ml.

18.4. DISCUSSION

It is evident that polymerization and crystallization are coupled reactions in cellulose synthesis in Acetobacter xylinum bacteria (Benziman et al., 1980 Proc. Natl. Acad. Sci. USA 77:6678–6682). Addition of cbd to the culture medium enhanced the incorporation of radioactive glucose in A. xylinum. While not intending to be limited to any particular mechanism of action on cellulose synthesis, the present inventors believe that cbd enhanced incorporation of radioactive glucose by interfering with the cellulose crystallization process. Our hypothesis is supported by Haigler's review (1991, "Relationship between polymerization and crystallization in microfibril biogenesis," in: Biosynthesis and Biodegradation of Cellulose, pp. 99–124, eds Haigler and Weimer, Marcel Dekker, Inc., New York), in which dyes and fluorescent brightening agents that bind to cellulose were shown to alter cellulose microfibril assembly in vivo. Modifications in cell shape were observed when red alga (Waaland and Waaland, 1975, Planta 126:127–138) and root tips (Hughes and McCully, 1975, EMBO J. 6:3901–3907) were grown in the presence of dyes. It is now evident that these molecules can bind to the cellulose chains immediately upon their extrusion from the cell surface of prokaryotes and eukaryotes (Haigler and Brown, 1979, J. Cell Biol. 83, 70a; Benziman et al., 1980, Proc. Natl. Acad. Sci. USA 77:6678–6682; Haigler et al., 1980, Science 210:903–906;

Brown et al., 1982, Science 218:1141–1142) and prevent crystal-structure formation (Haigler and Chanzy, 1988, J. Ultrastruct. Mol. Struct. Res. 98:299–311). In addition, the rate of cellulose polymerization was shown to increase up to fourfold in the presence of dye (Benziman et al., 1980, Proc. Natl. Acad. Sci. USA 77:6678–6682). Crystallization was proposed to be the bottleneck in this coupled reaction and its prevention to result in accelerated polymerization. The effect of cbd as observed by electron microscopy is comparable to the effect of CMC (carboxy methyl cellulose) rather than to the effect of calcofluor (Haigler, 1991, "Relationship between polymerization and crystallization in microfibril biogenesis," in *Biosynthesis and Biodegradation of Cellulose*, pp. 99–124, eds Haigler and Weimer, Marcel Dekker, Inc., New York) in both cases the cellulose ribbon only splayed. The effect of cbd on cellulose synthase activity was higher than the effect of CMC and was comparable to and even higher than that of calcofluor (FIG. 30). The different effects of cbd, CMC and calcofluor can be attributed to the differences in the molecular weights and the affinities to cellulose. CMC (90 kDa) can only prevent the normal association of larger fibrillar subunits and, therefore, hardly alters crystallization, while the small molecule calcofluor prevents the glucan chain association immediately after its initiation. The size of the cbd is somewhere in between that of calcofluor and CMC. On one hand, it is not small enough to prevent association of very small fibrils as achieved by calcofluor, but on the other hand, its high affinity to cellulose makes it an efficient cellulose intercalating agent which leads to an increase in the rate of cellulose synthesis of up to fivefold.

Based on results presented above, transgenic plants, such as alfalfa for example, expressing any CBD, including but not limited to cbd, will not only have higher level of biomass, but also have cellulose more amenable for degradation by ruminants and, therefore, have a higher nutritional value than normal non-transgenic plants.

19. DEPOSIT OF PLASMIDS

The following plasmids were deposited with the American Type Culture Collection (ATCC), 10801 University Boulevard, Manassas, Va. on Jan. 12, 1998, and have been assigned the indicated accession numbers:

| Plasmid | Accession Number |
| --- | --- |
| pPS | 209577 |
| pCEL1 | 209576 |

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

The present application claims priority benefits of Israeli application No. 121404, filed Jul. 27, 1997, the disclosure of which is incorporated herein by reference in its entirety. Various publications are cited herein, the disclosure of which are incorporated by reference in their entireties.

What is claimed is:

1. An isolated nucleic acid molecule containing a nucleotide sequence encoding a Cel1 protein or polypeptide of *Arabidopsis thaliana*.

2. The isolated nucleic acid molecule of claim 1 containing a nucleotide sequence encoding a protein or polypeptide having the amino acid sequence of SEQ ID NO:4.

3. A variant of the nucleic acid molecule of claim 1, wherein said variant is an *Arabidopsis thaliana* allelic variant, or a naturally occurring or man-made functional variant encoding an *Arabidopsis thaliana* cell protien or polypeptide.

4. An isolated nucleic acid molecule having the nucleotide sequence of SEQ ID NO:2.

5. An isolated nucleic acid molecule containing a nucleotide sequence encoding a polypeptide having the amino acid sequence of SEQ ID NO:4.

6. A recombinant nucleic acid vector comprising the nucleic acid molecule of claim 1, 2, 3, 4 or 5.

7. A host cell containing the recombinant nucleic acid vector of claim 6.

8. An isolated nucleic acid molecule having the nucleotide sequence of SEQ ID NO:9.

9. An isolated nucleic acid molecule comprising the *Arabidopsis thaliana* cel1 functional promoter.

10. The isolated nucleic acid molecule of claim 9, wherein said cel1 functional promoter consists of a functional fragment of SEQ ID NO:1.

11. An isolated nucleic acid molecule which has at least 80% sequence identity to the nucleotide sequence of SEQ ID NO:2.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1770 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:1:

```
GTCGACCTGC AGGTCAACGG ATCACATGCA TCAGCACTAT TTACAACAAT CCTTTAGGGT      60

ATATGTTAGT CAACCCCGTA ACACCATTCG TACCCATTAA TCATGAACAT TTCGCAAAGT     120

TTTCCCACCA AAAACGGCGT CGGATAAGGT TTTTGGCATT TTGTGTTTCT TTTTTTGTGT     180

GCATAGCATA ATTTCATTTT AACCGTACTA TTCGAAGATT TTTAAATTGG ATAAAGATGA     240

TTCATTCATT ACATAGTCGC TTTGTTGTTA CTAGTGATAA ATTCATGTTA ATGATTCTAT     300

GATTTTCGGC CAGCTATCTC ATTAATTATT AAGACGTTTA AGTGGAGCTA TTAGCAATCG     360

TGTATGACAT AATGATTAGC ATTTTCATGT GCCATGCCCA TGCATGAGGC TTTTTTTTGT     420

TTAAAATTTT ATTCTATTAT ATCCGAATTT TGTTATATAC TAAATGAACA TTTGTCTCTG     480

ATTTGGTCTA CTAGTTAATT AACCTTTAGC TTCACTAATA AAAAATCTCA TGATTTTGAT     540
```

-continued

```
ACTTAAACCC AAAACATATT AAAAACAATT AGCAGTCTTT TAAATCGATA ATGTGCTTAG      600

ATGATTATAC GTTCGTAGGA AACTCTTTTG TTTCCAATGC ATGTTAAGAA CTAAGAACTC      660

GTATCCTTAA GCACCAATGC TTTATGCTTA ATGCCTCATT AGAGATATAA ACTGAGATTG      720

ACTGTGTTCT GAATCATCAT AATATAAGGC ACACAAAGAA CAGAACAGGA AATACTTAGC      780

AATATAATAG GTTTCCAATA AAAGTGAAGA AGAATACAAT AAACTTTTAT AAAAAAAAAA      840

GTATATAATA ATTTCACACT CGAATCAACC AAATGTAAGA TGTCTTGTCC ATTTACACAT      900

CACATGAGTA AGTGGATTAC AGATTGCAAT TGATGAAATC TGGATCTTAG CTAAAAATTT      960

ATTACGTTAC TATATACATC GAGTTTTAAG ATGTTCATAA TCACAACCAC AACCACAAGT     1020

TTGAAGAAAT AAGAAACAGA GTAATAATAT ATCAAATAAA ATTTCATGGC TGATGGAATC     1080

TTTTTTCTAA TTGTAGGTCC AAAAAAGCCT AAATTAATGG GGAAACAAAA ACCAAAATTC     1140

AATAGTAATT TTACTAATTA TGTCTTGGTT AAATAGAGTA AAAAGAAAAT TAATCACAAA     1200

CCTCCAAAAA TCAACTAATT GAGATCAAAA CACGTGTCGC ATGCCAATAG GGCGGTGGAT     1260

CACATGGTAA AAAAATTCAC TTTAATTTTT GTCTTTCTTC ATAATTCATC TCACAGATTT     1320

CAACTTCTCT TTTGGATTCT CTCACCGTAC ACCGTCGGCG TACCACTCCC CTTCCACACC     1380

GTCGGTATTA AAAATCTCAA ACCCTAAAAC CCGTATCCAA TAACCCACCC GGTCCAACCG     1440

GTTATTCAAA CCCGGTCAAT CCAAAATTCG CCTCGGAATC CAAACCTCCA TACCCAATCT     1500

AACATGGAAA AACCTCCAAT CACAAACCTC CACGTGGTGA TCACTCATTG GCTCTTATTC     1560

TGGAATCCAA GAGGACCTTT TTAGTATAAA GAGCCCCTTC GTTGGTCCTA TCACCTTCTC     1620

TCTCTCACAC ACTAACAGAA AGCACAAGAA AGAAGAGACA AAAGAATGGC GCGAAAATCC     1680

CTAATTTTCC CGGTGATTTT GCTCGCCGTT CTTCTCTTCT CTCCGCCGAT TTACTCCGCC     1740

GGTCACGATT ACCGCGACGC TCTCCGTAAA                                       1770

(2) INFORMATION FOR SEQ ID NO:2:

(i) SEQUENCE CHARACTERISTICS:
           (A) LENGTH: 1479 base pairs
           (B) TYPE: nucleic acid
           (C) STRANDEDNESS: double
           (D) TOPOLOGY: linear (ii) MOLECULE TYPE: DNA (xi) SEQUENCE DESCRIPTION: SEQ ID NO:2:

ATGGCGCGAA AATCCCTAAT TTTCCCGGTG ATTTTGCACG CCGTTCTTCT CTTCTCTCCG       60

CCGATTTACT CCGCCGGTCA CGATTACCGC GACGCTCTCC GTAAAAGCAT TCTCTTCTTC      120

GAAGGTCAAC GTTCCGGTAA ACTCCCTCCA GATCAACGCT TAAAATGGCG CCGTGACTCA      180

GCATTACGCG ACGGTTCCTC CGCCGGCGTT GACTTATCCG GTGGTTACTA CGACGCCGGA      240

GACAACATCA AGTTCGGTTT TCCGATGGCG TTCACAACAA CGATGCTTTC ATGGAGTATA      300

ATCGATTTCG GTAAAACCAT GGGACCTGAG CTTAGAAACG CCGTGAAAGC TGTTAAATGG      360

GGAACAGATT ACCTCCTTAA AGCGACGGCG ATTCCCGGAG TAGTCTTCGT CCAAGTCGGA      420

GACGCTTACT CCGATCATAA CTGTTGGGAA AGGCCTGAAG ATATGGACAC TCTCCGTACT      480

GTTTACAAAA TCGATAGAGC TCATCCTGGT TCTGACGTCG CTGGTGAAAC CGCAGCCGCT      540

TTAGCCGCCG CTTCAATCGT TTTTAGAAAA CGCGATCCTG CTTATTCCAG ACTTCTACTT      600

GACCGTGCCA CTAGGGTATT CGCGTTTGCT AACAGATATC GCGGCGCGTA TAGTAACAGT      660

CTCTACCACG CGGATTGTCC TTTTTACTGT GATTTCAACG GTTACCAGGA TGAGTTACTG      720
```

-continued

```
TGGGGAGCGG CATGGCTACA CAAAGCCTCG AGGAAACGAG CGTACAGAGA ATTCATTGTG    780

AAGAACGAGG TCATTCTTAA GGCTGGAGAT ACCATTAATG AGTTTGGTTG GGACAATAAG    840

CATGCTGGGA TTAATGTCTT AATCTCCAAG GAAGTGTTAA TGGGAAAAGC AGAGTATTTT    900

GAGTCTTTCA AGCAGAACGC AGATGGGTTT ATCTGTTCTA TATTGCCTGG AATTTCTCAC    960

CCCCAAGTCC AATACTCTCG AGGAGGGCTA CTAGTGAAGA CTGGAGGGAG TAACATGCAA   1020

CATGTAACAT CACTATCTTT CCTCCTATTG GCTTACTCTA ATTATCTGAG CCATGCCAAA   1080

AAGGTTGTGC CTTGTGGCGA ATTAACTGCT TCCCCATCTC TCCTCCGTCA AATCGCCAAG   1140

CGTCAGGTGG ATTACATTCT CGGAGACAAC CCGATGGGAC TGTCTTACAT GGTTGGATAC   1200

GGTCAAAAGT TTCCACGTAG GATTCATCAC CGTGGTAGCT CGGTTCCTTC GGTTTCAGCC   1260

CATCCAAGCC ACATAGGGTG CAAAGAAGGC TCTCGCTATT TCCTAAGCCC AAATCCTAAC   1320

CCAAACCTTT TGGTTGGTGC TGTAGTCGGT GGACCTAATG TCACTGATGC TTTTCCGGAT   1380

TCAAGACCTT ACTTTCAGCA GTCTGAGCCC ACGACTTATA TCAATGCACC ACTAGTGGGC   1440

CTTCTCGGTT ACTTCTCCGC CCATTCTACT TGGCGATGA                          1479
```

(2) INFORMATION FOR SEQ ID NO:3:

(i) SEQUENCE CHARACTERISTICS:
    (A) LENGTH: 1479 base pairs
    (B) TYPE: nucleic acid
    (C) STRANDEDNESS: double
    (D) TOPOLOGY: linear (ii) MOLECULE TYPE: DNA (ix) FEATURE:
    (A) NAME/KEY: Coding Sequence
    (B) LOCATION: 1...1476
    (D) OTHER INFORMATION:

(xi) SEQUENCE DESCRIPTION: SEQ ID NO:3:

```
ATG GCG CGA AAA TCC CTA ATT TTC CCG GTG ATT TTG CAC GCC GTT CTT     48
Met Ala Arg Lys Ser Leu Ile Phe Pro Val Ile Leu His Ala Val Leu
 1               5                  10                  15

CTC TTC TCT CCG CCG ATT TAC TCC GCC GGT CAC GAT TAC CGC GAC GCT     96
Leu Phe Ser Pro Pro Ile Tyr Ser Ala Gly His Asp Tyr Arg Asp Ala
                 20                  25                  30

CTC CGT AAA AGC ATT CTC TTC TTC GAA GGT CAA CGT TCC GGT AAA CTC    144
Leu Arg Lys Ser Ile Leu Phe Phe Glu Gly Gln Arg Ser Gly Lys Leu
             35                  40                  45

CCT CCA GAT CAA CGC TTA AAA TGG CGC CGT GAC TCA GCA TTA CGC GAC    192
Pro Pro Asp Gln Arg Leu Lys Trp Arg Arg Asp Ser Ala Leu Arg Asp
 50                  55                  60

GGT TCC TCC GCC GGC GTT GAC TTA TCC GGT GGT TAC TAC GAC GCC GGA    240
Gly Ser Ser Ala Gly Val Asp Leu Ser Gly Gly Tyr Tyr Asp Ala Gly
 65                  70                  75                  80

GAC AAC ATC AAG TTC GGT TTT CCG ATG GCG TTC ACA ACA ACG ATG CTT    288
Asp Asn Ile Lys Phe Gly Phe Pro Met Ala Phe Thr Thr Thr Met Leu
                 85                  90                  95

TCA TGG AGT ATA ATC GAT TTC GGT AAA ACC ATG GGA CCT GAG CTT AGA    336
Ser Trp Ser Ile Ile Asp Phe Gly Lys Thr Met Gly Pro Glu Leu Arg
             100                 105                 110

AAC GCC GTG AAA GCT GTT AAA TGG GGA ACA GAT TAC CTC CTT AAA GCG    384
Asn Ala Val Lys Ala Val Lys Trp Gly Thr Asp Tyr Leu Leu Lys Ala
         115                 120                 125

ACG GCG ATT CCC GGA GTA GTC TTC GTC CAA GTC GGA GAC GCT TAC TCC    432
Thr Ala Ile Pro Gly Val Val Phe Val Gln Val Gly Asp Ala Tyr Ser
 130                 135                 140
```

```
GAT CAT AAC TGT TGG GAA AGG CCT GAA GAT ATG GAC ACT CTC CGT ACT         480
Asp His Asn Cys Trp Glu Arg Pro Glu Asp Met Asp Thr Leu Arg Thr
145                 150                 155                 160

GTT TAC AAA ATC GAT AGA GCT CAT CCT GGT TCT GAC GTC GCT GGT GAA         528
Val Tyr Lys Ile Asp Arg Ala His Pro Gly Ser Asp Val Ala Gly Glu
                165                 170                 175

ACC GCA GCC GCT TTA GCC GCC GCT TCA ATC GTT TTT AGA AAA CGC GAT         576
Thr Ala Ala Ala Leu Ala Ala Ala Ser Ile Val Phe Arg Lys Arg Asp
            180                 185                 190

CCT GCT TAT TCC AGA CTT CTA CTT GAC CGT GCC ACT AGG GTA TTC GCG         624
Pro Ala Tyr Ser Arg Leu Leu Leu Asp Arg Ala Thr Arg Val Phe Ala
        195                 200                 205

TTT GCT AAC AGA TAT CGC GGC GCG TAT AGT AAC AGT CTC TAC CAC GCG         672
Phe Ala Asn Arg Tyr Arg Gly Ala Tyr Ser Asn Ser Leu Tyr His Ala
    210                 215                 220

GAT TGT CCT TTT TAC TGT GAT TTC AAC GGT TAC CAG GAT GAG TTA CTG         720
Asp Cys Pro Phe Tyr Cys Asp Phe Asn Gly Tyr Gln Asp Glu Leu Leu
225                 230                 235                 240

TGG GGA GCG GCA TGG CTA CAC AAA GCC TCG AGG AAA CGA GCG TAC AGA         768
Trp Gly Ala Ala Trp Leu His Lys Ala Ser Arg Lys Arg Ala Tyr Arg
                245                 250                 255

GAA TTC ATT GTG AAG AAC GAG GTC ATT CTT AAG GCT GGA GAT ACC ATT         816
Glu Phe Ile Val Lys Asn Glu Val Ile Leu Lys Ala Gly Asp Thr Ile
                260                 265                 270

AAT GAG TTT GGT TGG GAC AAT AAG CAT GCT GGG ATT AAT GTC TTA ATC         864
Asn Glu Phe Gly Trp Asp Asn Lys His Ala Gly Ile Asn Val Leu Ile
            275                 280                 285

TCC AAG GAA GTG TTA ATG GGA AAA GCA GAG TAT TTT GAG TCT TTC AAG         912
Ser Lys Glu Val Leu Met Gly Lys Ala Glu Tyr Phe Glu Ser Phe Lys
        290                 295                 300

CAG AAC GCA GAT GGG TTT ATC TGT TCT ATA TTG CCT GGA ATT TCT CAC         960
Gln Asn Ala Asp Gly Phe Ile Cys Ser Ile Leu Pro Gly Ile Ser His
305                 310                 315                 320

CCC CAA GTC CAA TAC TCT CGA GGA GGG CTA CTA GTG AAG ACT GGA GGG        1008
Pro Gln Val Gln Tyr Ser Arg Gly Gly Leu Leu Val Lys Thr Gly Gly
                325                 330                 335

AGT AAC ATG CAA CAT GTA ACA TCA CTA TCT TTC CTC CTA TTG GCT TAC        1056
Ser Asn Met Gln His Val Thr Ser Leu Ser Phe Leu Leu Leu Ala Tyr
                340                 345                 350

TCT AAT TAT CTG AGC CAT GCC AAA AAG GTT GTG CCT TGT GGC GAA TTA        1104
Ser Asn Tyr Leu Ser His Ala Lys Lys Val Val Pro Cys Gly Glu Leu
            355                 360                 365

ACT GCT TCC CCA TCT CTC CTC CGT CAA ATC GCC AAG CGT CAG GTG GAT        1152
Thr Ala Ser Pro Ser Leu Leu Arg Gln Ile Ala Lys Arg Gln Val Asp
        370                 375                 380

TAC ATT CTC GGA GAC AAC CCG ATG GGA CTG TCT TAC ATG GTT GGA TAC        1200
Tyr Ile Leu Gly Asp Asn Pro Met Gly Leu Ser Tyr Met Val Gly Tyr
385                 390                 395                 400

GGT CAA AAG TTT CCA CGT AGG ATT CAT CAC CGT GGT AGC TCG GTT CCT        1248
Gly Gln Lys Phe Pro Arg Arg Ile His His Arg Gly Ser Ser Val Pro
                405                 410                 415

TCG GTT TCA GCC CAT CCA AGC CAC ATA GGG TGC AAA GAA GGC TCT CGC        1296
Ser Val Ser Ala His Pro Ser His Ile Gly Cys Lys Glu Gly Ser Arg
                420                 425                 430

TAT TTC CTA AGC CCA AAT CCT AAC CCA AAC CTT TTG GTT GGT GCT GTA        1344
Tyr Phe Leu Ser Pro Asn Pro Asn Pro Asn Leu Leu Val Gly Ala Val
            435                 440                 445

GTC GGT GGA CCT AAT GTC ACT GAT GCT TTT CCG GAT TCA AGA CCT TAC        1392
Val Gly Gly Pro Asn Val Thr Asp Ala Phe Pro Asp Ser Arg Pro Tyr
        450                 455                 460
```

```
TTT CAG CAG TCT GAG CCC ACG ACT TAT ATC AAT GCA CCA CTA GTG GGC          1440
Phe Gln Gln Ser Glu Pro Thr Thr Tyr Ile Asn Ala Pro Leu Val Gly
465                 470                 475                 480

CTT CTC GGT TAC TTC TCC GCC CAT TCT ACT TGG CGA TGA                      1479
Leu Leu Gly Tyr Phe Ser Ala His Ser Thr Trp Arg
                485                 490
```

(2) INFORMATION FOR SEQ ID NO:4:

(i) SEQUENCE CHARACTERISTICS:
        (A) LENGTH: 492 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Arg Lys Ser Leu Ile Phe Pro Val Ile Leu His Ala Val Leu
1               5                   10                  15

Leu Phe Ser Pro Pro Ile Tyr Ser Ala Gly His Asp Tyr Arg Asp Ala
                20                  25                  30

Leu Arg Lys Ser Ile Leu Phe Glu Gly Gln Arg Ser Gly Lys Leu
            35                  40                  45

Pro Pro Asp Gln Arg Leu Lys Trp Arg Arg Asp Ser Ala Leu Arg Asp
        50                  55                  60

Gly Ser Ser Ala Gly Val Asp Leu Ser Gly Tyr Tyr Asp Ala Gly
65                  70                  75                  80

Asp Asn Ile Lys Phe Gly Phe Pro Met Ala Phe Thr Thr Thr Met Leu
                85                  90                  95

Ser Trp Ser Ile Ile Asp Phe Gly Lys Thr Met Gly Pro Glu Leu Arg
                100                 105                 110

Asn Ala Val Lys Ala Val Lys Trp Gly Thr Asp Tyr Leu Leu Lys Ala
                115                 120                 125

Thr Ala Ile Pro Gly Val Val Phe Val Gln Val Gly Asp Ala Tyr Ser
130                 135                 140

Asp His Asn Cys Trp Glu Arg Pro Glu Asp Met Asp Thr Leu Arg Thr
145                 150                 155                 160

Val Tyr Lys Ile Asp Arg Ala His Pro Gly Ser Asp Val Ala Gly Glu
                165                 170                 175

Thr Ala Ala Ala Leu Ala Ala Ala Ser Ile Val Phe Arg Lys Arg Asp
                180                 185                 190

Pro Ala Tyr Ser Arg Leu Leu Leu Asp Arg Ala Thr Arg Val Phe Ala
                195                 200                 205

Phe Ala Asn Arg Tyr Arg Gly Ala Tyr Ser Asn Ser Leu Tyr His Ala
210                 215                 220

Asp Cys Pro Phe Tyr Cys Asp Phe Asn Gly Tyr Gln Asp Glu Leu Leu
225                 230                 235                 240

Trp Gly Ala Ala Trp Leu His Lys Ala Ser Arg Lys Arg Ala Tyr Arg
                245                 250                 255

Glu Phe Ile Val Lys Asn Glu Val Ile Leu Lys Ala Gly Asp Thr Ile
                260                 265                 270

Asn Glu Phe Gly Trp Asp Asn Lys His Ala Gly Ile Asn Val Leu Ile
                275                 280                 285

Ser Lys Glu Val Leu Met Gly Lys Ala Glu Tyr Phe Glu Ser Phe Lys
290                 295                 300
```

```
Gln Asn Ala Asp Gly Phe Ile Cys Ser Ile Leu Pro Gly Ile Ser His
305                 310                 315                 320

Pro Gln Val Gln Tyr Ser Arg Gly Gly Leu Leu Val Lys Thr Gly Gly
            325                 330                 335

Ser Asn Met Gln His Val Thr Ser Ser Phe Leu Leu Leu Ala Tyr
            340                 345                 350

Ser Asn Tyr Leu Ser His Ala Lys Lys Val Val Pro Cys Gly Glu Leu
            355                 360                 365

Thr Ala Ser Pro Ser Leu Leu Arg Gln Ile Ala Lys Arg Gln Val Asp
370                 375                 380

Tyr Ile Leu Gly Asp Asn Pro Met Gly Leu Ser Tyr Met Val Gly Tyr
385                 390                 395                 400

Gly Gln Lys Phe Pro Arg Arg Ile His His Arg Gly Ser Ser Val Pro
                405                 410                 415

Ser Val Ser Ala His Pro Ser His Ile Gly Cys Lys Glu Gly Ser Arg
            420                 425                 430

Tyr Phe Leu Ser Pro Asn Pro Asn Pro Asn Leu Leu Val Gly Ala Val
            435                 440                 445

Val Gly Gly Pro Asn Val Thr Asp Ala Phe Pro Asp Ser Arg Pro Tyr
450                 455                 460

Phe Gln Gln Ser Glu Pro Thr Thr Tyr Ile Asn Ala Pro Leu Val Gly
465                 470                 475                 480

Leu Leu Gly Tyr Phe Ser Ala His Ser Thr Trp Arg
                485                 490
```

(2) INFORMATION FOR SEQ ID NO:5:

(i) SEQUENCE CHARACTERISTICS:
        (A) LENGTH: 499 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:5:

```
CCATGGCAGC GACATCATCA ATGTCAGTTG AATTTTACAA CTCTAACAAA TCAGCACAAA      60

CAAACTCAAT TACACCAATA ATCAAAATTA CTAACACATC TGACAGTGAT TTAAATTTAA     120

ATGACGTAAA AGTTAGATAT TATTACACAA GTGATGGTAC ACAAGGACAA ACTTTCTGGT     180

GTGACCATGC TGGTGCATTA TTAGGAAATA GCTATGTTGA TAACACTAGC AAAGTGACAG     240

CAAACTTCGT TAAAGAAACA GCAAGCCCAA CATCAACCTA TGATACATAT GTTGAATTTG     300

GATTTGCAAG CGGAGCAGCT ACTCTTAAAA AAGGACAATT TATAACTATT CAAGGAAGAA     360

TAACAAAATC AGACTGGTCA AACTACACTC AAACAAATGA CTATTCATTT GATGCAAGTA     420

GTTCAACACC AGTTGTAAAT CCAAAAGTTA CAGGATATAT AGGTGGAGCT AAAGTACTTG     480

GTACAGCACC ATAGGATCC                                                  499
```

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AAAAGTCGAC GAAGGTGATA GGACCAAC                                                              28

(2) INFORMATION FOR SEQ ID NO:7:

(i) SEQUENCE CHARACTERISTICS:
        (A) LENGTH: 163 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Ala Ala Thr Ser Ser Met Ser Val Glu Phe Tyr Asn Ser Asn Lys
 1               5                  10                  15

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Thr Gln Thr Asn Asp Tyr Ser Phe Asp Ala Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro
```

(2) INFORMATION FOR SEQ ID NO:8:

(i) SEQUENCE CHARACTERISTICS:
        (A) LENGTH: 494 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Asp Cys Ser Ser Pro Leu Ser Leu Phe His Leu Leu Val Cys
 1               5                  10                  15

Thr Val Met Val Lys Cys Cys Ser Ala Ser Asp Leu His Tyr Ser Asp
            20                  25                  30

Ala Leu Glu Lys Ser Ile Leu Phe Phe Glu Gly Gln Arg Ser Gly Lys
        35                  40                  45

Leu Pro Thr Asn Gln Arg Leu Thr Trp Arg Gly Asp Ser Gly Leu Ser
    50                  55                  60

Asp Gly Ser Ser Tyr His Val Asp Leu Val Gly Gly Tyr Tyr Asp Ala
65                  70                  75                  80

Gly Asp Asn Leu Lys Phe Gly Leu Pro Met Ala Phe Thr Thr Thr Met
                85                  90                  95
```

```
Leu Ala Trp Gly Ile Ile Glu Phe Gly Cys Leu Met Pro Glu Gln Val
            100                 105                 110

Glu Asn Ala Arg Ala Ala Leu Arg Trp Ser Thr Asp Tyr Leu Leu Lys
            115                 120                 125

Ala Ser Thr Ala Thr Ser Asn Ser Leu Tyr Val Gln Val Gly Glu Pro
            130                 135                 140

Asn Ala Asp His Arg Cys Trp Glu Arg Pro Glu Asp Met Asp Thr Pro
145                 150                 155                 160

Arg Asn Val Tyr Lys Val Ser Thr Gln Asn Pro Gly Ser Asp Val Ala
                165                 170                 175

Ala Glu Thr Ala Ala Ala Leu Ala Ala Ala Ser Ile Val Phe Gly Asp
            180                 185                 190

Ser Asp Ser Ser Tyr Ser Thr Lys Leu Leu His Thr Ala Val Lys Val
            195                 200                 205

Phe Glu Phe Ala Asp Gln Tyr Arg Gly Ser Tyr Ser Asp Ser Leu Gly
            210                 215                 220

Ser Val Val Cys Pro Phe Tyr Cys Ser Tyr Ser Gly Tyr Asn Asp Glu
225                 230                 235                 240

Leu Leu Trp Gly Ala Ser Trp Leu His Arg Ala Ser Gln Asn Ala Ser
                245                 250                 255

Tyr Met Thr Tyr Ile Gln Ser Asn Gly His Thr Leu Gly Ala Asp Asp
            260                 265                 270

Asp Asp Tyr Ser Phe Ser Trp Asp Asp Lys Arg Val Gly Thr Lys Val
            275                 280                 285

Leu Leu Ser Lys Gly Phe Leu Gln Asp Arg Ile Glu Glu Leu Gln Leu
            290                 295                 300

Tyr Lys Val His Thr Asp Asn Tyr Ile Cys Ser Leu Ile Pro Gly Thr
305                 310                 315                 320

Ser Ser Phe Gln Ala Gln Tyr Thr Pro Gly Gly Leu Leu Tyr Lys Gly
                325                 330                 335

Ser Ala Ser Asn Leu Gln Tyr Val Thr Ser Thr Ala Phe Leu Leu Leu
            340                 345                 350

Thr Tyr Ala Asn Tyr Leu Asn Ser Ser Gly Gly His Ala Ser Cys Gly
            355                 360                 365

Thr Thr Thr Val Thr Ala Lys Asn Leu Ile Ser Leu Ala Lys Lys Gln
            370                 375                 380

Val Asp Tyr Ile Leu Gly Gln Asn Pro Ala Lys Met Ser Tyr Met Val
385                 390                 395                 400

Gly Phe Gly Glu Arg Tyr Pro Gln His Val His His Arg Gly Ser Ser
                405                 410                 415

Leu Pro Ser Val Gln Val His Pro Asn Ser Ile Pro Cys Asn Ala Gly
            420                 425                 430

Phe Gln Tyr Leu Tyr Ser Ser Pro Pro Asn Pro Asn Ile Leu Val Gly
            435                 440                 445

Ala Ile Leu Gly Gly Pro Asp Asn Arg Asp Ser Phe Ser Asp Asp Arg
450                 455                 460

Asn Asn Tyr Gln Gln Ser Glu Pro Ala Thr Tyr Ile Asn Ala Pro Leu
465                 470                 475                 480

Val Gly Ala Leu Ala Phe Phe Ala Ala Asn Pro Val Thr Glu
                485                 490
```

(2) INFORMATION FOR SEQ ID NO:9:

(i) SEQUENCE CHARACTERISTICS:
        (A) LENGTH: 6000 base pairs (B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:9:

```
GTCGACCTGC AGGTCAACGG ATCACATGCA TCAGCACTAT TTACAACAAT CCTTTAGGGT      60

ATATGTTAGT CAACCCCGTA ACACCATTCG TACCCATTAA TCATGAACAT TTCGCAAAGT     120

TTTCCCACCA AAAACGGCGT CGGATAAGGT TTTTGGCATT TTGTGTTTCT TTTTTTGTGT     180

GCATAGCATA ATTTCATTTT AACCGTACTA TTCGAAGATT TTTAAATTGG ATAAAGATGA     240

TTCATTCATT ACATAGTCGC TTTGTTGTTA CTAGTGATAA ATTCATGTTA ATGATTCTAT     300

GATTTTCGGC CAGCTATCTC ATTAATTATT AAGACGTTTA AGTGGAGCTA TTAGCAATCG     360

TGTATGACAT AATGATTAGC ATTTTCATGT GCCATGCCCA TGCATGAGGC TTTTTTTTGT     420

TTAAAATTTT ATTCTATTAT ATCCGAATTT TGTTATATAC TAAATGAACA TTTGTCTCTG     480

ATTTGGTCTA CTAGTTAATT AACCTTTAGC TTCACTAATA AAAAATCTCA TGATTTTGAT     540

ACTTAAACCC AAAACATATT AAAAACAATT AGCAGTCTTT TAAATCGATA ATGTGCTTAG     600

ATGATTATAC GTTCGTAGGA AACTCTTTTG TTTCCAATGC ATGTTAAGAA CTAAGAACTC     660

GTATCCTTAA GCACCAATGC TTTATGCTTA ATGCCTCATT AGAGATATAA ACTGAGATTG     720

ACTGTGTTCT GAATCATCAT AATATAAGGC ACACAAAGAA CAGAACAGGA ATACTTAGC     780

AATATAATAG GTTTCCAATA AAAGTGAAGA AGAATACAAT AAACTTTTAT AAAAAAAAAA     840

GTATATAATA ATTTCACACT CGAATCAACC AAATGTAAGA TGTCTTGTCC ATTTACACAT     900

CACATGAGTA AGTGGATTAC AGATTGCAAT TGATGAAATC TGGATCTTAG CTAAAAATTT     960

ATTACGTTAC TATATACATC GAGTTTTAAG ATGTTCATAA TCACAACCAC AACCACAAGT    1020

TTGAAGAAAT AAGAAACAGA GTAATAATAT ATCAAATAAA ATTTCATGGC TGATGGAATC    1080

TTTTTTCTAA TTGTAGGTCC AAAAAAGCCT AAATTAATGG GGAAACAAAA ACCAAAATTC    1140

AATAGTAATT TTACTAATTA TGTCTTGGTT AAATAGAGTA AAAAGAAAAT TAATCACAAA    1200

CCTCCAAAAA TCAACTAATT GAGATCAAAA CACGTGTCGC ATGCCAATAG GGCGGTGGAT    1260

CACATGGTAA AAAAATTCAC TTTAATTTTT GTCTTTCTTC ATAATTCATC TCACAGATTT    1320

CAACTTCTCT TTTGGATTCT CTCACCGTAC ACCGTCGGCG TACCACTCCC CTTCCACACC    1380

GTCGGTATTA AAAATCTCAA ACCCTAAAAC CCGTATCCAA TAACCCACCC GGTCCAACCG    1440

GTTATTCAAA CCCGGTCAAT CCAAAATTCG CCTCGGAATC CAAACCTCCA TACCCAATCT    1500

AACATGGAAA AACCTCCAAT CACAAACCTC CACGTGGTGA TCACTCATTG GCTCTTATTC    1560

TGGAATCCAA GAGGACCTTT TTAGTATAAA GAGCCCCTTC GTTGGTCCTA TCACCTTCTC    1620

TCTCTCACAC ACTAACAGAA AGCACAAGAA AGAAGAGACA AAAGAATGGC GCGAAAATCC    1680

CTAATTTTCC CGGTGATTTT GCTCGCCGTT CTTCTCTTCT CTCCGCCGAT TTACTCCGCC    1740

GGTCACGATT ACCGCGACGC TCTCCGTAAA AGCATTCTCT TCTTCGAAGG TCAACGTTCC    1800

GGTAAACTCC CTCCAGATCA ACGCTTAAAA TGGCGCCGTG ACTCAGCATT ACGCGACGGT    1860

TCCTCCGCCG GCGTAAGTCT ACTCTACTAA CATACATTTC AAACTTCTCC TTCTTCTAAT    1920

CTCTAACTTT TCCGACGATA TTTCAAAAAT CTCAGGTTGA CTTATCCGGT GGTTACTACG    1980

ACGCCGGAGA CAACATCAAG TTCGGTTTTC CGATGGCGTT CACAACAACG ATGCTTTCAT    2040

GGAGTATAAT CGATTTCGGT AAAACCATGG GACCTGAGCT TAGAAACGCC GTGAAAGCTG    2100

TTAAATGGGG AACAGATTAC CTCCTTAAAG CGACGGCGAT TCCCGGAGTA GTCTTCGTCC    2160
```

```
AAGTCGGAGA CGCTTACTCC GATCATAACT GTTGGGAAAG GCCTGAAGAT ATGGACACTC    2220

TCCGCACTGT TTACAAAATC GATAGAGCTC ATCCTGGTTC TGACGTCGCT GGTGAAACCG    2280

CAGCCGCTTT AGCCGCCGCT TCAATCGTTT TTAGAAAACG CGATCCTGCT TATTCCAGAC    2340

TTCTACTTGA CCGTGCCACT AGGGTACGTT ACTCTGTTTT CACACTTTAA CCATTAGCAT    2400

TAACTGTGGT AATTAATTTT AATTATTACA AACATTTTAA TATTCTCTTT GTTTTTCTTT    2460

AATAGTCAAA TTTAATAGTC AAAAGATTT TAATTTTTAA TCAATTATTC TTTGCTTGTG     2520

AGATAAGAGA TTCGTGTCCA TATGCATTTA TAATAATTGT TTTATTTCAG TACTTTTTTG    2580

GGTGATGGTT GGTTCATTTC TATGATTCGT TTTTAATAAT TTGACTTTTT TGAGTATATT    2640

TATTCTTACG TATATGTACT ATTGAATAAA TATTTTTACT GACGTAGAGA AGATATATCA    2700

AATTCACGGA TCTGAAATAA AAATGTTGTA CCGTTGATCG CAGGTATTCG CGTTTGCTAA    2760

CAGATATCGC GGCGCGTATA GTAACAGTCT CTACCACGCG GTTTGTCCTT TTTACTGTGA    2820

TTTCAACGGT TACCAGGTAA AGTATTATAG TTACTCTTTA TTACCTATTT TTAGTATCAG    2880

CCGTTGGATG GTAAATGTTG ATTTTGACTG ACATGATCTG ATGGTGGTGT TGCAGGATGA    2940

GTTACTGTGG GGAGCGGCAT GGCTACACAA AGCCTCGAGG AAACGAGCGT ACAGAGAATT    3000

CATTGTGAAG AACGAGGTCA TTCTTAAGGC TGGAGATACC ATTAATGAGT TTGGCTGGGA    3060

CAATAAGCAT GCTGGGATTA ATGTCTTAAT CTCCAAGGTA ACCATCTTTA ATTATTCTTC    3120

TGGTCAATAT TGCATGGTTT TTGATGCGCA TTGATTGTTG CTTAATCTTT TAACTGTCAA    3180

AGATTTGGTG TGGAGGTATT AGGGGATAGT GGAGTTTTTT TGTTTGTTTT TGGATTTATG    3240

TTCTATGTTT GTTTGGTCGC AAGGGGACTT ACTAATGTAG CATAAGAATT AAATTAAAAC    3300

ATAGGTAGAG AGATGGTTGT GTCTGGTATA TCACGTGTTT GTGGCACGAC TTTTGATCAT    3360

ATAATTGGAA GTGGGGTTCA CATTTCAAAT TATATGTCCT ATGACCTATC TAGTTATTTT    3420

GGGTCTACCA TATGCTTCAT TATCATAAAA CAAACCCGCT TTAGATTAGA TGTGTGAACC    3480

AATCGAGTCG TTTCTTTAGA TATGTAGACA TATAAAAACT AAATCATGTT AGAGTCATGC    3540

TTAATATGGG ATATTAAATT AGAGAAGATA GAATGGGGGA TGGATGATTG GACCTTGCAC    3600

ATGATGATGA ATAATGGGAA TTAGCCAATT AGAAATGGTC ATGTGATGTG GGAGCTAAAT    3660

CTTAAGGTAA GACATACCTC ATTGGACATT CCCCTTTTTT TGTCCAGTGT GTGCTCAACA    3720

TACCTCCTAG ATTTGGCTTC ATATAATTTT AATAATATAA CATTACCAAT TGGAAGCCAG    3780

AGCCTCACAT GGACCCATGA TCCATGACTA CTTGACTAGT GAATGGATAA AAAGAGTGT    3840

GCATTTTTCG CATATATCTA TATTATATAA TATATAAACT TGATAATCCA ATGTAGGTAG    3900

GTGAAATGTA TACAGTATGA TTTTGTGAGT TTGCATGTGG TGTATCATAT TTGTGGTTTT    3960

GGATATAGAG TAAGTAAAAA CTAAGGTATA TAGCAACATT ATTATTACAA GTATCAGAAT    4020

CAGAGCATCA GGCCTATTGG GTCAAGTGGG GACAGTAAAA GAAGGAAAGG GGTAGAGAAG    4080

TCTTTGGTTA CTGTTACAAA GCATGTGGCT CAAAACTCAA AAGGCTGAGA AAACAATAAA    4140

TAAAGTATCG TGTGTCCCTT ACCAGTTCCC ATTCTGCTGC AATAGCCTAA GTGGTTTCTT    4200

TTTGTTTTTG TCATTTCTCA ACGGTCTCTT TTTGCTATAC TGATCAGATT GATTTGTCAA    4260

GGGCCTTTCA CCATCTCAGT TTTTCACATG GCGCTCTGTC TCAAGGCCCT TGTTCTTTCT    4320

TGTTATTTAT ATTTAGTCTT TGTCTTTATA GTGTTTTTTT GCTTCTTGTT TTGAAATTAC    4380

AGGAAGTGTT AATGGGAAAA GCAGAGTATT TTGAGTCTTT CAAGCAGAAC GCAGATGGGT    4440

TTATCTGTTC TATATTGCCT GGAATTTCTC ACCCCCAAGT CCAATACTCT CGAGGTAATA    4500

ATACAAAACC CCATCATTTT TTTTCTCAAT ATCAAAGTAC TTTTCCCACA TTCACGTGAT    4560
```

```
TTACTTTTGT CTTTTTCCTT CTAAAAAATT CAAACTTTTT TCTATGCTTA TCTTTAATTA    4620

ATTAGTAGTA ATCTGATTTC TTTTTGTCTT ACATATCACA GGAGGGCTAC TAGTGAAGAC    4680

TGGAGGGAGT AACATGCAAC ATGTAACATC ACTATCTTTC CTCCTATTGG CTTACTCTAA    4740

TTATCTGAGC CATGCCAAAA AGGTTGTGCC TTGTGGCGAA TTAACTGCTT CCCCATCTCT    4800

CCTCCGTCAA ATCGCCAAGC GTCAGGTAAG AGATTAAAAA AAAAAAAAAC ATTGGTCCCA    4860

ATTTTCAGAC CAAAAACAAA ATACATAGCC GTTTGGGTCT TGGGGACCAA AGCCTTATTG    4920

TTTTGGTGAT ATGTGAACAG GTGGATTACA TTCTCGGAGA CAACCCGATG GGACTGTCTT    4980

ACATGGTTGG ATACGGTCAA AAGTTTCCAC GTAGGATTCA TCACCGTGGT AGCTCGGTTC    5040

CTTCGGTTTC AGCCCATCCA AGCCACATAG GGTGCAAAGA AGGCTCTCGC TATTTCCTAA    5100

GCCCAAATCC TAACCCAAAC CTTTGGGTTG GTGCTGTAGT CGGTGGACCT AATGTCACTG    5160

ATGCTTTTCC GGATTCAAGA CCTTACTTTC AGCAGTCTGA GCCCACGACT TATATCAATG    5220

CACCACTAGT GGGCCTTCTC GGTTACTTCT CCGCCCATTC TACTTGGCGA TGAGGGAGGG    5280

CCTTATTACT TATTACTCTC TATCCTATTA GAGGTGTGCT GGAAACTTTA GGCCACCCTA    5340

AAACCCTTTT TTTTCTTTTT TAATGTTATT GCCACTCTTT ATTTTCTACT ACTTAACCAA    5400

TTGTATTGTA AGCCCGTAAT TAGTGAAGAA AGAGAAAGAG TCATGTCGGT GTCTACACTT    5460

ATTATATTCG CAGTCAATTA CTTGAATTAT TTGTTTGCAA GACGACTAGT TAATACTCGC    5520

TAGTACAAGT TGATATAATC ATCAGACCAA AGTTTGATTT TAAAGAGAAA AAAAGATCAT    5580

CGAACCAAAT TCAACAAAAG CAAAAACAGT TAAAACTAAA AAACTCAATG ATAGGTTTTG    5640

TGTGAAAAGT TTATTGTTTG TTTGGATTCC TACTAAAAAT TAAAATATCC ATCTATAGTT    5700

TTGCAAATCA AGCTTCATAA TGATTTCATC TCTGTTGGGC CTTCCTCATG GGGTGGTCT    5760

ACTTCCTCAT CTCTGTCCTT CTTAGTAAAA TTAAATGGTC CAGTTGACGG CCCAATAAGC    5820

CCATAGAAAA AGAAAATTAA TTTGGTTAGC TAAGAGTTCC GTTTGGTTTA CTATGATTCA    5880

TCTTGTTGTC TTTTGGCTAT GAGACCTAGT GCGCGTGTAT TATTGTTTAA GTTCGACGGT    5940

TACCCGAGGA TAGCTCACTC GATAATTCTA GGAATTTTTT ACTTAGCGCT GTGTGATCCT    6000
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Gly Tyr Tyr Asp Ala
1           5

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Cys Trp Glu Arg Pro Glu Asp Met
1           5

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GAATTCGGNG GNTANTANGA NGC                                         23

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GAATTCCATN TCNTCNGGNC GNTCCANCA                                29

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ATGGCGCGAA AATCCCTAAT                                          20

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TCATCGCCAA GTAGAA                                                16

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

AAAAAAGCTT ACCTGCAGGT CAACGG                                  26

(2) INFORMATION FOR SEQ ID NO:17:

(i) SEQUENCE CHARACTERISTICS:
        (A) LENGTH: 27 base pairs

-continued

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

AAAAGTCGAC TTTACGGAGA GCGTCGC                                              27

(2) INFORMATION FOR SEQ ID NO:18:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

AAAAGTCGAC ATGGCAGCGA CATCATCAA                                            29

(2) INFORMATION FOR SEQ ID NO:19:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

AAAAGGATCC CTATGGTGCT GTACCAAG                                             28

(2) INFORMATION FOR SEQ ID NO:20:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

AAAAGCATGC CGCGAAAATC CCTAATTT                                             28

(2) INFORMATION FOR SEQ ID NO:21:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:21:

AAAAGAATTC CTATGGTGCT GTACCAAG                                             28
```